United States Patent
Forsell

(10) Patent No.: US 8,965,523 B2
(45) Date of Patent: Feb. 24, 2015

(54) METHOD AND APPARATUS FOR SUPPLYING ENERGY TO AN IMPLANT

(71) Applicant: Peter Forsell, Bouveret (SE)

(72) Inventor: Peter Forsell, Bouveret (SE)

( * ) Notice: Subject to any disclaimer, the term of this patent is extended or adjusted under 35 U.S.C. 154(b) by 0 days.

(21) Appl. No.: 14/107,255

(22) Filed: Dec. 16, 2013

(65) Prior Publication Data

US 2014/0176063 A1    Jun. 26, 2014

Related U.S. Application Data

(63) Continuation of application No. 13/123,638, filed as application No. PCT/SE2009/000457 on Oct. 12, 2009, now Pat. No. 8,612,013.

(30) Foreign Application Priority Data

| Oct. 10, 2008 | (SE) | ........................ 0802147 |
| Oct. 10, 2008 | (WO) | ............... PCT/SE2008/000563 |
| Oct. 10, 2008 | (WO) | ............... PCT/SE2008/000585 |
| Apr. 14, 2009 | (SE) | ........................ 0900493 |

(51) Int. Cl.
| *A61N 1/00* | (2006.01) |
| *H02J 7/02* | (2006.01) |
| *A61N 1/378* | (2006.01) |
| *A61N 1/372* | (2006.01) |

(52) U.S. Cl.
CPC ............ *H02J 7/025* (2013.01); *A61N 1/3787* (2013.01); *A61F 2250/0001* (2013.01); *A61N 1/37223* (2013.01)
USPC .................................................. 607/60

(58) Field of Classification Search
USPC .................................................. 607/60
See application file for complete search history.

(56) References Cited

U.S. PATENT DOCUMENTS

| 6,240,318 | B1 | 5/2001 | Phillips |
| 7,295,878 | B1 | 11/2007 | Meadows et al. |
| 2001/0002441 | A1 | 5/2001 | Boveja |
| 2004/0039423 | A1 | 2/2004 | Dolgin |

(Continued)

FOREIGN PATENT DOCUMENTS

| WO | WO 019 79 08 | 12/2001 |

OTHER PUBLICATIONS

U.S. Appl. No. 13/384,387 (Forsell) filed Jan. 17, 2012.

(Continued)

*Primary Examiner* — Robert N Wieland

(57) ABSTRACT

A system is disclosed which comprises an implantable electrical medical device (100) with an internal energy receiver (102). The system also comprises an external energy source (104) located externally for supplying wireless energy to the internal energy receiver (102). The external energy source (104) has a primary coil (11) for transmitting energy inductively to a first secondary coil (10) in the energy receiver (102). The system is arranged to measure parameters related to a first coupling factor (C1) between the primary and the first secondary coil (10), and the external energy source (104) is adapted to transmit energy to the energy receiver (102) for enabling the medical device (100) to detect information related to the first coupling factor (C1). The medical device (100) is adapted to wirelessly send feedback information related to said first coupling factor (C1) to the external energy source (104) with the external energy source (104) being arranged to receive the feedback information and to perform a predetermined action based on said feedback information.

21 Claims, 20 Drawing Sheets

(56) References Cited

U.S. PATENT DOCUMENTS

| | | |
|---|---|---|
| 2005/0075697 A1 | 4/2005 | Olson et al. |
| 2006/0247737 A1 | 11/2006 | Olson et al. |
| 2007/0279020 A1 | 12/2007 | Mozzi et al. |
| 2008/0082143 A1 | 4/2008 | Dai et al. |
| 2008/0132974 A1 | 6/2008 | Strother et al. |
| 2009/0259273 A1* | 10/2009 | Figueiredo et al. ............. 607/32 |
| 2010/0211133 A1 | 8/2010 | Forsell |
| 2010/0211134 A1 | 8/2010 | Forsell |
| 2010/0217352 A1 | 8/2010 | Forsell |
| 2010/0217353 A1 | 8/2010 | Forsell |
| 2010/0222848 A1 | 9/2010 | Forsell |
| 2010/0222849 A1 | 9/2010 | Forsell |
| 2010/0234922 A1 | 9/2010 | Forsell |
| 2011/0193688 A1 | 8/2011 | Forsell |
| 2011/0196452 A1 | 8/2011 | Forsell |
| 2011/0278948 A1 | 11/2011 | Forsell |
| 2011/0301668 A1 | 12/2011 | Forsell |
| 2012/0112556 A1 | 5/2012 | Forsell |
| 2012/0119700 A1 | 5/2012 | Forsell |

OTHER PUBLICATIONS

U.S. Appl. No. 13/384,039 (Forsell) filed Jan. 13, 2012.
U.S. Appl. No. 13/130,648 (Forsell) filed Aug. 3, 2011.
U.S. Appl. No. 13/130,634 (Forsell) filed Aug. 3, 2011.
U.S. Appl. No. 13/123,638 (Forsell) filed Apr. 11, 2011.
U.S. Appl. No. 13/123,168 (Forsell) filed Apr. 7, 2011.
U.S. Appl. No. 12/738,182 (Forsell) filed Apr. 15, 2010.
U.S. Appl. No. 12/682,835 (Forsell) filed Apr. 13, 2010.
U.S. Appl. No. 12/682,831 (Forsell) filed Apr. 13, 2010.
U.S. Appl. No. 12/682,477 (Forsell) filed Apr. 9, 2010.
U.S. Appl. No. 12/682,404 (Forsell) filed Apr. 9, 2010.
U.S. Appl. No. 12/682,336 (Forsell) filed Apr. 9, 2010.
U.S. Appl. No. 12/682,327 (Forsell) filed Apr. 9, 2010.
International Search Report for PCT/SE2009/000457, mailed Feb. 18, 2010.
Written Opinion of the International Searching Authority for PCT/SE2009/000457, mailed Feb. 18, 2010.
Extended European Search Report in EP patent application No. 09819474.9 dated Jul. 18, 2012.

* cited by examiner

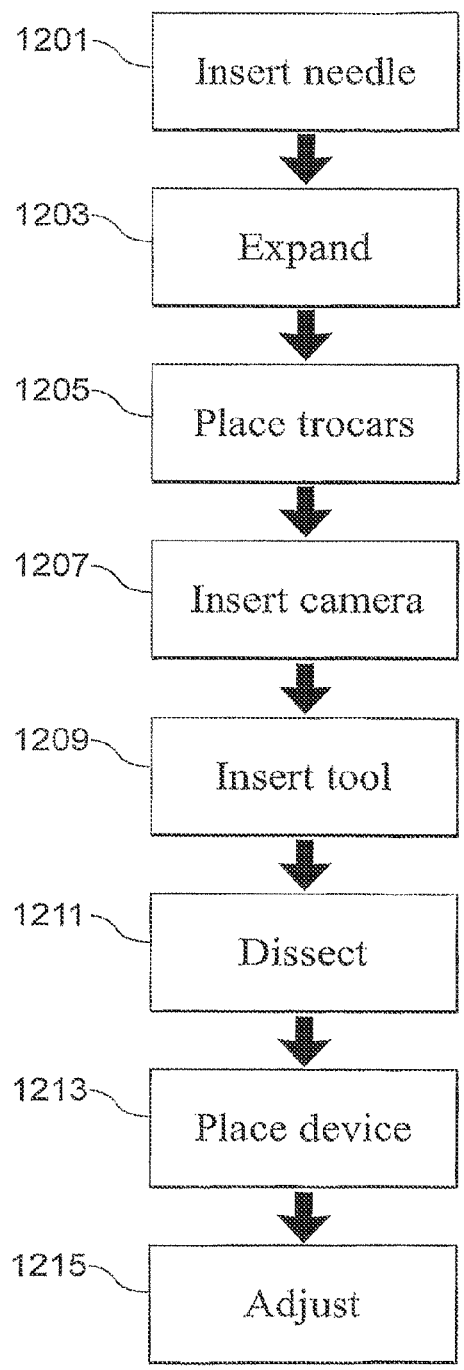
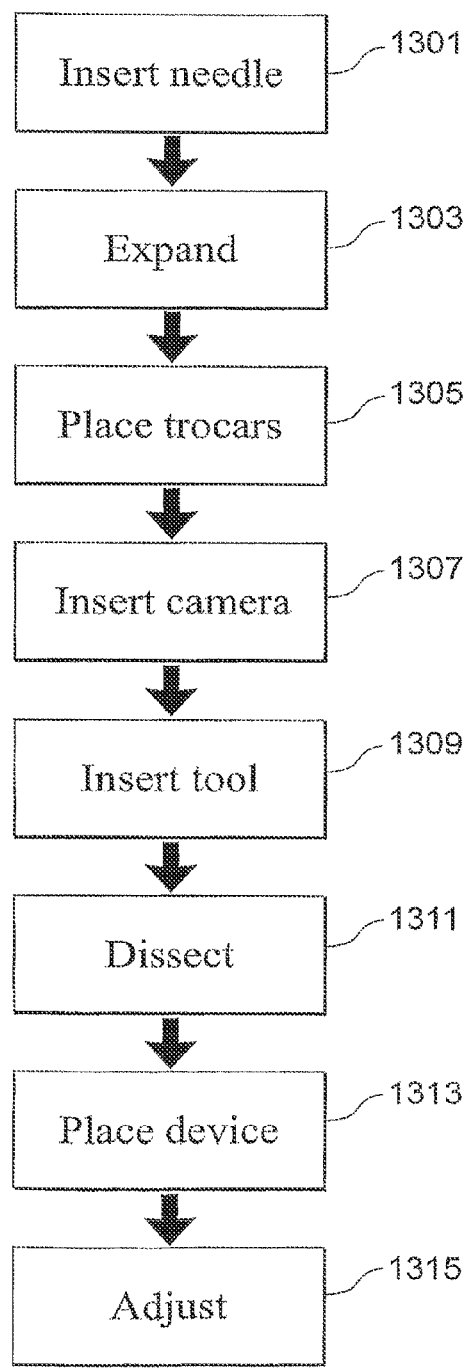

METHOD AND APPARATUS FOR SUPPLYING ENERGY TO AN IMPLANT

This application is a continuation of application Ser. No. 13/123,638, filed Apr. 11, 2011, which is the U.S. national phase of International Application No. PCT/SE2009/000457, filed 12 Oct. 2009, which designated the U.S. and claims priority to SE 0802147-9 filed 10 Oct. 2008, PCT/SE2008/000563, filed 10 Oct. 2008; PCT/SE2008/000585, filed 10 Oct. 2008, and SE 0900493-8 filed 14 Apr. 2009, the entire contents of each of which are hereby incorporated by reference.

TECHNICAL FIELD

The present invention relates generally to a method and apparatus for using a coupling factor between a device which is implantable in a patient and device which is external to the patient in order to perform an action.

BACKGROUND

Medical devices, designed to be implanted in a patient's body, are typically operated by means of electrical power. Such implantable medical devices include electrical and mechanical stimulators, motors, pumps, etc, which are designed to support or stimulate various body functions. Electrical power can be supplied to such an implanted medical device from a likewise implanted battery or from an external energy source that can supply any needed amount of electrical power intermittently or continuously without requiring repeated surgical operations.

An external energy source can transfer wireless energy to an implanted internal energy receiver located inside the patient and connected to the medical device for supplying received energy thereto. So-called TET (Transcutaneous Energy Transfer) devices are known that can transfer wireless energy in this manner. Thereby, no leads or the like penetrating the skin need to be used for connecting the medical device to an external energy source, such as a battery.

A TET device typically comprises an external energy source, i.e. external to the patient in whose body the implanted device is located, including a primary coil adapted to inductively transfer any amount of wireless energy by inducing a voltage in a secondary coil of an internal energy receiver which is implanted preferably just beneath the skin of a patient. The highest transfer efficiency is obtained when the primary coil is positioned close to the skin adjacent to and in alignment with the secondary coil, i.e. when a symmetry axis of the primary coil is parallel to that of the secondary coil.

Typically, the amount of energy required to operate an implanted medical device may vary over time depending on the operational characteristics of the device. For example, the device may be designed to switch on and off at certain intervals, or otherwise change its behavior, in order to provide a suitable electrical or mechanical stimulation, or the like. Such operational variations will naturally result in corresponding variations with respect to the amount of required energy.

Furthermore, the position of the external energy source relative to the implanted internal energy receiver is a factor that affects the efficiency of the energy transfer, which highly depends on the distance and relative angle between the source and the receiver. For example, when primary and secondary coils are used, changes in coil spacing result in a corresponding variation of the induced voltage. During operation of the medical device, the patient's movements will typically change the relative spacing of the external source and the internal receiver arbitrarily such that the transfer efficiency greatly varies.

If the transfer efficiency becomes low, the amount of energy supplied to the medical device may be insufficient for operating the device properly, so that its action must be momentarily stopped, naturally disturbing the intended medical effect of the device.

On the other hand, the energy supplied to the medical device may also increase drastically, if the relative positions of the external source and the internal receiver change in a way that unintentionally increases the transfer efficiency. This situation can cause severe problems since the implant cannot "consume" the suddenly very high amount of supplied energy. Unused excessive energy must be absorbed in some way, resulting in the generation of heat, which is highly undesirable. Hence, if excessive energy is transferred from the external energy source to the internal energy receiver, the temperature of the implant will increase, which may damage the surrounding tissue or otherwise have a negative effect on the body functions. It is generally considered that the temperature in the body should not increase more than three degrees to avoid such problems.

For example, U.S. Pat. No. 5,995,874 discloses a TET system in which the amount of transmitted energy from a primary coil is controlled in response to an indication of measured characteristics of a secondary coil, such as load current and voltage. The transmitted energy can be controlled by varying the current and voltage in the primary coil, transmission frequency or coil dimensions. In particular, a change is effected in the saturation point of the magnetic field between the coils, in order to adjust the power transfer efficiency. However, it is not likely that this solution will work well in practice, since a saturation point in the human tissue would not occur, given the magnetic field levels that are possible to use. Moreover, if the energy transmission must be increased considerably, e.g. to compensate for losses due to variations in alignment and/or spacing between the coils, the relatively high radiation generated may be damaging or unhealthy or unpleasant to the patient, as is well known.

An effective solution is thus needed for more accurately transferring energy to an implanted medical device to ensure proper operation thereof, as well as optimizing the cooperation between the external energy source and the internal energy receiver in general.

SUMMARY OF THE INVENTION

In order to improve the cooperation between an implanted device and an external energy source, as described above, the present invention discloses a system which comprises an electrically powered medical device. The medical device comprises an internal energy receiver arranged to power the medical device, and, as mentioned above, the medical device is implantable in a patient.

The system of the invention also comprises an external energy source adapted to be located externally to the patient for the wireless supply of energy to the internal energy receiver. The external energy source is equipped with a primary coil from which the external energy source is arranged to transmit said energy inductively to a first secondary coil in the energy receiver. The system is arranged to determine by measurements one or more parameters related to a first coupling factor between the primary and the first secondary coil, and the external energy source is adapted to transmit a first amount of energy to the energy receiver for enabling the medical device to detect information related to the first coupling factor.

According to the invention, the medical device is adapted to wirelessly send feedback information related to the first coupling factor to the external energy source, and the external energy source is arranged to receive the feedback information from the medical device; the external energy source is adapted to perform a predetermined action based on said feedback information.

Thus, by means of the invention, the feedback information can be used in order to, for example, optimize the positioning of the external energy source in relation to the internal energy receiver. Examples of other predetermined actions include calibrating the energy sent by the external energy source, or locating the implant as such.

In one embodiment, the action performed using the feedback information comprises optimizing the placement of the primary coil in relation to the first secondary coil in order to optimize said first coupling factor.

In a further embodiment, the system of the invention is adapted to use the first coupling factor in order to determine a second amount of energy to be transmitted by the external energy source to the internal energy receiver, with the second amount of energy being optimized to power or charge the medical device.

In one embodiment, the system of the invention is adapted to increase the first amount of energy until the first coupling factor is detected by the system.

In one embodiment of the system, the energy receiver comprises a first switch which is adapted to switch a connection between the first secondary coil and the medical implant on and off, in order to enable the system to measure the first coupling factor when the connection is off. Suitably, the system further comprises an implantable control unit adapted to control the switching on and off of the connection.

In one embodiment, the implantable control unit is comprised in the medical device.

In one embodiment of the system, the internal energy receiver comprises an electronic component connected to the first secondary coil for preventing the flow of electrical current between the first secondary coil and the medical implant during measurement of parameters related to the first coupling factor.

In one embodiment, the energy receiver comprises a half wave rectifying component for rectifying half of the pulse cycle of a received alternating current energy signal in the energy receiver, with the system being adapted to measure parameters related to the first coupling factor during at least part of the non-rectified half of one or more pulse cycles.

In one embodiment, the energy receiver further comprises a second secondary coil, so that the primary coil has the first coupling factor in relation to the first secondary coil and a second coupling factor in relation to the second secondary coil, with the first secondary coil being arranged to receive energy for powering the medical device and the second secondary coil being adapted to supply information related to the second coupling factor. The second coupling factor has a predetermined relation to the first coupling factor, and the one or more parameters related to the first coupling factor which are determined by measurements of the system are parameters which are related to the second coupling factor, so that the system is arranged to determine by measurements said second coupling factor. In this embodiment of the system, the feedback information related to the first coupling factor which is transmitted to the external energy source is information which is also related to the second coupling factor.

In one embodiment, the system is adapted to calibrate the amount of energy to be sent from the external energy source.

In one embodiment, the system is adapted to let the measured feedback information be calculated by integration.

In one embodiment, the system is adapted to let the measured feedback information be calculated by a derivative.

in yet another embodiment the external control unit of the external energy source is arranged to receive complete finished calculated information on said first or second coupling factors (C1; C2) from said internal control unit.

In one version of the "two coil embodiment", the feedback information which is related to the first coupling factor is related to the second coupling factor, and the system is adapted to use the feedback information in order to perform its action in order to optimize the placement of the primary coil in relation to the second secondary coil in order to optimise the second coupling factor, thereby also optimizing the first coupling factor, which is related to the second coupling factor.

In one version of the "two coil embodiment", the system is adapted to transmit a predetermined amount of energy from the external energy source, related to the second coupling factor, with the energy amount being optimized to charge or to initially operate the medical device.

In one version of the "two coil embodiment", the energy receiver comprises an electronic component connected to the second secondary coil for preventing or substantially reducing the flow of electrical current between the second secondary coil and the medical implant during the measurements of parameters related to the second coupling factor. Suitably, the electronic component is a diode.

In one version of the "two coil embodiment", the system is adapted to let the second secondary coil be substantially without an electrical load or with a load with an impedance above a first threshold when measuring parameters related to the second coupling factor.

In one version of the "two coil embodiment", the second secondary coil has an inductance which is smaller than the inductance of the first secondary coil by a predetermined amount and is adapted primarily to supply information about the second coupling factor.

In one version of the "two coil embodiment", the external energy source is adapted to use the feedback information to optimise the placement of said primary coil in relation to the first secondary coil for a maximized first coupling factor.

In one version of the "two coil embodiment", the external energy source is adapted to use the feedback information to optimize the placement of the primary coil in relation to the first secondary coil in order to optimize the energy supply in the energy receiver.

The invention also discloses the medical device of the system as a "stand-alone" device, as well as disclosing a method which essentially corresponds to the operation of the medical system and the medical device.

Thus, the invention also discloses a method for using an implantable electrically powered medical device comprising an internal energy receiver arranged to power the medical device. The method is used for letting the medical device interact with an external energy source located externally to a patient in whom the medical device is implanted to wirelessly supply energy to the internal energy receiver, and the method comprises using a primary coil in the external energy source for transmitting said energy inductively to a first secondary coil in the energy receiver, and the method also comprises determining by measurements one or more parameters related to a first coupling factor between the primary and the first secondary coil and using the external energy source for transmitting a first amount of energy to the energy receiver for enabling the medical device to detect information related to the first coupling factor. According to the method, the medical device is used to wirelessly send feedback information related to said first coupling factor to the external energy source and letting the external energy receive said feedback information from the medical device and letting the external energy source perform a predetermined action based on said feedback information.

In one embodiment, said action comprises optimizing the placement of the primary coil in relation to the first secondary coil in order to optimize said first coupling factor.

In one embodiment of the method, use is made of said first coupling factor to determine a second amount of energy to be transmitted by said external energy source to the internal energy receiver, and to optimize said second amount of energy in order to power or charge the medical device.

In one embodiment, the method further comprises increasing said first amount of energy until said first coupling factor is detected by the system.

In one embodiment, the method further comprises using an indicator in the external energy source in order to indicate a level of the first coupling factor.

In one embodiment, the method further comprises using an indicator in the external energy source in order to indicate an optimal placement of the primary coil in relation to said first secondary coil in order to optimize the first coupling factor.

In one embodiment, the method further comprises using a first switch in the energy receiver for switching a connection between the first secondary coil and the medical implant on and off, in order to enable the system to measure the first coupling factor when the connection is off.

In one embodiment, the method further comprises using an implantable control unit to control the switching on and off of said connection.

In one embodiment, the method further comprises letting the implantable control unit be comprised in the medical device.

In one embodiment, the method further comprises using an electronic switch as the first switch.

In one embodiment of the method, use is made in the internal energy receiver of an electronic component connected to the first secondary coil for preventing flow of electrical current between the first secondary coil and the medical implant during measurement of parameters related to the first coupling factor.

In one embodiment of the method, a diode is used as the electronic component.

In one embodiment of the method, the first secondary coil is substantially without electrical load when measuring the first coupling factor.

One embodiment of the method comprises rectifying half of the pulse cycle of a received alternating current energy signal in the energy receiver and measuring parameters related to the first coupling factor during at least part of the non-rectified half of one or more pulse cycles.

One embodiment of the method comprises measuring, directly or indirectly, over a predetermined period of time the difference between an electrical parameter related to the energy transmitted by the external energy source and an electrical parameter related to the amount of energy received by the internal energy receiver, and determining the balance between said electrical parameters in order to determine said first coupling factor.

According to one embodiment of the method, information related to the first coupling factor is stored in a memory unit, which preferably is adapted to be implanted.

According to one embodiment of the method, the energy receiver is further equipped with a second secondary coil, so that the primary coil has the first coupling factor in relation to the first secondary coil and a second coupling factor in relation to the second secondary coil. In this embodiment, the first secondary coil is used to receive energy for powering said medical device and the second secondary coil is used to supply information related to the second coupling factor, with the second coupling factor having a predetermined relation to the first coupling factor. The one or more parameters related to the first coupling factor which are determined by measurements of the system are parameters related to the second coupling factor, so that said measurements relate to the second coupling factor, and the feedback information related to the first coupling factor which is transmitted to the external energy source is information which is also related to the second coupling factor.

According to one embodiment of the method, the feedback information which is related to the first coupling factor is related to the second coupling factor, and the feedback information is used in order to perform said action in order to optimize the placement of the primary coil in relation to the second secondary coil in order to optimise the second coupling factor, thereby also optimizing said first coupling factor, related to said second coupling factor.

According to one embodiment of the method, a predetermined amount of energy is transmitted from the external energy source, related to the second coupling factor, the energy amount being optimized to charge or to initially operate the medical device.

According to one embodiment of the method, the energy receiver is equipped with an electronic component connected to said second secondary coil for preventing or substantially reducing the flow of electrical current between the second secondary coil and the medical implant during the measurements of parameters related to the second coupling factor.

According to one embodiment of the method, a diode is used as the electronic component.

According to one embodiment of the method, the second secondary coil is made substantially free of an electrical load or given a load with a high impedance, i.e. above a first threshold, when measuring parameters related to the second coupling factor.

According to one embodiment of the method, the second secondary coil has an inductance which is smaller than the inductance of the first secondary coil by a predetermined amount and is adapted for supplying information about said second coupling factor.

According to one embodiment of the method, use is made of a control unit to calculate the second coupling factor.

According to one embodiment of the method, the control unit is comprised in the external energy source.

According to one embodiment of the method, the external energy source is further made to comprise an electronic circuit for comparing the feedback information with the amount of energy transmitted by the external energy source.

According to one embodiment of the method, an analyzer unit is comprised in the electronic circuit in order to analyze the amount of energy being transmitted, and the analyzer unit is used to receive the feedback information related to the amount of energy received in the energy receiver and to determine an energy balance by comparing the amount of transmitted energy and the feedback information to calculate said second coupling factor.

According to one embodiment of the method, the external energy source is made to use said feedback information, in order to calibrate the level of said transmitted energy.

According to one embodiment of the method, the external energy source uses said feedback information to optimize the placement of said primary coil in relation to said first secondary coil for a maximized first coupling factor.

According to one embodiment of the method, the medical device receives information related to one of said first or second coupling factors from said external energy source and receives measured information within the medical device related to one of said first or second coupling factors and uses the received information in order to internally calculate the feedback information based on said received and measured information. The feedback information is transmitted from the medical device, and comprises information on one of said first or second coupling factors.

According to one embodiment of the method, the medical device uses an electronic circuit to compare received information related to the amount of energy transmitted by the external energy source and measured information related to the amount of energy received by said internal energy receiver.

According to one embodiment of the method, the external energy source is made to use said feedback information in order to calibrate the level of transmitted energy.

According to one embodiment of the method, the external energy source is adapted to use the feedback information in order to optimize the placement of the primary coil in relation to the first secondary coil, for optimizing the energy supply in the energy receiver.

In addition, a method is also provided for controlling transmission of wireless energy supplied to an electrically operable medical device implanted in a patient. The wireless energy is transmitted from an external energy source located outside the patient and is received by an internal energy receiver located inside the patient, the internal energy receiver being connected to the medical device for directly or indirectly supplying received energy thereto. An energy balance is determined between the energy sent by the external energy source and the energy received by the internal energy receiver. The transmission of wireless energy from the external energy source is then controlled based on the determined energy balance.

An apparatus is also provided for controlling transmission of wireless energy supplied to an electrically operable medical device implanted in a patient. The apparatus is adapted to transmit the wireless energy from an external energy source located outside the patient which is received by an internal energy receiver located inside the patient, the internal energy receiver being connected to the medical device for directly or indirectly supplying received energy thereto. The apparatus is further adapted to determine an energy balance between the energy sent by the external energy source and the energy received by the internal energy receiver, and to control the transmission of wireless energy from the external energy source, based on the determined energy balance.

The method and apparatus may be implemented according to different embodiments and features as follows:

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

In one alternative, substantially all energy used for the medical device is consumed (e.g. by the consuming part 200a of FIG. 2) to operate the medical device. In that case, the energy may be consumed after being stabilized in at least one energy stabilizing unit of the medical device.

In another alternative, substantially all energy used for the medical device is stored in the at least one energy storage device. In yet another alternative, the energy used for the medical device is partly consumed to operate the medical device and partly stored in the at least one energy storage device.

The energy received by the internal energy receiver may be stabilized by a capacitor, before the energy is supplied directly or indirectly to the medical device.

The difference between the total amount of energy received by the internal energy receiver and the total amount of consumed and/or stored energy may be directly or indirectly measured over time, and the energy balance can then be determined based on a detected change in the total amount difference.

The energy received by the internal energy receiver may further be accumulated and stabilized in an energy stabilizing unit, before the energy is supplied to the medical device. In that case, the energy balance may be determined based on a detected change followed over time in the amount of consumed and/or stored energy. Further, the change in the amount of consumed and/or stored energy may be detected by determining over time the derivative of a measured electrical parameter related to the amount of consumed and/or stored energy, where the derivative at a first given moment is corresponding to the rate of the change at the first given moment, wherein the rate of change includes the direction and speed of the change. The derivative may further be determined based on a detected rate of change of the electrical parameter.

The energy received by the internal energy receiver may be supplied to the medical device with at least one constant voltage, wherein the constant voltage is created by a constant voltage circuitry. In that case, the energy may be supplied with at least two different voltages, including the at least one constant voltage.

The energy received by the internal energy receiver may also be supplied to the medical device with at least one constant current, wherein the constant current is created by a constant current circuitry. In that case, the energy may be supplied with at least two different currents including the at least one constant current.

The energy balance may also be determined based on a detected difference between the total amount of energy received by the internal energy receiver and the total amount of consumed and/or stored energy, the detected difference being related to the integral over time of at least one measured electrical parameter related to the energy balance. In that case, values of the electrical parameter may be plotted over time as a graph in a parameter-time diagram, and the integral can be determined from the size of the area beneath the plotted graph. The integral of the electrical parameter may relate to the energy balance as an accumulated difference between the total amount of energy received by the internal energy receiver and the total amount of consumed and/or stored energy.

The energy storage device in the medical device may include at least one of: a rechargeable battery, an accumulator or a capacitor. The energy stabilizing unit may include at least one of: an accumulator, a capacitor or a semiconductor adapted to stabilize the received energy.

When the energy received by the internal energy receiver is accumulated and stabilized in an energy stabilizing unit before energy is supplied to the medical device and/or energy storage device, the energy may be supplied to the medical device and/or energy storage device with at least one constant voltage, as maintained by a constant voltage circuitry. In that case, the medical device and energy storage device may be supplied with two different voltages, wherein at least one voltage is constant, maintained by the constant voltage circuitry.

Alternatively, when the energy received by the internal energy receiver is accumulated and stabilized in an energy stabilizing unit before energy is supplied to the medical device and/or energy storage device, the energy may be supplied to the medical device and/or energy storage device with at least one constant current, as maintained by a constant current circuitry. In that case, the medical device and energy storage device may be supplied with two different currents wherein at least one current is constant, maintained by the constant current circuitry.

The wireless energy may be initially transmitted according to a predetermined energy consumption plus storage rate. In that case, the transmission of wireless energy may be turned off when a predetermined total amount of energy has been transmitted. The energy received by the internal energy receiver may then also be accumulated and stabilized in an energy stabilizing unit before being consumed to operate the medical device and/or stored in the energy storage device until a predetermined total amount of energy has been consumed and/or stored.

Further, the wireless energy may be first transmitted with the predetermined energy rate, and then transmitted based on the energy balance which can be determined by detecting the total amount of accumulated energy in the energy stabilizing unit. Alternatively, the energy balance can be determined by detecting a change in the current amount of accumulated energy in the energy stabilizing unit. In yet another alternative, the energy balance, can be determined by detecting the direction and rate of change in the current amount of accumulated energy in the energy stabilizing unit.

The transmission of wireless energy may be controlled such that an energy reception rate in the internal energy receiver corresponds to the energy consumption and/or storage rate. In that case, the transmission of wireless energy may be turned off when a predetermined total amount of energy has been consumed.

The energy received by the internal energy receiver may be first accumulated and stabilized in an energy stabilizing unit, and then consumed or stored by the medical device until a predetermined total amount of energy has been consumed. In that case, the energy balance may be determined based on a detected total amount of accumulated energy in the energy stabilizing unit. Alternatively, the energy balance may be determined by detecting a change in the current amount of accumulated energy in the energy stabilizing unit. In yet another alternative, the energy balance may be determined by detecting the direction and rate of change in the current amount of accumulated energy in the energy stabilizing unit.

Suitable sensors may be used for measuring certain characteristics of the medical device and/or detecting the current condition of the patient, somehow reflecting the required amount of energy needed for proper operation of the medical device. Thus, electrical and/or physical parameters of the medical device and/or physical parameters of the patient may be determined, and the energy can then be transmitted with a transmission rate which is determined based on the parameters. Further, the transmission of wireless energy may be controlled such that the total amount of transmitted energy is based on said parameters.

The energy received by the internal energy receiver may be first accumulated and stabilized in an energy stabilizing unit, and then consumed until a predetermined total amount of energy has been consumed. The transmission of wireless energy may further be controlled such that an energy reception rate at the internal energy receiver corresponds to a predetermined energy consumption rate.

Further, electrical and/or physical parameters of the medical device and/or physical parameters of the patient may be determined, in order to determine the total amount of transmitted energy based on the parameters. In that case, the energy received by the internal energy receiver may be first accumulated and stabilized in an energy stabilizing unit, and then consumed until a predetermined total amount of energy has been consumed.

The energy is stored in the energy storage device according to a predetermined storing rate. The transmission of wireless energy may then be turned off when a predetermined total amount of energy has been stored. The transmission of wireless energy can be further controlled such that an energy reception rate at the internal energy receiver corresponds to the predetermined storing rate.

The energy storage device of the medical device may comprise a first storage device and a second storage device, wherein the energy received by the internal energy receiver is first stored in the first storage device, and the energy is then supplied from the first storage device to the second storage device at a later stage.

When using the first and second storage devices in the energy storage device, the energy balance may be determined in different ways. Firstly, the energy balance may be determined by detecting the current amount of energy stored in the first storage device, and the transmission of wireless energy may then be controlled such that a storing rate in the second storage device corresponds to an energy reception rate in the internal energy receiver. Secondly, the energy balance may be determined based on a detected total amount of stored energy in the first storage device. Thirdly, the energy balance may be determined by detecting a change in the current amount of stored energy in the first storage device. Fourthly, the energy balance may be determined by detecting the direction and rate of change in the current amount of stored energy in the first storage device.

Stabilized energy may be first supplied from the first storage device to the second storage device with a constant current, as maintained by a constant current circuitry, until a measured voltage over the second storage device reaches a predetermined maximum voltage, and thereafter supplied from the first storage device to the second storage energy storage device with a constant voltage, as maintained by a constant voltage circuitry. In that case, the transmission of wireless energy may be turned off when a predetermined minimum rate of transmitted energy has been reached.

The transmission of energy may further be controlled such that the amount of energy received by the internal energy receiver corresponds to the amount of energy stored in the second storage device. In that case, the transmission of energy may be controlled such that an energy reception rate at the internal energy receiver corresponds to an energy storing rate in the second storage device. The transmission of energy may also be controlled such that a total amount of received energy at the internal energy receiver corresponds to a total amount of stored energy in the second storage device.

In the case when the transmission of wireless energy is turned off when a predetermined total amount of energy has been stored, electrical and/or physical parameters of the medical device and/or physical parameters of the patient may be determined during a first energy storing procedure, and the predetermined total amount of energy may be stored in a subsequent energy storing procedure based on the parameters.

When electrical and/or physical parameters of the medical device and/or physical parameters of the patient are determined, the energy may be stored in the energy storage device with a storing rate which is determined based on the parameters. In that case, a total amount of energy may be stored in the energy storage device, the total amount of energy being determined based on the parameters. The transmission of wireless energy may then be automatically turned off when the total amount of energy has been stored. The transmission of wireless energy may further be controlled such that an energy reception rate at the internal energy receiver corresponds to the storing rate.

When electrical and/or physical parameters of the medical device and/or physical parameters of the patient are determined, a total amount of energy may be stored in the energy storage device, the total amount of energy being determined based on said parameters. The transmission of energy may then be controlled such that the total amount of received energy at the internal energy receiver corresponds to the total amount of stored energy. Further, the transmission of wireless energy may be automatically turned off when the total amount of energy has been stored.

When the energy used for the medical device is partly consumed and partly stored, the transmission of wireless energy may be controlled based on a predetermined energy consumption rate and a predetermined energy storing rate. In that case, the transmission of energy may be turned off when a predetermined total amount of energy has been received for consumption and storage. The transmission of energy may also be turned off when a predetermined total amount of energy has been received for consumption and storage.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When electrical and/or physical parameters of the medical device and/or physical parameters of the patient are determined, the energy may be supplied from the energy storage device to the medical device for consumption with a supply rate which is determined based on said parameters. In that case, the total amount of energy supplied from the energy storage device to the medical device for consumption, may be based on said parameters.

When electrical and/or physical parameters of the medical device and/or physical parameters of the patient are determined, a total amount of energy may be supplied to the medical device for consumption from the energy storage device, where the total amount of supplied energy is determined based on the parameters.

When the energy received by the internal energy receiver is accumulated and stabilized in an energy stabilizing unit, the energy balance may be determined based on an accumulation rate in the energy stabilizing unit, such that a storing rate in the energy storage device corresponds to an energy reception rate in the internal energy receiver.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

When using the first and second storage devices in the energy storage device, the second storage device may directly or indirectly supply energy to the medical device, wherein the change of the difference corresponds to a change of the amount of energy accumulated in the first storage unit. The energy balance may then be determined by detecting a change over time in the energy storing rate in the first storage device, the energy balance corresponding to the change. The change in the amount of stored energy may also be detected by determining over time the derivative of a measured electrical parameter indicating the amount of stored energy, the derivative corresponding to the change in the amount of stored energy. A rate of change of the electrical parameter may also be detected, the derivative being related to the change rate. The electrical parameter may be a measured voltage and/or current related to the energy balance.

The first storage device may include at least one of: a capacitor and a semiconductor, and the second storage device includes at least one of: a rechargeable battery, an accumulator and a capacitor.

As mentioned above, the wireless energy may be transmitted inductively from a primary coil in the external energy source to a secondary coil in the internal energy receiver. However, the wireless energy may also be transmitted non-inductively. For example, the wireless energy may be transmitted by means of sound or pressure variations, radio or light. The wireless energy may also be transmitted in pulses or waves and/or by means of an electric field.

When the wireless energy is transmitted from the external energy source to the internal energy receiver in pulses, the transmission of wireless energy may be controlled by adjusting the width of the pulses.

When the difference between the total amount of energy received by the internal energy receiver and the total amount of consumed energy is measured over time, directly or indirectly, the energy balance may be determined by detecting a change in the difference. In that case, the change in the amount of consumed energy may be detected by determining over time the derivative of a measured electrical parameter related to the amount of consumed energy, the derivative corresponding to the rate of the change in the amount of consumed energy, wherein the rate of change includes the direction and speed of the change. A rate of change of the electrical parameter may then be detected, the derivative being related to the detected change rate.

When using the first and second storage devices in the energy storage device, the first storage device may be adapted to be charged at a relatively higher energy charging rate as compared to the second storage device, thereby enabling a relatively faster charging. The first storage device may also be adapted to be charged at multiple individual charging occasions more frequently as compared to the second storage device, thereby providing relatively greater life-time in terms of charging occasions. The first storage device may comprise at least one capacitor. Normally, only the first storage may be charged and more often than needed for the second storage device.

When the second storage device needs to be charged, to reduce the time needed for charging, the first storage device is charged at multiple individual charging occasions, thereby leaving time in between the charging occasions for the first storage device to charge the second storage device at a relatively lower energy charging rate. When electrical parameters of the medical device are determined, the charging of the second storage device may be controlled based on the parameters. A constant current or stabilizing voltage circuitry may be used for storing energy in the second storage device.

A method is thus provided for controlling transmission of wireless energy supplied to an electrically operable medical device implanted in a mammal patient. The wireless energy is transmitted by means of a primary coil in an external energy source located outside the patient and received inductively by means of a secondary coil in an internal energy receiver located inside the patient. The internal energy receiver is connected to the medical device for directly or indirectly supplying received energy thereto. Feedback control information is transferred from the secondary coil to the primary coil by switching the secondary coil on and off to induce a detectable impedance load variation in the primary coil encoding the feedback control information. The feedback control information relates to the energy received in the medical device and is used for controlling the transmission of wireless energy from the external energy source.

An apparatus is also provided for controlling transmission of wireless energy supplied to an electrically operable medical device implanted in a mammal patient. The apparatus comprises an external energy source adapted to transmit the wireless energy by means of a primary coil when located outside the patient, and an internal energy receiver adapted to receive the transmitted wireless energy inductively by means of a secondary coil when located inside the patient, and to directly or indirectly supply received energy to the medical device. The internal energy receiver is further adapted to transfer feedback control information from the secondary coil to the primary coil in accordance with the above method.

The method and apparatus may be implemented according to different embodiments and features as follows:

In one embodiment, an internal control unit controls the on and off switching of the secondary coil, wherein the feedback control information may include at least one predetermined parameter relating to the received energy. The predetermined parameter may also be variable. The feedback control information may also relate to the received energy and require artificial intelligence to be generated. An implantable switch may be used to execute the on and off switching of the secondary coil as controlled by the internal control unit. The switch may be an electronic switch such as a transistor. Further, the internal control unit may comprise a memory for storing the transferred feedback control information.

In another embodiment, an internal control unit determines an energy balance between the energy received by the internal energy receiver and the energy used for the medical device, where the feedback control information relates to the determined energy balance. An external control unit then controls the transmission of wireless energy from the external energy source based on the determined energy balance and using the feedback control information.

Further embodiments comprise an apparatus wherein the feedback information is related to the amount of energy being received in the internal energy receiver.

In one embodiment of the apparatus, the external energy source further comprises an electronic circuit for comparing the feedback information with the amount of energy transmitted by the external energy source.

In one embodiment of the apparatus, the electronic circuit comprises an analyzer adapted to analyze the amount of energy being transmitted and adapted to receive the feedback information related to the amount of energy received in the receiver, and further adapted to determine the special energy balance by comparing the amount of transmitted energy and the feedback information related to the amount of received information.

In one embodiment of the apparatus, the external energy source is adapted to use said feedback information to adjust the level of said transmitted energy.

In one embodiment of the apparatus, the external energy source is adapted to transfer data related to the amount of transmitted energy to the receiver, and wherein the feedback information is related to the amount of energy received in the receiver the receiver compared to the amount of said transmitted energy.

In one embodiment of the apparatus, external energy source is adapted to use said feedback information to adjust the level of said transmitted energy.

In one embodiment of the apparatus, the feedback information is related to a coupling factor between the primary coil and the secondary coil.

In one embodiment of the apparatus, the external energy source is adapted to increase the amount of transferred energy to the internal energy receiver until a predetermined response of said coupling factor is detected.

In one embodiment of the apparatus, the external energy source further comprises an indicator adapted to indicate a level of the coupling factor.

In one embodiment of the apparatus, the external energy source further comprises an indicator adapted to indicate an optimal placement of said secondary coil in relation to said primary coil to optimize said coupling factor.

In one embodiment, an apparatus for controlling transmission of wireless energy supplied to an electrically operable medical device when implanted in a mammal patient comprises:
an external energy source adapted to transmit said wireless energy by means of a primary coil when located outside the patient,
an internal energy receiver adapted to receive the transmitted wireless energy inductively by means of a secondary coil when located inside the patient, and to directly or indirectly supply received energy to the medical device,
wherein the internal energy source is adapted to transfer feedback control information from the secondary coil to the primary coil by switching the secondary coil on and off to induce a detectable impedance load variation in the primary coil encoding the feedback control information, where said feedback control information reflects a required amount of energy for operating the medical device and is used for controlling the transmission of wireless energy from the external energy source.

In one embodiment the apparatus comprises an internal control unit adapted to control said on and off switching of the secondary coil, wherein the feedback control information includes at least one predetermined parameter relating to the received energy. The predetermined parameter is preferably variable.

In one embodiment the apparatus comprises an internal control unit adapted to control said on and off switching of the secondary coil, wherein the feedback control information is intelligent and variable relating relates to the received energy and requires artificial intelligence to be generated.

In one embodiment the apparatus comprises an implantable switch adapted to execute said on and off switching of the secondary coil as controlled by the internal control unit. The switch is preferably an electronic switch, such as a transistor.

In one embodiment of the apparatus, the internal control unit comprises a memory for storing the transferred feedback control information.

The apparatus may comprise an internal control unit 108 adapted to determine an energy balance between the energy received by the internal energy receiver and the energy used for the medical device, said feedback control information relating to the determined energy balance, and an external control unit 106 adapted to control the transmission of wireless energy from the external energy source based on the determined energy balance and using said feedback control information.

In one embodiment the apparatus comprises an external control unit adapted to determine an energy balance between the energy received by the internal energy receiver and the energy used for the medical device based on said feedback control information comprising measurements relating to characteristics of the medical device, and to control the transmission of wireless energy from the external energy source based on the determined energy balance and using said feedback control information.

A method is provided wherein the feedback information is related to the amount of energy being received in the internal energy receiver.

A method is provided wherein an electronic circuit in the external energy source compares the feedback information with the amount of energy transmitted by the external energy source.

A method is provided wherein an analyzer in the electronic circuit analyzes the amount of energy being transmitted and receives the feedback information related to the amount of energy received in the receiver, and further determines the special energy balance by comparing the amount of transmitted energy and the feedback information related to the amount of received information.

A method is provided wherein the external energy source uses said feedback information to adjust the level of said transmitted energy.

A method is provided wherein the external energy source transfers data related to the amount of transmitted energy to the receiver, and wherein the feedback information is related to the amount of energy received in the receiver the receiver compared to the amount of said transmitted energy.

A method is provided wherein external energy source uses said feedback information to adjust the level of said transmitted energy.

A method is provided wherein the feedback information is related to a coupling factor between the primary coil and the secondary coil.

A method is provided wherein the external energy source increases the amount of transferred energy to the internal energy receiver until a predetermined response of said coupling factor is detected.

A method is provided wherein an indicator in the external energy source indicates a level of the coupling factor.

A method is provided wherein an indicator in the external energy source indicates an optimal placement of said secondary coil in relation to said primary coil to optimize said coupling factor.

A method of controlling transmission of wireless energy supplied to an electrically operable medical device 100 implanted in a mammal patient is provided, said wireless energy being transmitted by means of a primary coil in an external energy source 104 located outside the patient and received inductively by means of a secondary coil in an internal energy receiver 102 located inside the patient, the internal energy receiver being connected to the medical device for directly or indirectly supplying received energy thereto, wherein feedback control information (S) is transferred from the secondary coil to the primary coil by switching the secondary coil on and off to induce a detectable impedance load variation in the primary coil encoding the feedback control information, where the feedback control information reflects the amount of energy received in the medical device and is used for controlling the transmission of wireless energy from the external energy source.

A method is provided wherein said on and off switching of the secondary coil is controlled by an internal control unit 108, and the feedback control information includes at least one predetermined parameter relating to the received energy.

A method is provided wherein said predetermined parameter is variable.

A method is provided wherein said on and off switching of the secondary coil is controlled by an internal control unit 108, and the feedback control information relates to the received energy and requires artificial intelligence to be generated.

A method is provided wherein said on and off switching of the secondary coil is executed by means of an implantable switch as controlled by the internal control unit.

A method is provided wherein the switch is an electronic switch such as a transistor.

A method is provided wherein the transferred feedback control information is stored in a memory of the internal control unit.

A method is provided, wherein an energy balance between the energy received by the internal energy receiver and the energy used for the medical device is determined, said feedback control information relating to the determined energy balance, and the transmission of wireless energy from the external energy source is controlled based on the determined energy balance and using said feedback control information.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Thus there is provided a method of transmitting wireless energy from an external energy transmitting device placed externally to a human body to an internal energy receiver placed internally in the human body, the method comprising:

applying to the external transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Also there is provided an apparatus adapted to transmit wireless energy from an external energy transmitting device placed externally to a human body to an internal energy receiver placed internally in the human body, the apparatus comprising, a first electric circuit to supply electrical pulses to the external transmitting device, said electrical pulses having leading and trailing edges, said transmitting device adapted to supply wireless energy, wherein the electrical circuit being adapted to vary the lengths of first time intervals between successive leading and trailing edges of the electrical pulses and/or the lengths of second time intervals between successive trailing and leading edges of the electrical pulses, and wherein the transmitted wireless energy, generated from the electrical pulses having a varied power, the power depending on the lengths of the first and/or second time intervals.

The method and apparatus may be implemented according to different embodiments and features as follows: In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

When applying electrical pulses to the external energy source, the electrical pulses may generate an electromagnetic field over the external energy source, the electromagnetic field being varied by varying the first and second time intervals, and the electromagnetic field may induce electrical pulses in the internal energy receiver, the induced pulses carrying energy transmitted to the internal energy receiver. The wireless energy is then transmitted in a substantially purely inductive way from the external energy source to the internal energy receiver.

The electrical pulses may be released from the first electrical circuit with such a frequency and/or time period between leading edges of the consecutive pulses, so that when the lengths of the first and/or second time intervals are varied, the resulting transmitted energy are varied. When applying the electrical pulses, the electrical pulses may have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

The method or the system may comprise calculating at least one of the parameters which are measured by integration.

The method or the system may comprise calculating at least one of the parameters which are measured as a derivative.

BRIEF DESCRIPTION OF THE DRAWINGS

The present invention will now be described in more detail and with reference to the accompanying drawings, in which:

FIGS. 19-22 are flowcharts illustrating different surgical methods.

DETAILED DESCRIPTION OF PREFERRED EMBODIMENTS

Figure 1:
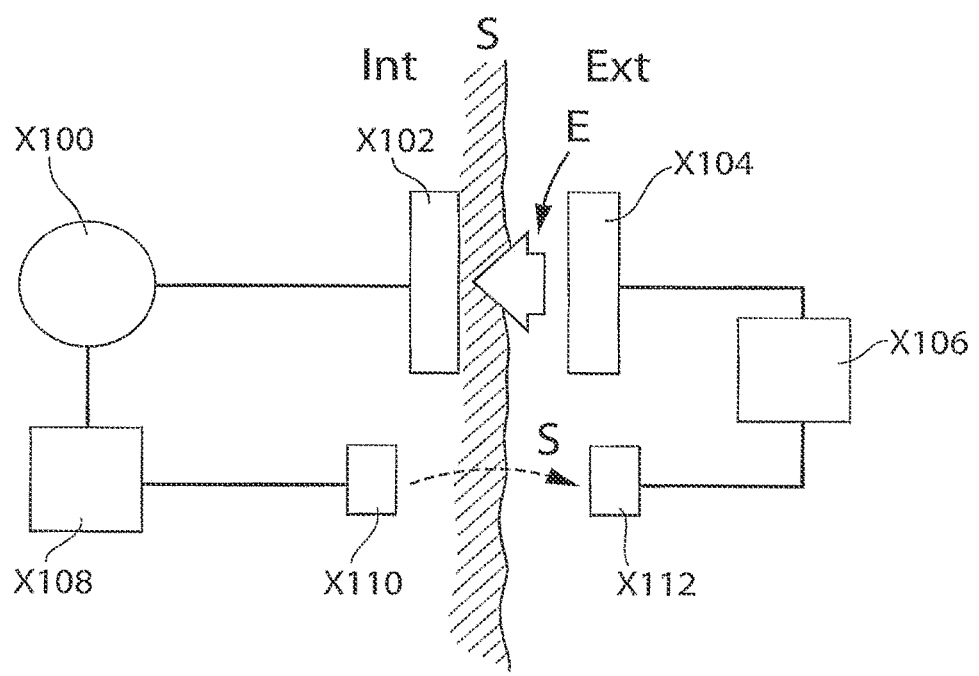
FIG. 1 is a schematic block diagram illustrating an arrangement for supplying an accurate amount of energy to an electrically operable medical device.

FIG. 1 shows a first embodiment of a system of the invention. As shown in FIG. 1, the system comprises an implantable medical device X100 which is electrically powered and which is shown in FIG. 1 as being implanted in a patient, the skin of the patient being indicted in FIG. 1 by means of a line S. As shown in FIG. 1, the medical device also comprises an internal energy receiver X102 which is arranged to power the medical device.

The system also comprises an external energy source X104 which, as shown in FIG. 1, is adapted to be located externally to the patient for wireless supplying energy to the internal energy receiver X102.

Versions of one embodiment of the invention will now be described by means of reference to FIG. 1 and FIGS. 4-8.

Figure 4:
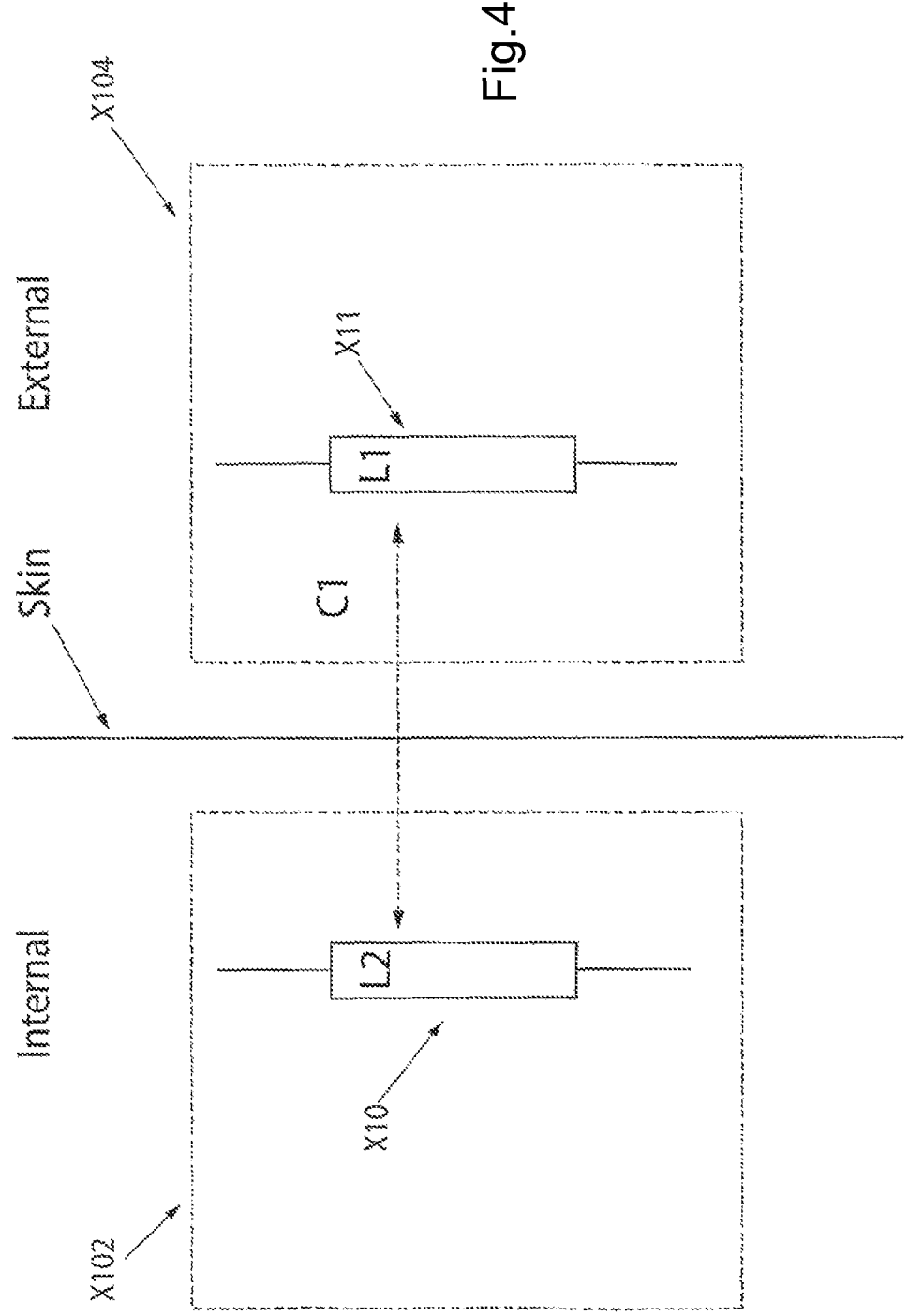
FIGS. 4-6 show circuit diagrams of parts of embodiments of a system of the invention.

As shown in FIG. 4, the external energy source X104 is equipped with a primary coil X11, L1, from which the external energy source X104 is arranged to transmit energy inductively to a first secondary coil X10, L2, in the internal energy receiver X102.

According to the invention, the system is arranged to determine by measurements one or more parameters related to a first coupling factor, shown as C1 in FIG. 4, between the primary coil X11 and the first secondary coil X10.

The external energy source X104 is adapted to transmit a first amount of energy to the energy receiver X102 in order to enable the medical device X100 to detect information related to the first coupling factor, such information including the coupling factor itself or other electrical parameters such as the voltage across the primary coil or the current through the primary coil or the energy or power levels transmitted by the external energy source. The energy transmitted, or the power level transmitted, are suitably measured by means of a circuit which integrates in order to obtain the energy, or derivates the energy transmitted in order to obtain the power level. An example of an integrating component is a capacitor, and a component for derivation could, for example, be an inductor.

According to the invention, the medical device X100 is adapted to wirelessly send feedback information, as exemplified above, related to the first coupling factor C1 to the external energy source X104, and the external energy source X104 is arranged to receive such feedback information from the medical device X100 and to perform a predetermined action based on said feedback information. The system may be adapted to let the measured feedback information be calculated either by integration or by a derivative.

Examples of the predetermined action comprise optimizing the placement of the primary coil X11 relative to the first secondary coil X10 in order to optimize the first coupling factor C1, or adjusting the placement of the primary coil relative to the first secondary coil. Other examples of such actions include adjusting the level of the transmitted energy amount or power level or adjusting current or voltage levels through/over the primary coil X11, or adjusting the pulse width in pulses through the external coil or adjusting a pulse train through it.

In one embodiment, the system of the invention is adapted to use the first coupling factor C1 in order to determine a second amount of energy to be transmitted by the external energy source X104 to the internal energy receiver X102, the second amount of energy being optimized to power or charge the medical device X100. In order to facilitate the determining of a second amount of energy, the medical device X100 can suitably comprise a control unit X108, as shown in FIG. 1.

In one embodiment, the system is adapted to increase the first amount of energy until said first coupling factor is detected by the system. This is useful if, for example, it is desired to locate the medical device X100. The system can then increase the energy transmitted until the coupling factor is detected, and thereby implicitly the medical device as such.

To this end, there can in one embodiment be comprised an indicator in the external energy source in order to indicate a level of the first coupling factor. The external energy source can then be moved over an area of the patient's body where the implant is thought to be located, and the energy is increased until the implant is located by means of the coupling factor being detected.

In one embodiment, there can further be comprised an indicator in the external energy source for indicating an optimal placement of the primary coil X11 in relation to the first secondary coil X10 in order to optimize the first coupling factor C1.

Figure 5:
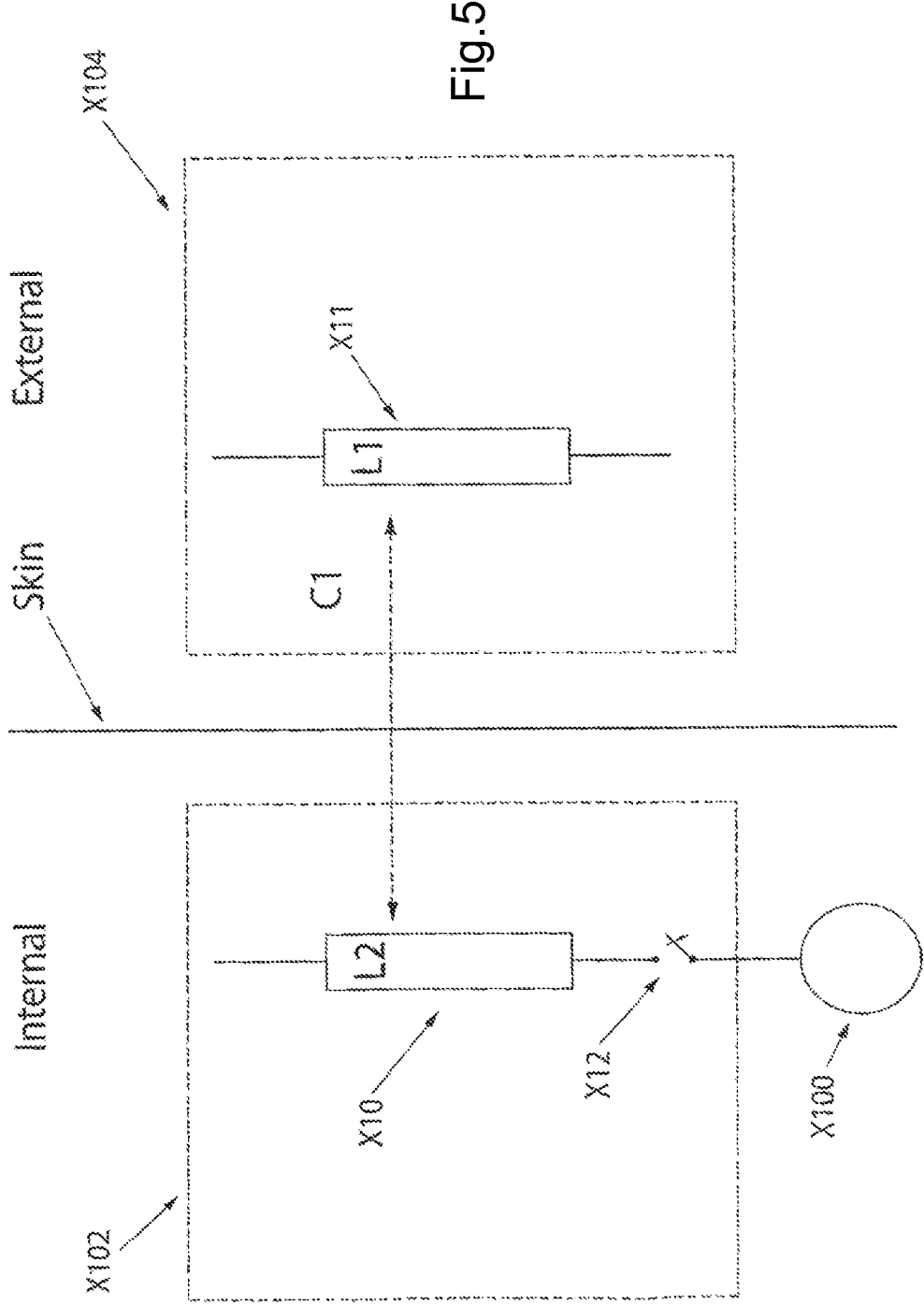

Measuring the coupling factor C1 and parameters related to it may be difficult when the first secondary coil X10 is connected to the rest of the implanted device X100. To this end, in one embodiment, as indicated in FIG. 5, the energy receiver X102 comprises a first switch X102a for switching a connection between the first secondary coil X10 and the rest of the medical implant X100 on and off, in order to enable the system to measure the first coupling factor C1 when the connection is off. The control of the first switch X102a is suitably carried out by an implantable control unit, such as, for example, the control unit X108. The implantable control unit X108 is suitably comprised in the medical device X100, although it can also be a separate implantable unit.

In a preferred embodiment, the first switch X102a is an electronic switch.

Figure 6:
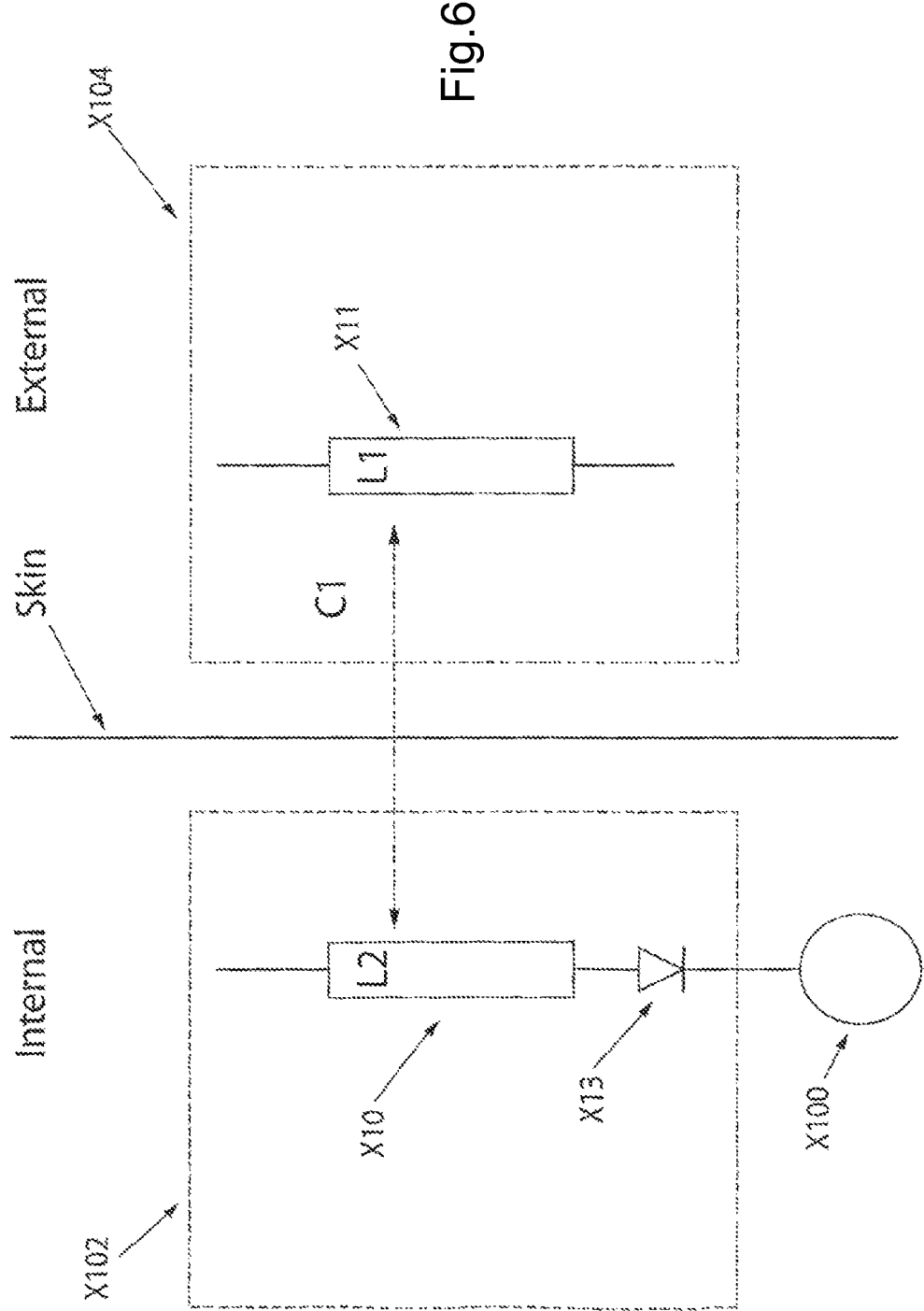

Due to the above mentioned difficulties of measuring parameters related to the coupling factor C1 when the first secondary coil X10 conducts electrical current, in one embodiment, as shown in FIG. 6, the internal energy receiver X102 comprises an electronic component X102b connected to the first secondary coil X10 for preventing the flow of electrical current between the first secondary coil X10 and the medical implant X100 during measurement of parameters related to the first coupling factor C1. As shown in FIG. 6, the electronic component is suitably a diode, the biasing of which is controlled from the control unit X108 in order to control when the diode conducts electricity and not, i.e. a "switching on and off" of a connection between the first secondary coil X10 and the medical implant X100.

In one embodiment, the system of the invention is adapted to let the first secondary coil X10 be substantially without electrical load or to have a high impedance load when measuring the first coupling factor. A high impedance load will naturally lead to a low current through the first secondary coil X10, so that the current will be at a low level, and will thus not interfere noticeably with the measurements. The phrase "high impedance load" is here used as signifying an impedance load which is above a predefined threshold which will lead to a current below a certain level through the first secondary coil.

Figure 7:
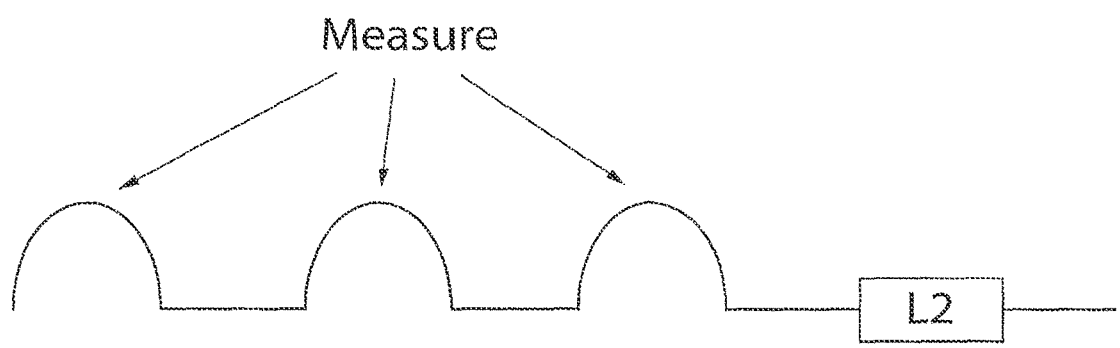
FIG. 7 shows a principle used in one embodiment of the invention.

In one embodiment, as indicated in FIG. 7, in order to facilitate the system's measurements of parameters related to the coupling factor, the energy receiver X102 comprises a half wave rectifying component for rectifying half of the pulse cycle of a received alternating current energy signal in the energy receiver, and the system is adapted to measure the parameters related to the first coupling factor during at least part of the non-rectified half of one or more pulse cycles.

In one embodiment, the system of the invention is also arranged to directly or indirectly measure over a predetermined period of time the difference between an electrical parameter related to the energy transmitted by the external energy source X104 and an electrical parameter related to the amount of energy received by the internal energy receiver X102, and to also determine the balance between these electrical parameters in order to determine the first coupling factor C1 or a parameter related to it. Examples of the electrical parameters which a difference is measured between can include the voltage over one or both coils, the current through one or both coils and the energy transmitted and received or the power level which is transmitted or received In one embodiment, the system of the invention comprises a memory unit, preferably adapted to be implanted, for storing information related to the first coupling factor.

Figure 8:
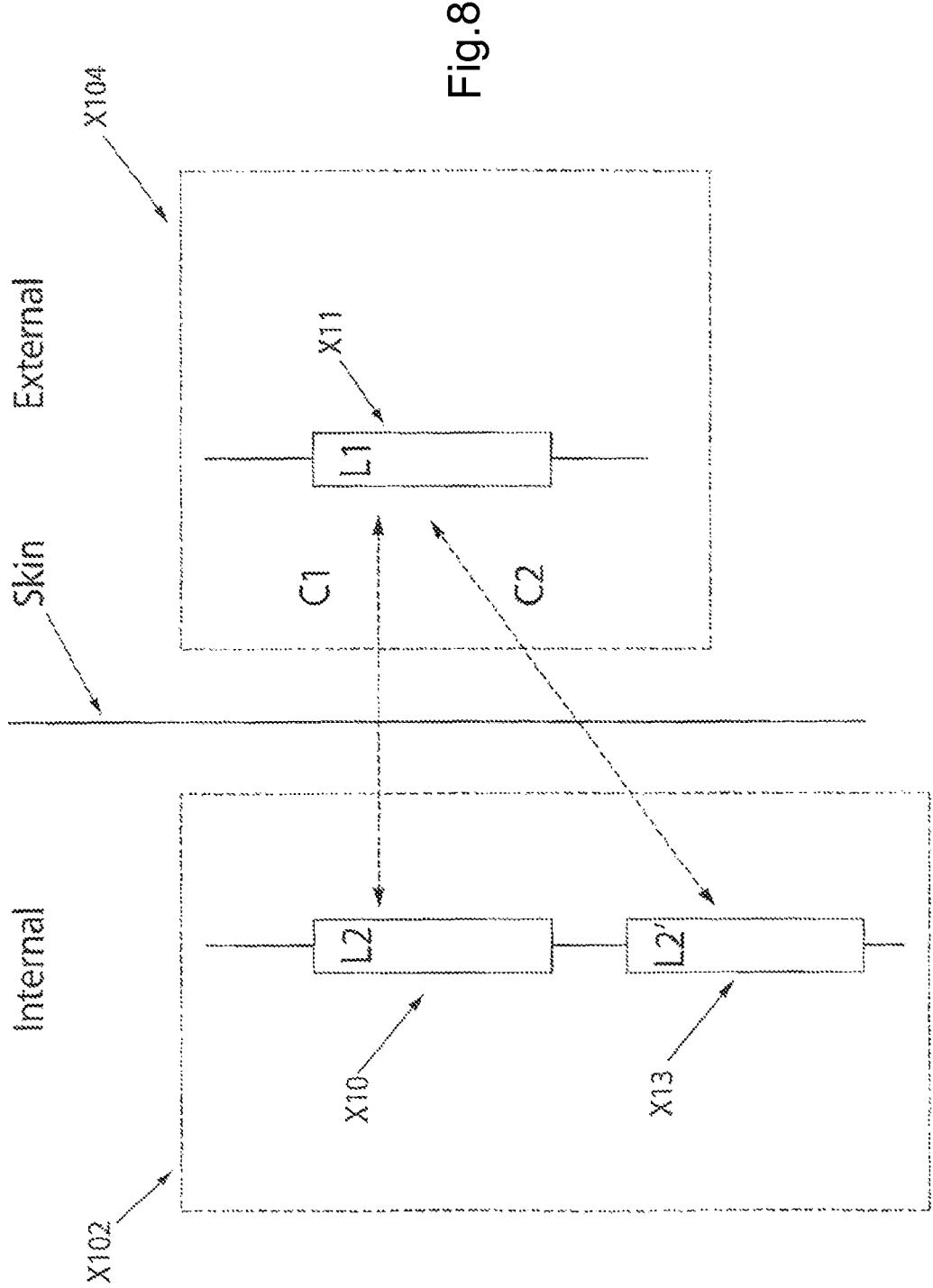
FIGS. 8 and 9 show alternative embodiments of a system of the invention.

In a further embodiment of the invention, shown symbolically in FIG. 8, the system further comprises a second secondary coil X13. Thus, in this embodiment, the primary coil X11 has the first coupling factor C1 in relation to the first secondary coil X10 and a second coupling factor C2 in relation to the second secondary coil X13.

In this embodiment, the first secondary coil X10 is arranged to receive energy for powering the medical device X100 and the second secondary coil X13 is adapted to supply information related to the second coupling factor C2. Since the second coupling factor C2 will have a predetermined relation to the first coupling factor C1, the one or more parameters related to the first coupling factor which are determined by measurements in the system can also be parameters which are related to the second coupling factor C2.

Thus, the system is in the embodiment of FIG. 8 arranged to determine by measurements the second coupling factor C2, and the feedback information mentioned in connection to the description of FIGS. 1 and 8 which is related to the first coupling factor C1 and which is transmitted to the external energy source X104 is information which is also related to the second coupling factor C2. Examples of such information include voltages across one or more coils, the current through one or more coils and energy transmitted and/or received and the power level transmitted or received In the embodiment shown in FIG. 8, the feedback information which is related to the first coupling factor C1 is information which is related to the second coupling factor C2, since these two coupling factors have a known relationship to each other. The system is adapted to use the feedback information in order to perform the action mentioned previously in order to optimize the placement of the primary coil X11 in relation to the second secondary coil X13 in order to optimize the second coupling factor C2, thereby also optimizing said first coupling factor C1.

In the embodiment shown in FIG. 8, the system of the invention is adapted to transmit a predetermined amount of energy from the external energy source X104 related to the second coupling factor, with the energy amount being optimized to charge or to initially operate the medical device X100.

In similarity to the "one coil embodiment", in the "two coil embodiment", the energy receiver X102 comprises an electronic component connected to the second secondary coil X13 for preventing or substantially reducing the flow of electrical current between the second secondary coil X13 and the medical implant X100 during the measurements of parameters related to the second coupling factor C2. In further similarity to the "one coil embodiment", in the "two coil embodiment", the electronic component is preferably a diode.

Figure 9:
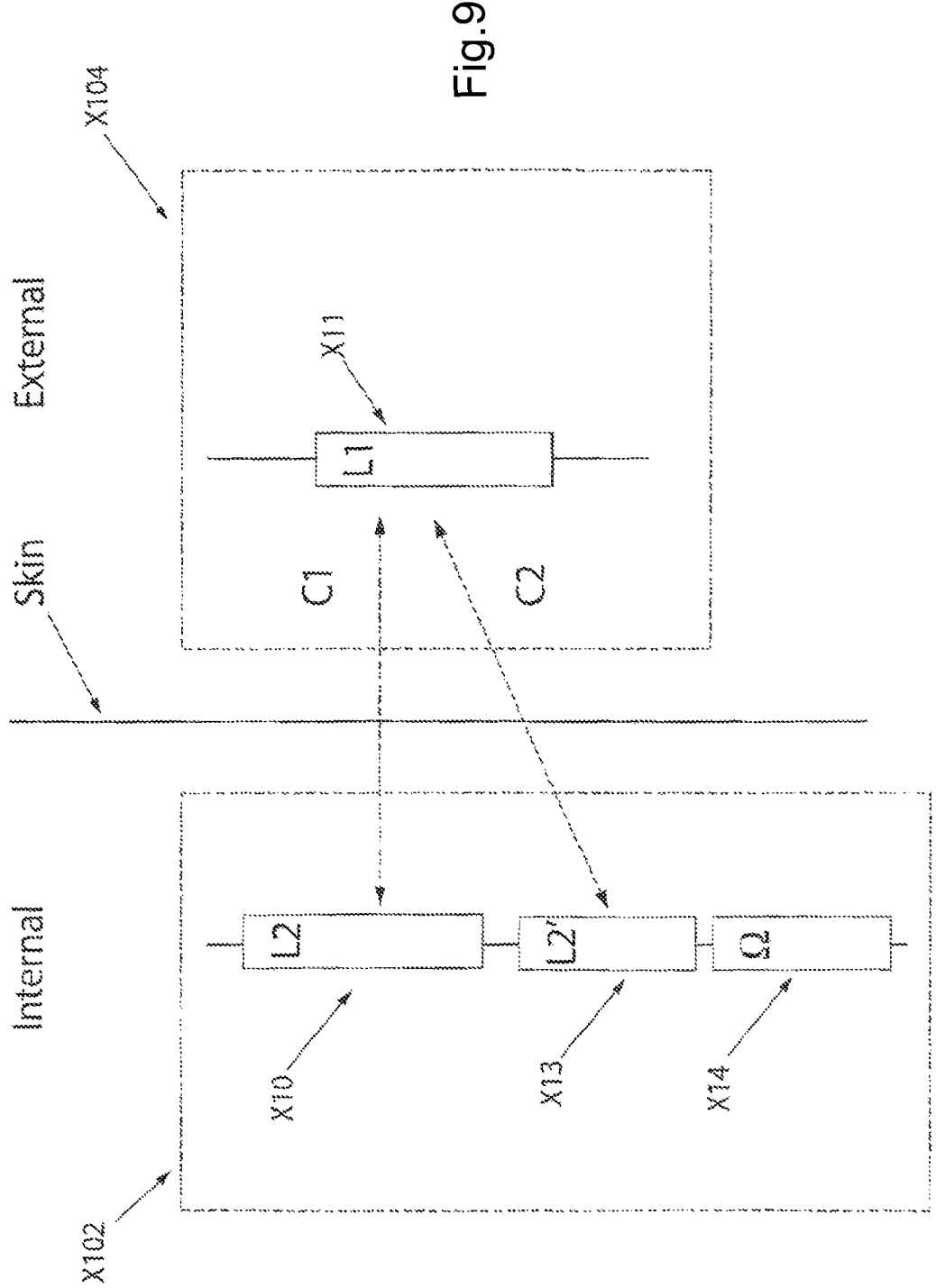

In further similarity to the "one coil embodiment", in the "two coil embodiment", the system is adapted to let the second secondary coil X13 be substantially without an electrical load or with a load with a high impedance, i.e. above a first threshold when measuring parameters related to the second coupling factor. Such impedance is shown symbolically in FIG. 9 under reference number X14. The phrase "high impedance load" is here used as signifying an impedance load which is above a predefined threshold which will lead to a current below a certain level through the first secondary coil.

Suitably, the second secondary coil X13 has an inductance L2' which is smaller than the inductance of the first secondary coil by a predetermined amount and is adapted primarily to supply information about said second coupling factor.

In one embodiment, the system of the invention also comprises a control unit to calculate said second coupling factor C2, suitably the control unit X108 shown in FIG. 1, or the external control unit X106 of the external energy source X104.

In one embodiment of the system of the invention, the external energy source X104 further comprises an electronic circuit for comparing the feedback information with the amount of energy transmitted by the external energy source.

Suitably, the electronic circuit comprises an analyzer unit adapted to analyze the amount of energy being transmitted and also being adapted to receive feedback information related to the amount of energy received in the receiver. It is also adapted to determine an energy balance by comparing the amount of transmitted energy and the feedback information to calculate said second coupling factor.

In one embodiment, the external energy source is adapted to use the feedback information to calibrate the level of transmitted energy, and in one embodiment, the external energy source is adapted to use the feedback information to optimise the placement of the primary coil X11 in relation to the first secondary coil X10 to maximize the first coupling factor C1.

In one embodiment of the "two coil embodiment", the medical device X100 comprises an internal control unit, which can be the previously mentioned control unit X108, which is arranged to receive information related to one of the first or second coupling factors from the external energy source X104 and which is adapted to receive measured information within the medical device X100 related to the same one of the first or second coupling factors. The internal control unit is also arranged to calculate feedback information based on the received and measured information, the feedback information then being transmitted from the internal control unit, and comprising information on one of the first or second coupling factors.

In one embodiment, the internal control unit further comprises an electronic circuit for comparing received information from the external energy source related to the amount of energy transmitted by the external energy source X104 and measured information related to the amount of energy received by the internal energy receiver X102.

Suitably, the electronic circuit comprises an analyzer which is adapted to analyze the amount of energy being received in the energy receiver X104X102 and is also arranged to receive feedback information related to the amount of energy being transmitted in the external energy source X104, and is furthermore adapted to determine an energy balance by comparing the amount of transmitted energy and received energy and to use this in order to calculate the first C1 or second C2 coupling factor.

In one embodiment, the external energy source X104 is adapted to use said feedback information to calibrate the level of transmitted energy.

In one embodiment, the external energy source X104 is adapted to use the feedback information to optimize the placement of the primary coil X11 in relation to the first secondary coil X10 for optimizing the energy supply in the energy receiver X102.

Thus, in respective embodiments, the "one" or "two coil" embodiments will further comprise the internal control unit X108, which is adapted to determine an energy balance between the energy received by the energy receiver X102 and the energy used by the medical device X104X100, with the feedback information relating to said determined energy balance, and an external control unit X106 which is adapted to calibrate the transmission of wireless energy from the energy source based on the determined energy balance and by using said feedback information.

In one embodiment, the system of the "one" or "two coil" embodiments will further comprise an internal control unit adapted to determine an energy balance between the energy received by the energy receiver X104X102 and the energy used by the medical device X100, with the feedback control information relating to said determined energy balance, and an external control unit X106 which is adapted to optimize the placement of the primary coil X11 in relation to the first secondary coil X10 based on the determined energy balance and arranged to use said feedback control information to optimize the energy received in the energy receiver X104X102.

Suitably, the system will further comprise at least one energy stabilizing unit in the medical device X100 in order to stabilize the received energy prior to use by the medical device X100. Preferably, the energy stabilizing unit comprises a capacitor.

In one embodiment, the system comprises an internal energy storage device for storing energy during said energy transfer, for use by the medical device X100. In one embodiment, the system is further arranged to both use transferred energy to power the medical device X100 and to store transferred energy in the internal energy storage device.

Also, transmission of information etc between the internal components and the external components of the system is suitably by means of such wireless technologies as radio etc.

Some further embodiments and their advantages will now be described:

Briefly described, wireless energy is transmitted from an external energy source located outside a patient and is received by an internal energy receiver located inside the patient. The internal energy receiver is connected to an electrically operable medical device implanted in the patient, for directly or indirectly supplying received energy to the medical device. An energy balance is determined between the energy sent by the external energy source and the energy received by the internal energy receiver, and the transmission of wireless energy is then controlled based on the determined energy balance. The energy balance thus provides an accurate indication of the correct amount of energy needed, which is sufficient to operate the medical device properly, but without causing undue temperature rise.

In FIG. 1, an arrangement is schematically illustrated for supplying an accurate amount of energy to an electrically operable medical device X100 implanted in a patient, whose skin is indicated by a vertical line S separating the interior "Int" of the patient from the exterior "Ext". The medical device X100 is connected to an internal energy receiver X102, likewise located inside the patient, preferably just beneath the skin S. Generally speaking, the energy receiver X102 may be placed in the abdomen, thorax, muscle fascia (e.g. in the abdominal wall), subcutaneously, or at any other suitable location. The energy receiver X102 is adapted to receive wireless energy E transmitted from an external energy source X104 located outside the skin S in the vicinity of the energy receiver X102.

As is well-known in the art, the wireless energy E may generally be transferred by means of any suitable TET-device, such as a device including a primary coil arranged in the energy source X104 and an adjacent secondary coil arranged in the energy receiver X102. When an electric current is fed through the primary coil, energy in the form of a voltage is induced in the secondary coil which can be used to operate a medical device, e.g. after storing the incoming energy in an energy storing device or accumulator, such as a battery or a capacitor. However, the present invention is generally not limited to any particular energy transfer technique, TET-devices or energy storing devices, and any kind of wireless energy may be used.

The amount of transferred energy can be regulated by means of an external control unit X106 controlling the energy source X104 based on the determined energy balance, as described above. Information representing the amount of energy received by the energy receiver X102 is sent from the energy receiver X102 to the external control unit X106 by means of the internal signal transmitter X110. Likewise, the energy source X104 sends information representing the amount of energy sent to the external control unit X106. In order to transfer the correct amount of energy, the energy balance and the required amount of energy can be determined by the external control unit by means of subtracting the amount of energy received from the amount of energy sent. Furthermore, an energy storing device or accumulator, not shown here, may also be connected to the energy receiver X102 for accumulating received energy for later use by the medical device X100. Alternatively or additionally, characteristics of such an energy storing device, also reflecting the required amount of energy, may be measured as well. The energy storing device may be a battery, and the measured characteristics may be related to the current state of the battery, such as voltage, temperature, etc. In order to provide sufficient voltage and current to the medical device X100, and also to avoid excessive heating, it is clearly understood that the battery should be charged optimally by receiving a correct amount of energy from the energy receiver X102, i.e. not too little or too much. The energy storing device may also be a capacitor with corresponding characteristics.

For example, battery characteristics may be measured on a regular basis to determine the current state of the battery, which then may be stored as state information in a suitable storage means in the internal control unit X108. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit X106X108 is adapted to determine the energy balance and/or the currently required amount of energy, (either energy per time unit or accumulated energy) based on measurements made by the above-mentioned sensors. The internal control unit X108 is further connected to an internal signal transmitter X110, arranged to transmit a control signal S reflecting the received amount of energy, to an external signal receiver X112 connected to the external control unit X106. The external control unit X106 then calculates the energy balance by subtracting the amount of energy received from the amount of energy transmitted. The amount of energy transmitted from the energy source X104 may then be regulated in response to the received control signal.

Hence, the present solution employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by the medical device. The medical device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the medical device.

The internal signal transmitter X110 and the external signal receiver X112 may be implemented as separate units using suitable signal transfer means, such as radio, IR (Infrared) or ultrasonic signals. Alternatively, the signal transmitter X110 and the external signal receiver X112 may be integrated in the internal energy receiver X102 and the energy source X104, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 1 may operate basically in the following manner. The energy balance is first determined by the external control unit X106. The external control unit X106 then uses this information to control the energy source X104. Alternatively, the energy balance can be determined by the internal control unit X108 instead depending on the implementation. This process may be repeated intermittently at certain intervals during ongoing energy transfer, or may be executed on a more or less continuous basis during the energy transfer.

The amount of transferred energy can generally be regulated by adjusting various transmission parameters in the energy source X104, such as voltage, current, amplitude, wave frequency and pulse characteristics.

Figure 2:
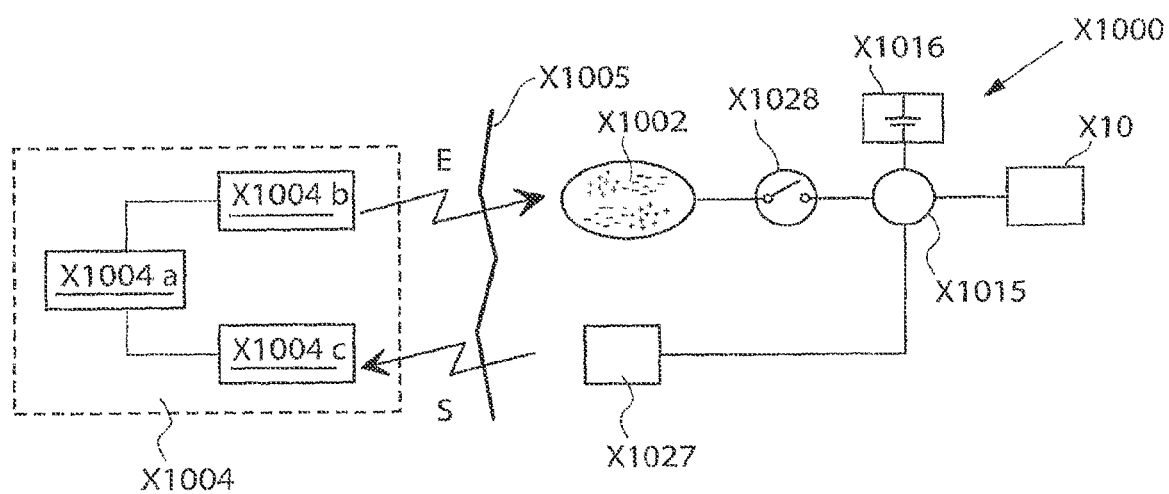
FIG. 2 is a more detailed block diagram of an apparatus for controlling transmission of wireless energy supplied to an electrically operable medical device implanted in a patient.

FIG. 2 Schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver X1002 connected to implanted energy consuming components of the medical device X100. Such an energy receiver X1002 may include an energy source and/or an energy-transforming device. Briefly described, wireless energy is transmitted from an external energy source X1004a located outside the patient and is received by the internal energy receiver X1002 located inside the patient. The internal energy receiver is adapted to directly or indirectly supply received energy to the energy consuming components of the medical device X100 via a second switch X1028. An energy balance is determined between the energy received by the internal energy receiver X1002 and the energy used for the medical device X100, and the transmission of wireless energy is then controlled based on the determined energy balance. The energy balance thus provides an accurate indication of the correct amount of energy needed, which is sufficient to operate the medical device X100 properly, but without causing undue temperature rise.

In FIG. 2 the patient's skin is indicated by a vertical line X1005. Here, the energy receiver comprises an energy-transforming device X1002 located inside the patient, preferably just beneath the patient's skin X1005. Generally speaking, the implanted energy-transforming device X1002 may be placed in the abdomen, thorax, muscle fascia (e.g. in the abdominal wall), subcutaneously, or at any other suitable location. The implanted energy-transforming device X1002 is adapted to receive wireless energy E transmitted from the external energy source X1004a provided in an external energy-transmission device X1004 located outside the patient's skin X1005 in the vicinity of the implanted energy-transforming device X1002.

As is well known in the art, the wireless energy E may generally be transferred by means of any suitable Transcutaneous Energy Transfer (TET) device, such as a device including a primary coil arranged in the external energy source X1004a and an adjacent secondary coil arranged in the implanted energy-transforming device X1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit X1004b that controls the external energy source X1004a based on the determined energy balance to regulate the amount of transferred energy. In order to transfer the correct amount of energy, the energy balance and the required amount of energy is determined by means of a determination device including an implanted internal control unit X1015 connected between the second switch X1028 and the medical device X100. The internal control unit X1015 may thus be arranged to receive various measurements obtained by suitable sensors or the like, not shown, measuring certain characteristics of the medical device X100, somehow reflecting the required amount of energy needed for proper operation of the medical device X100. Moreover, the current condition of the patient may also be detected by means of suitable measuring devices or sensors, in order to provide parameters reflecting the patient's condition. Hence, such characteristics and/or parameters may be related to the current state of the medical device X100, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator X1016 may optionally be connected to the implanted energy-transforming device X1002 via the internal control unit X1015 for accumulating received energy for later use by the medical device X100. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the medical device X100, and also to avoid excessive heating, it is clearly understood that the battery should be charged optimally by receiving a correct amount of energy from the implanted energy-transforming device X1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit X1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit X1015 of the determination device is adapted to determine the energy balance and/or the currently required amount of energy, (either energy per time unit or accumulated energy) based on measurements made by the above-mentioned sensors or measuring devices of the medical device X100, or the patient, or an implanted energy source if used, or any combination thereof. The internal control unit X1015 is further connected to an internal signal transmitter X1027, arranged to transmit a control signal reflecting the determined required amount of energy, to an external signal receiver X1004c connected to the external control unit X1004b. The amount of energy transmitted from the external energy source X1004a may then be regulated in response to the received control signal.

Alternatively, the determination device may include the external control unit X1004b. In this alternative, sensor measurements can be transmitted directly to the external control unit X1004b wherein the energy balance and/or the currently required amount of energy can be determined by the external control unit X1004b, thus integrating the above-described function of the internal control unit X1015 in the external control unit X1004b. In that case, the internal control unit X1015 can be omitted and the sensor measurements are supplied directly to the internal signal transmitter X1027 which sends the measurements over to the external signal receiver X1004c and the external control unit X1004b. The energy balance and the currently required amount of energy can then be determined by the external control unit X1004b based on those sensor measurements.

Hence, the present solution according to the arrangement of FIG. 2 employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter X1027 and the external signal receiver X1004c may be implemented as separate units using suitable signal transfer means, such as radio, IR (Infrared) or ultrasonic signals. Alternatively, the internal signal transmitter X1027 and the external signal receiver X1004c may be integrated in the implanted energy-transforming device X1002 and the external energy source X1004a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 2, the second switch X1028 is either separate and controlled by the internal control unit X1015, or integrated in the internal control unit X1015. It should be understood that the second switch X1028 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 2 may operate basically in the following manner. The energy balance is first determined by the internal control unit X1015 of the determination device. A control signal reflecting the required amount of energy is also created by the internal control unit X1015, and the control signal is transmitted from the internal signal transmitter X1027 to the external signal receiver X1004c. Alternatively, the energy balance can be determined by the external control unit X1004b instead depending on the implementation, as mentioned above. In that case, the control signal may carry measurement results from various sensors. The amount of energy emitted from the external energy source X1004a can then be regulated by the external control unit X1004b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source X1004a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 3:
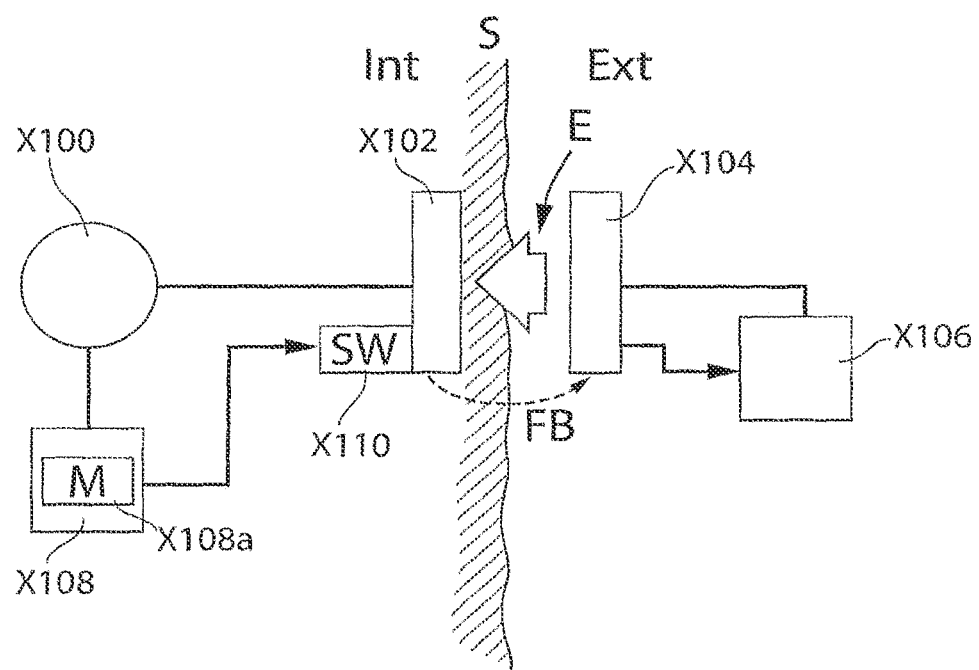
FIG. 3 is an alternative schematic block diagram illustrating an arrangement for supplying an accurate amount of energy to an electrically operable medical device.

In FIG. 3, an arrangement is schematically illustrated for supplying an accurate amount of energy to an electrically operable medical device X100 implanted in a patient, whose skin is indicated by a vertical line S separating the interior "Int" of the patient from the exterior "Ext". The medical device X100 is connected to an internal energy receiver X102, likewise located inside the patient, preferably just beneath the skin S. Generally speaking, the energy receiver X102 may be placed in the abdomen, thorax, muscle fascia (e.g. in the abdominal wall), subcutaneously, or at any other suitable location. The energy receiver X102 is adapted to receive wireless energy E transmitted from an external energy source X104 located outside the skin S in the vicinity of the energy receiver X102.

The wireless energy E is transferred by means of a primary coil arranged in the energy source X104 and an adjacent secondary coil arranged in the energy receiver X102. When an electric current is fed through the primary coil, energy in the form of a voltage is induced in the secondary coil which can be used to operate the medical device X100, e.g. after storing the incoming energy in an energy storing device or accumulator, such as a battery or a capacitor, not shown in this figure.

The internal energy receiver X102 is adapted to transfer suitable feedback control information FB from the secondary coil to the primary coil by switching the secondary coil on and off to induce a detectable impedance load variation in the primary coil. This load variation is created and controlled to encode the feedback control information in a useful manner. The feedback control information thus communicated from the energy receiver X102 over to the energy source X104, generally relates to the energy for operating the medical device X100. The feedback control information is then used for controlling the transmission of wireless energy from the external energy source X104. The amount of transferred energy is regulated by means of an external control unit X106 controlling the energy source X104.

An internal control unit X108 may be implanted in the patient connected to the medical device X100. The internal control unit X108 is used to control the on and off switching of the secondary coil. The feedback control information FB may include at least one predetermined parameter relating to the received energy. The predetermined parameter may further be variable. When using the internal control unit X108, the feedback control information may relate to the received energy and may also require artificial intelligence to be generated.

The on and off switching of the secondary coil may be executed by means of the implantable first switch X110X102a (SW) at the energy receiver X102, and the first switch X110X102a is connected to and controlled by the internal control unit X108. The switch may be an electronic switch such as a transistor. Further, the internal control unit X108 may comprise a memory X108a for storing the transferred feedback control information FB.

The energy balance mentioned above may be determined by means of the external control unit X106 or the internal control unit X108, and the feedback control information will then relate to the determined energy balance. In that case, the external control unit X106 may be used to control the transmission of wireless energy E from the external energy source X104 based on the determined energy balance and using the received feedback control information FB.

The internal control unit X108 may be arranged to receive various measurements obtained by suitable sensors or the like, not shown, measuring certain characteristics of the medical device X100, somehow reflecting the energy needed for proper operation of the medical device X100. Moreover, the current condition of the patient may also be detected by means of suitable measuring devices or sensors, in order to provide parameters reflecting the patient's condition. Hence, such characteristics and/or parameters may be related to the current state of the medical device X100, such as power consumption, operational mode and temperature, as well as the patient's condition reflected by, e.g., body temperature, blood pressure, heartbeats and breathing.

Furthermore, an energy storing device or accumulator, not shown here, may also be connected to the energy receiver X102 for accumulating received energy for later use by the medical device X100. Alternatively or additionally, characteristics of such an energy storing device, also relating to the energy, may be measured as well. The energy storing device may be a battery, and the measured characteristics may be related to the current state of the battery, such as voltage, temperature, etc. In order to provide sufficient voltage and current to the medical device X100, and also to avoid excessive heating, it is clearly understood that the battery should be charged optimally by receiving a correct amount of energy from the energy receiver X102, i.e. not too little or too much. The energy storing device may also be a capacitor with corresponding characteristics.

For example, battery characteristics may be measured on a regular basis to determine the current state of the battery, which then may be stored as state information in a suitable storage means in the internal control unit X108. Thus, whenever new measurements are made, the stored battery state information can be updated accordingly. In this way, the state of the battery can be "calibrated" by transferring a correct amount of energy, so as to maintain the battery in an optimal condition.

Alternatively, sensor measurements can be transmitted to the external control unit X106 wherein the energy balance and/or the currently required amount of energy can be determined by the external control unit X106, thus basically integrating the above-described function of the internal control unit X108 in the external control unit X106. In that case, the internal control unit X108 can be omitted and the sensor measurements are comprised in the feedback control information FB. The energy balance and the currently required amount of energy can then be determined by the external control unit X106 based on those sensor measurements.

Hence, the present solution employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by the medical device. The medical device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the medical device.

The feedback control information FB may further be modulated with respect to frequency, phase or amplitude.

To conclude, the energy supply arrangement illustrated in FIG. 1 may operate basically in the following manner, in the case when the transmission of wireless energy is controlled based on the energy balance described above. The energy balance may first be determined by the internal control unit X108. Feedback control information FB relating to the energy is also created by the internal control unit X108, and the feedback control information FB is transmitted from the energy receiver X102 to the energy source X104. Alternatively, the energy balance can be determined by the external control unit X106 instead depending on the implementation, as mentioned above. In that case, the feedback control information FB may carry measurement results from various sensors. The amount of energy emitted from the energy source X104 can then be regulated by the external control unit X106, based on the determined energy balance, e.g. in response to the received feedback control information FB. This process may be repeated intermittently at certain intervals during ongoing energy transfer, or may be executed on a more or less continuous basis during the energy transfer.

The amount of transferred energy can generally be regulated by adjusting various transmission parameters in the energy source X104, such as voltage, current, amplitude, wave frequency and pulse characteristics.

Figure 10:
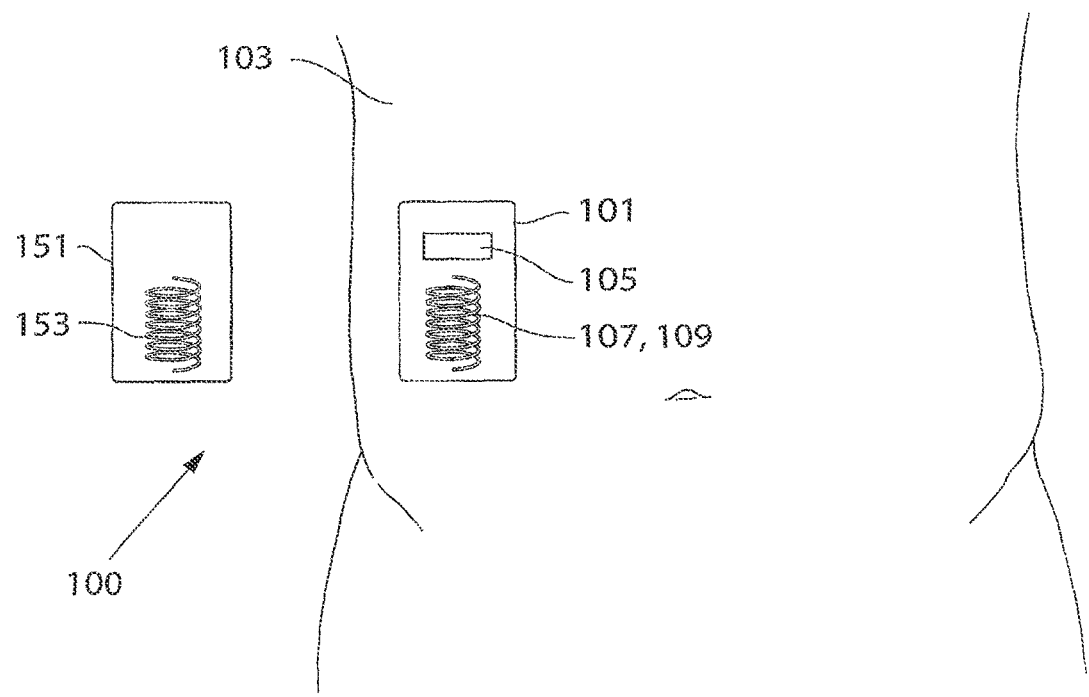
FIG. 10 is a general schematic view of an implanted device charger arrangement.

In FIG. 10 an arrangement 100 for charging a battery powered an implanted medical device 101 is shown. The implanted implantable medical device 101 implanted in a patient 103 can for example comprise a battery 105 that can be charged by includes or is connected to an internal power supply such as a charger 107. The charger can typically be a coil 109 adapted to be energized by an electromagnetic field formed by an external power supply in the form of an external charger device 151. The external charger device can typically comprise a coil 153 that is adapted to generate an electro magnetic field for energizing the coil 109 thereby enabling charging of the battery 105.104 containing or connected to an internal energy source. The internal energy source can for example comprise an energy accumulator such as an electrochemical cell or battery 105 or a capacitor, the energy accumulator generally also called "battery" herein. The energy source is rechargeable and can be charged by the internal power supply 104 such as by energy received from an internal charger 107 included in or connected to the internal power supply. The internal charger can typically include or be connected to a first coil 109 that is arranged to be influenced by an electromagnetic field created by an external power supply 150 containing or connected to an external charger 151. The external charger device can typically comprise or be connected to a second coil 153 that is arranged to generate an electromagnetic field for creating an electric current in the first coil 109, thereby allowing the charging of the battery 105. The first coil can be called an energy receiver and the second coil an energy transmitter.

In order provide an efficient and secure transfer of energy through the skin of the patient 103 it is may be important for a user of the external charger 151 to gain knowledge of the position of the implanted medical device 101 so that the electromagnetic field generated by the second coil 153 can be correctly controlled. Hence, an electromagnetic field for creating an electric current used for charging the battery 105 of the internal power supply 104 should be sufficiently strong in order to provide a short charging time of the battery. On the other hand the electromagnetic field should not be too strong which since a strong electromagnetic field could endanger the internal charger device 107 or cause other problems, such as causing problems to tissues of the patient's body 103.

In order to gain knowledge of the position of the implanted medical device 101 electromagnetic feedback information is used and in accordance with the present invention. particular of the first coil 109 feedback information can be used.

Figure 11:
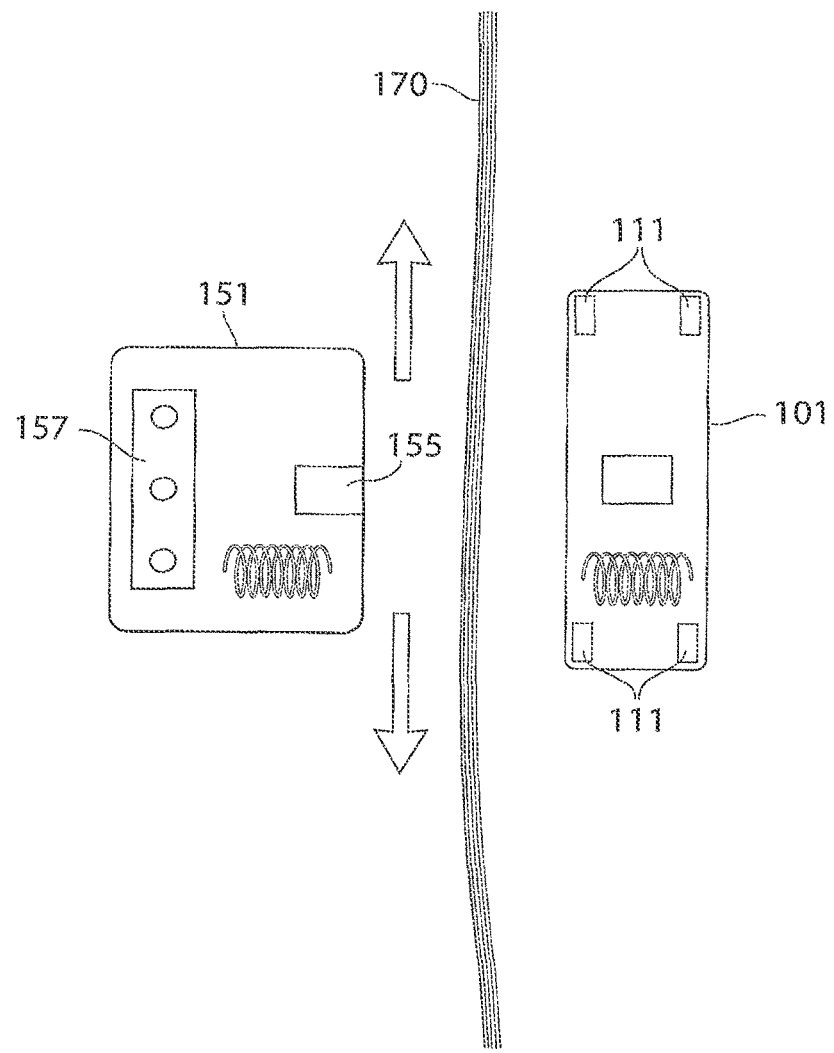
FIG. 11 is a schematic view of a charger arrangement in accordance with a first embodiment.
Figure 12:
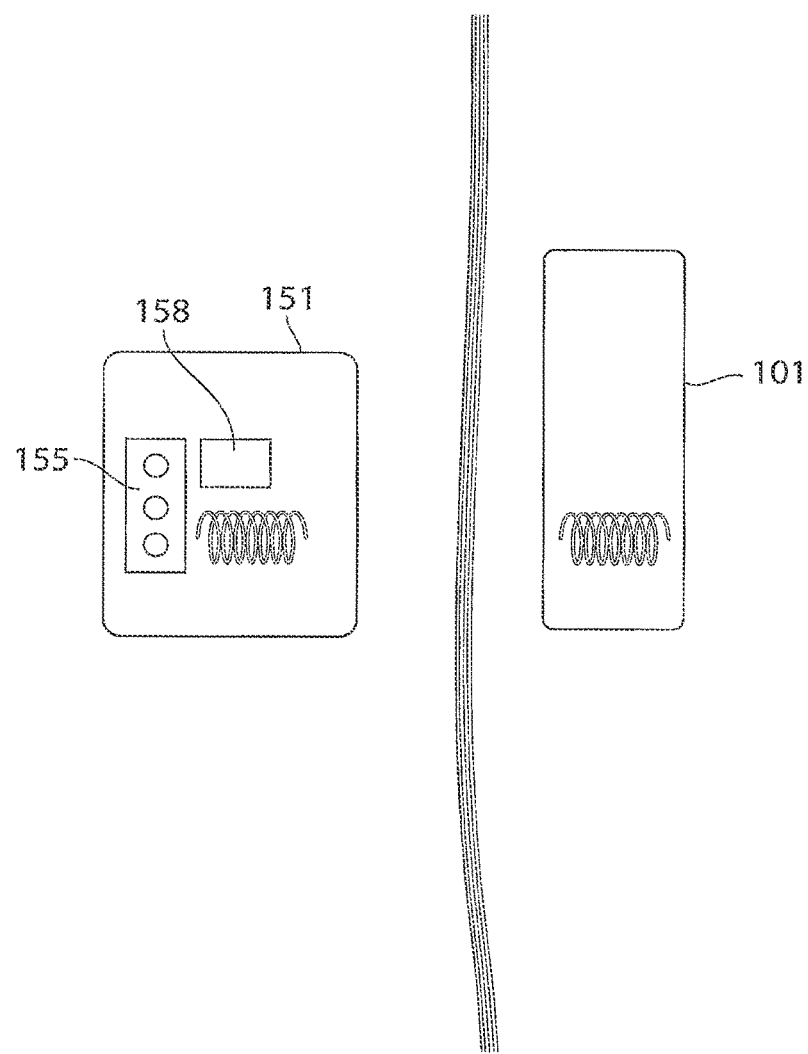
FIG. 12 is a schematic view of a charger arrangement in accordance with a second embodiment.

FIGS. 11 and 12 are schematics of two embodiments. In FIG. 11 a first embodiment of the present invention is shown. In accordance with the embodiment shown in FIG. 11 a seta plurality of Radio Frequency Identification (RFID) transmitters are provided in the internal charger 107 and/or in the external charger 151 for facilitating positioning of the implanted medical device. Using for example a triangulation algorithm the position of the implanted medical device can be calculated and feed back can be given to the user when the external charger is placed in the optimal position for charging the internal charger. In FIG. 11 the internal charger 101 is provided with a number of RFID transmitters 111 and the external charger is provided with a receiver 155 for receiving transmitted RFID signals and a display 157 for displaying the current position. In accordance with one embodiment the display is adapted to display the position relative to an optimal position. For example the display may comprise a number of LEDs indicating the current position. For example a red diode may be lit when the charger is far off from an optimal position. When the external charger is move closer to an optimal position a yellow diode can be lit and when the external charger is in or close to an optimal position a green diode can be lit. localizing of the implanted medical device and in particular localizing the first coil 109 thereof, i.e. for finding the position thereof in relation to the external, second coil 153.

In accordance with one embodiment the RFID signature is set in response to the magnitude of the received electro magnetic field. In such an embodiment only one RFID transmitter is required and the user can sweep over the skin 170 of the patient with a low charging power and find the position providing the optimal charging conditions and then tune the charging to an optimal power level.

In FIG. 12, another embodiment of the present invention is shown. In accordance with the embodiment shown in FIG. 12 the external charger and or internal charger is/are adapted to measure the mutual coupling between the external charger and internal charger using a coupling measurement device 158. Based on feedback from the coupling measurement device a user can sweep over the skin of the patient with a low charging power and find the position as the position where the coupling measurement device indicates the highest coupling factor. After finding the optimal position providing the optimal charging conditions the user can then tune the charging to an optimal power level for charging the battery of the implanted medical device.

The coupling measurement device is in accordance with one embodiment adapted to analyze the amount of energy being transmitted and adapted to receive feed back information about the amount of energy received in the receiver. By calculating the ratio between the transmitted amount of energy and the received amount of energy the coupling factor can be determined.

In another embodiment of the present invention a power switch is provided in the internal charger for switching on and off the connection between the implanted medical device and the coil for receiving energy from the external charger. The internal charger is then further provided with a transmitter for transmitting information related to the charging received in the internal charger as an impedance variation in the coil load, when said switch switches the coil on and off.

In one embodiment of the present invention, a receiver in the external power supply for receiving passively transmitted feed back information from the first coil generated by a power pulse or burst transmitted by the external power supply. In such an embodiment the external charger can be provided with a receiver for detect a magnetic field caused by the internal charger as a response to the power burst or pulse. By determining the strength of the magnetic field the external charger can determine if the position becomes better or worse when a user moves the charger over the skin of a patient having an implanted medical device associated with an internal charger. An increase in the response magnetic field indicates a better energy supply position.

The external power supply may also comprise an analyzer adapted to analyze the feedback information from the internal charger such as the amount of electromagnetic field detected and display this information. Using the displayed information the user is able to optimize the placement of the external charger in relation to the internal charger to optimize said energy transfer to said internal power supply Further in order to initiate a procedure to find an optimal position for charging the internal charger the external charger can be adapted to perform a calibration sequence. For example in order to generate a feedback from the internal charger the external charger can be adapted to slowly increase the energy transmitter until a feedback signal is received from the internal charger. When a response is received from the internal charger the user can start moving the external charger for finding the optimal charging position based on the feedback information from the internal charger.

Figure 13A:
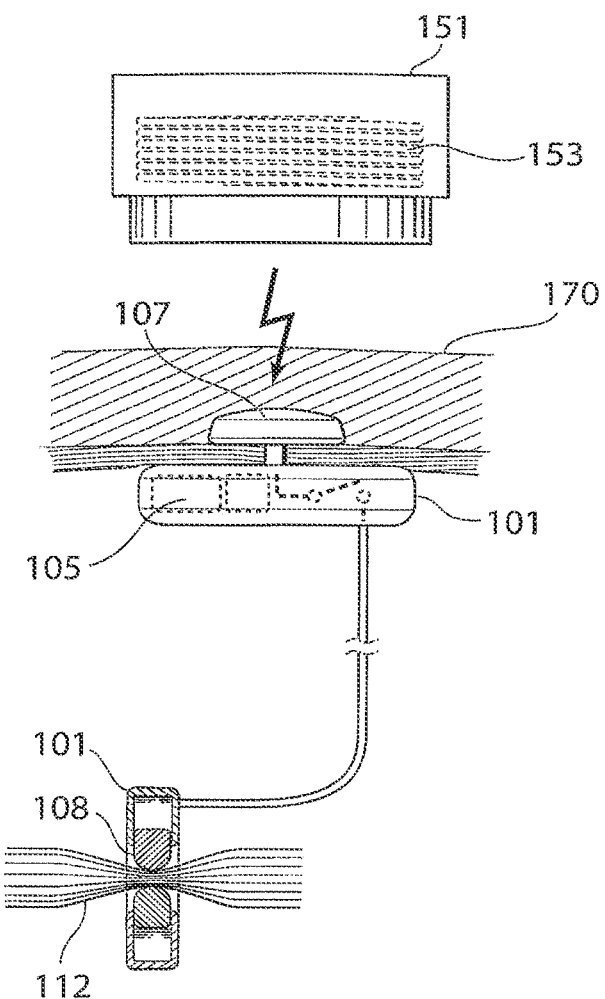
FIGS. 13a and 13b are schematic views of a chargeable medical device.

In FIG. 13a another view of a chargeable medical device 101 is depicted. The device 101 comprises an internal charger 107 implanted in a patient. The internal charger 107 is adapted to receive wireless energy from an external charger 151 through the skin 170 of the patient in accordance with the above. The internal charger is connected to an internal energy supply such as a battery 105. The internal energy supply supplies energy used for driving an implanted medical device 101. The implanted medical device 101 can be operated using a mechanically or hydraulically controlled control device. For example the implanted medical device can be adapted to mechanically or hydraulically adjust a member 108 located in conjunction with a blood vessel 112 or some other internal organ 112 for controlling the flow in the vessel or organ 112. In FIG. 13a the member 108 is mechanically or hydraulically adjusted to a generally closed position.

Figure 13B:
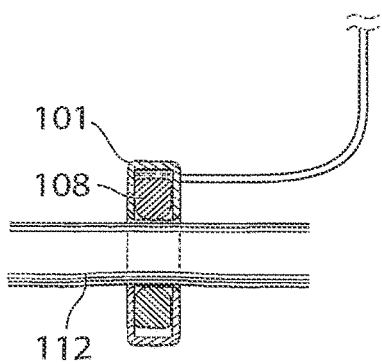

In FIG. 13b another view of the chargeable medical device 101 is depicted. The view in FIG. 13b corresponds the view in FIG. 13a but with the member 108 mechanically or hydraulically adjusted to a generally open position.

Figure 14:
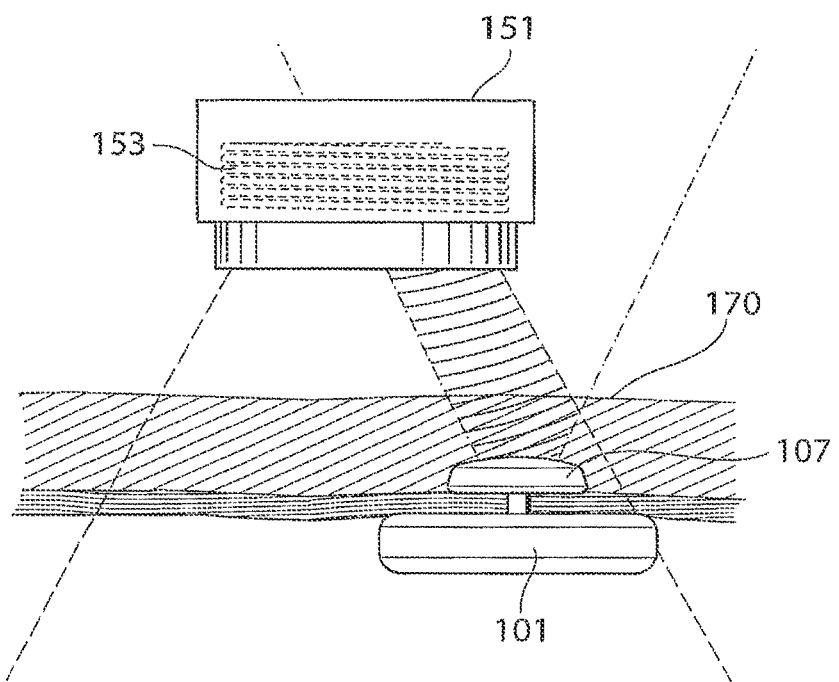
FIG. 14 is a schematic view illustrating the operation of a charger system.

In FIG. 14 a view further illustrating the operation of a charger system as described herein. Hence in order to find an optimal position of the external charger 151 for transferring energy to the internal charger 107, the external charger 151 is moved of the skin of the patient. In response to feedback information from the implanted medical device the optimal position for charging the implanted medical device is selected. The operation is further described below in conjunction with FIG. 15.

Figure 15:
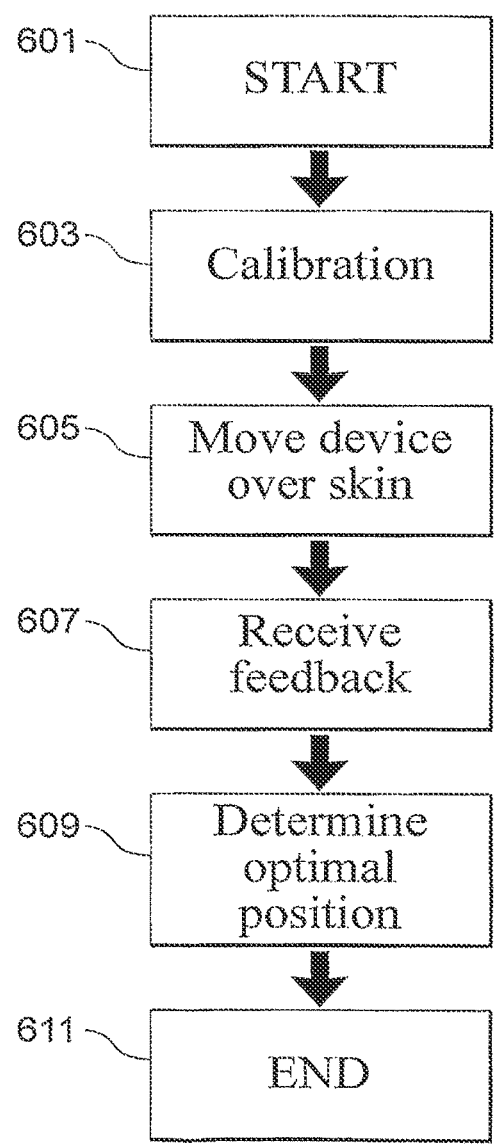
FIG. 15 is a flowchart illustrating the operation of a charger system.

In FIG. 15 a flow chart illustrating steps performed when using the system as described herein in order to find an optimal position for charging an internal charger for supplying power to an implanted medical device. First in a step 601 the external charger is turned on. Next in a step 603 the charger runs through a calibration procedure for producing a response from the internal charger. Next in a step 605 the user starts to move the external charger over the skin of the patient. Thereupon, in a step 607, the user receives feedback information from the system enabling the user to move the external charger to a more favorable position. Upon finding an optimal position the charger indicates that in a step 609 and the procedure ends in a step 611.

Figure 16:
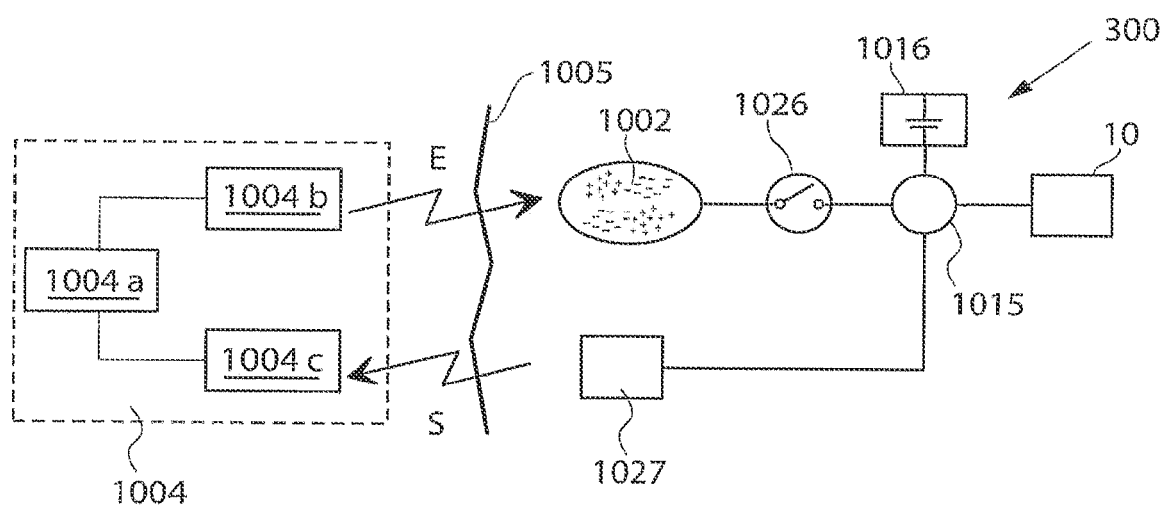
FIG. 16 is a schematic view of an implanted chargeable medical device.

In FIG. 16 another view of an implanted chargeable medical device 300 is depicted. Here, the patient's skin is indicated by a vertical line 1005. Here, the internal charger in the form of an energy receiver comprises an energy-transforming device 1002 located inside the patient. The energy receiver such as a coil can preferably be located just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from an external energy-source 1004a, in particular an external charger such as a coil provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between a switch 1026 and an implanted medical device 10. The internal control unit 1015 may thus be arranged to receive various measurements obtained by suitable sensors or the like, not shown, measuring certain characteristics of the implanted medical device 10, somehow reflecting the required amount of energy needed for proper operation of the implanted medical device 10. Moreover, the current condition of the patient may also be detected by means of suitable measuring devices or sensors, in order to provide parameters reflecting the patient's condition. Hence, such characteristics and/or parameters may be related to the current state of the implanted medical device, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the implanted medical device. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the implanted medical device 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the implantable medical device 10, or the patient, or an implanted energy source if used, or any combination thereof.

The internal control unit 1015 can further be connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to an external signal receiver 1004c and the external control unit 1004b. The energy balance and the currently required amount of energy can then be determined by the external control unit 1004b based on those sensor measurements.

Hence, the system in accordance with the arrangement depicted in FIG. 16 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004c Generally RFID is a method of remotely storing and retrieving identification data. For RFID devices called RFID tags are often used. An RFID tag is a relatively small object that can easily be attached to or incorporated into any product. An RFID tag contains an antenna to allow it to receive and respond to radio-frequency queries from an RFID transceiver. RFID tags can be either active or passive. RFID tags can be passive and then they have no own power supply. The small electrical current induced in the antenna by the incoming radio-frequency wave provides power for the tag to send a response containing an identification of the tag such as an ID number. Active RFID tags have own power sources and may have longer ranges and larger memories than passive tags as well as the capability of storing additional information sent by the transceiver. For example, in the case where passive RFID devices are used, an optimal position of the external charger in relation to the internal charger can be found also in cases where the implanted device has totally been emptied of energy and the position of the implanted device and in particular of the internal charger is not known to the user or operator such as when a patient receives care in a foreign hospital.

In the embodiment of FIG. 11a the RFID transmitters 111 are located in the internal charger 107, in a symmetrical position around the internal coil 109. For example four RFID transmitters can be arranged which then can arranged in the corners of a square. The external charger 151 is provided with a transceiver 155, also called interrogator or RFID receiver, for issuing interrogating signals and receiving transmitted RFID signals in response thereto. The transceiver 155 should be located centrally in relation to the external coil 151 such as just in front of it or behind seen in a direction centrally through the external coil and perpendicularly to the surface of the external charger that is facing the skin of the patient and arranged to be in contact therewith, a suitable position indicated by the dashed lines at 155' in FIG. 11a.

Different methods may be used for determining or estimating the position of the external coil—strictly the position of the transceiver—in relation to the internal coil 109—strictly the position of the RFID transmitters 111. In one method the RFID transmitters are arranged to respond selectively so that there is a specific interrogation signal for each transmitter. The transceiver 155 can then measure the length of the time period between interrogation signal and response. The measured lengths can be compared in an evaluation unit 166 which compares the lengths to each other and generates a signal according to the result of the comparing. In another method the RFID transmitters 111 are arranged to respond to the same interrogation signal but the transceiver 155 contains a plurality of antenna elements and the times when the signals from the RFID transmitters containing the identifications thereof are measured. The measured times are evaluated in the evaluation unit 166 to find the geometrical direction from the transceiver to the respective RFID transmitter. The directions are evaluated in relation to each other to find the relative position of the transceiver. This can be called a triangulation method.

In another embodiment the RFID signature is set in response to the magnitude of the received electromagnetic field as measured by a measurement unit 119 in the internal charger 107. A value of the magnitude can e.g. be obtained by measuring the voltage induced in the internal coil 109. Alternatively, the strength of the RF interrogating electromagnetic field can be sensed by the receiving RFID transmitter. Then, only one RFID transmitter 111 is required which should be placed symmetrically or centrally in relation to the internal coil 109. A suitable position of the single RFID transmitter is indicated by the dashed lines at 111' in FIG. 11a. In the same way as in other embodiments the user can sweep over or scan the skin 170 of the patient with a low charging power. The internal measurement unit 119 then determines, when receiving an interrogation signal from the transceiver 155, the strength of the received electromagnetic field and provides the determined value of the strength to the RFID transmitter. The RFID transmitter 111 sets its identification accordingly and thereafter transmits it to the transceiver.

In another simple embodiment also only one RFID transmitter 111 is used which when interrogated responds with a signal holding its information. The transceiver 155 can then measure the length of the time period between interrogation signal and response to find a value of the distance between external charger and the internal charger.

Hence, the position of the first coil 109 of the implanted medical device 101 in relation to the external coil 153 or the distance therebetween can be calculated and information thereof can be fed back to the user. Information can also be fed back when the external charger 151 and in particular the second coil 153 is placed in an optimal position for transmitting energy to the internal charger.

The evaluation unit 166 thus generates a signal holding information about the current relative position of the external charger or the distance, respectively. This signal can be provided a display 157. In one embodiment the display is arranged to display the position relative to an optimal position. For example the display may comprise a number of light emitting diodes (LEDs) 157' of different colors indicating the current position or distance. For example a red light emitting diode may be lit when the external charger 151 is far off from an optimal position. When the external charger is moved closer to an optimal position, a yellow diode can be lit and when the external charger is in or close to an optimal position a green diode can be lit. Alternatively, the display can include single light source emitting light pulses with a repetition frequency that indicates the measured relative position, a higher repetition frequency indicating that the external coil 153 is closer to the optimal position or vice versa.

Furthermore, in order to provide such signals the successively determined values of the relative position or the distance between the external and internal chargers, obtained when the external charger 151 is being moved, can be further evaluated in a detecting unit 166' determining whether the relative position or the distance is currently being improved, i.e. more close, or is currently decreasing, respectively, or not, by comparing the latest determined relative position or value of the distance to the next latest determined position or value. This may be necessary in order to generate a signal provided to an indicator such as the display 157 or a loudspeaker or sound generating unit as will be described below.

Such a signal can thus indicate an improved or worsened relative position of the external charger 151 or and the at least one RFID transmitter 111 or a positive or negative change of the distance between the external charger and the at least one RFID transmitter. In the case where the at least one RFID transmitter is located in the external charger, the signal can indicate an improved or worsened relative position of the internal charger 107 or and the at least one RFID transmitter 167 or a positive or negative change of the distance between the external charger and the at least one RFID transmitter.

As a supplement or an alternative to the display 157 the external charger 151 can be provided with a unit 156 also receiving the signal holding information about the current relative position or distance and providing an audible signal, the characteristics of which is changed according to the determined relative position of or distance between the external charger and the internal charger 107. Thus, the audio unit can e.g. emit a sound signal having a low strength or a low pitch when the determined value of the relative position indicates a large distance and having a higher strength or a high pitch, respectively, when the determined value of the relative position indicates that external charger is closer to the internal charger value, the strength or pitch being set according to the determined distance, or vice versa. In an alternative the sound is emitted as pulses, the repetition frequency of which is changed depending on the value of the relative position.

The user moves the external charger 151 to find, using the output therefrom such as the visible indication on the display or the sound signal, the position in which optimal charging conditions exist. Thereupon, the use can tune the charging, i.e. the level of transfer or transmission of energy, to an optimal power level.

During the procedure of finding an optimal position the transceiver 155 can at regularly repeated times issue interrogation signals to the RFID transmitters/transmitter 111.

In the case illustrated in FIG. 11b the RFID transmitter or transmitters 167 are placed in the external charger 151 and the RFID receiver 130 in the internal charger 107. An evaluation unit 131 is arranged in the internal charger for evaluating the feedback information received from the RFID transmitter/transmitters. The result of the evaluation can be transmitted to the external charger using a transmitter 113 in the internal charger and a receiver 159 in the external charger.

In another embodiment the RFID transmitter/s/ are replaced with RFID receiver/s/ and the RFID receiver is replaced with an RFID transmitter, this case not shown in the drawings. Thus, e.g. the four RFID transmitters 111 of FIG. 11a could be replaced with RFID receivers and the RFID receiver with an RFID transmitter. Time periods between challenging or interrogating signals and responses or angles of the response signals can be measured as described above and evaluated by a unit in the internal charger 107. In an alternative, the four RFID transmitters of FIG. 11b could be replaced with four RFID receivers and the single RFID receiver 130 with an RFID transmitter. The evaluation unit is in the latter case placed in the external charger.

FIGS. 12a and 12b are schematics of another embodiments. In these embodiments the external charger 151 and/or the internal charger 107 is/are arranged to measure the mutual coupling between the external charger and internal charger using a coupling measurement device. In the case shown in FIG. 12a the coupling measurement device 158 is placed in the external charger. A user can sweep over or scan the skin of the patient with the external charger 151 using a low charging power to find, based on feedback from the coupling measurement device, an optimal position, the optimal position being the position in which the coupling measurement device indicates the highest coupling factor. After having found the optimal position providing optimum charging conditions, the user can tune the charging to an optimum power level of the transmitted field for charging the battery 109 of the implanted medical device 101.

The coupling measurement device 158 is in one embodiment arranged to analyze, such as in an analysis unit 160, the amount of energy being transmitted from the external charger 151 and also to receive feedback information about the amount of energy actually received by the internal charger 107. By calculating the ratio between the transmitted amount of energy and the received amount of energy a coupling factor can be determined. Furthermore, the successively determined values of the coupling factor, obtained when the external charger 151 is being moved, can be further evaluated in a detecting unit 160' determining whether the coupling factor is currently increasing or decreasing by comparing the latest determined value of the coupling factor to the next latest determined value.

For transmitting the feedback information an internal signal transmitter 113 and an external signal receiver 159 in or connected to the internal charger 107 and the external charger 151, respectively, may be implemented as separate units using suitable signal transfer means, such as using radio waves, IR (Infrared) or ultrasonic signals. Alternatively, the internal signal transmitter 1027 and the external signal receiver 1004c feedback information may be integrated in the implanted energy-transforming device 1002 and the external energy source 1004a, respectively, so as to convey control signals conveyed in a reverse direction relative to the energy transfer, basically using the same transmission technique. The control signals may be modulated with respect to frequency, phase method as in the transfer of energy, such as by varying or amplitude. modulating some electric characteristic of the internal coil 109, e.g. switching it on and off in predetermined patterns, as will be described below. In this case special control and detecting units included in the respective chargers are used. Such units can generally be represented by the shown internal signal transmitter 113 and the external signal receiver 159. Signal transmitting/modulating means and signal receiving/demodulating/detecting means such as the internal signal transmitter and the external signal receiver can be used in the embodiments described herein, where they are required, even if they are indicated the respective drawings.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. The switch 1026 can either be separate and controlled by the internal control unit 1015, or integrated in the internal control unit 1015. It should be understood that the switch 1026 can be implemented by any type of suitable device such as a transistor, MCU, MCPU, ASIC FPGA or a DA converter or any other electronic component or circuit that may switch the power on and off.

The energy supply arrangement illustrated in FIG. 16 may be operated in accordance with one embodiment in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004c. Alternatively, the energy balance can be determined by the external control unit 1004b instead depending on the implementation, as mentioned above. In that case, the control signal may carry measurement results from various sensors. The amount of energy emitted from the external energy source 1004a can then be regulated by the external control unit 1004b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004a, such as voltage, current, amplitude, wave frequency and pulse characteristics.

The system as described herein above may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 17:
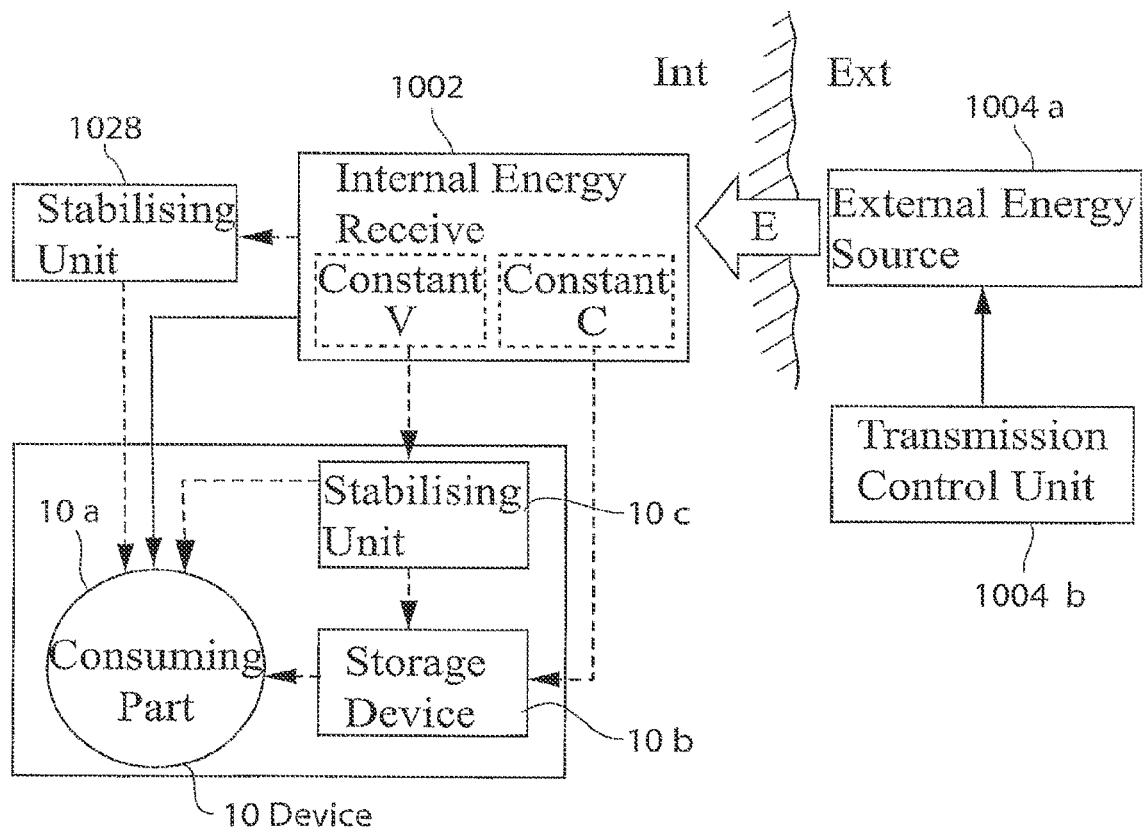
FIG. 17 is a more detailed block diagram of an apparatus for controlling transmission of wireless energy supplied to an electrically operable medical device implanted in a patient. The text contained herein should also be read as general summary of the invention and includes additional embodiments.

FIG. 17 illustrates different embodiments for how received energy can be supplied to and used by the implantable medical device 10. Similar to the example of FIG. 16, an internal energy receiver 1002 receives wireless energy E from an external energy source 1004a which is controlled by a transmission control unit 1004b. The internal energy receiver 1002 may comprise a constant voltage circuit, indicated as a dashed box "constant V" in the figure, for supplying energy at constant voltage to the implantable medical device 10. The internal energy receiver 1002 may further comprise a constant current circuit, indicated as a dashed box "constant C" in the figure, for supplying energy at constant current to the implantable medical device 10.

The implantable medical device 10 can comprise an energy consuming part 10a for example a motor, a pump, a restriction device, or any other medical appliance that requires energy for its electrical operation. The implantable medical device 10 may further comprise an energy storage device 10b for storing energy supplied from the internal energy receiver 1002. Thus, the supplied energy may be directly consumed by the energy consuming part 10a, or stored by the energy storage device 10b, or the supplied energy may be partly consumed and partly stored. The implantable medical device 10 may further comprise an energy stabilizing unit 10c for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the implantable medical device 10, before being consumed and/or stored by the implantable medical device 10. Alternatively, the energy stabilizing unit 1028 may be integrated in the internal energy receiver 1002. In either case, the energy stabilizing unit 1028 may comprise a constant voltage circuit and/or a constant current circuit.

Figure 18:
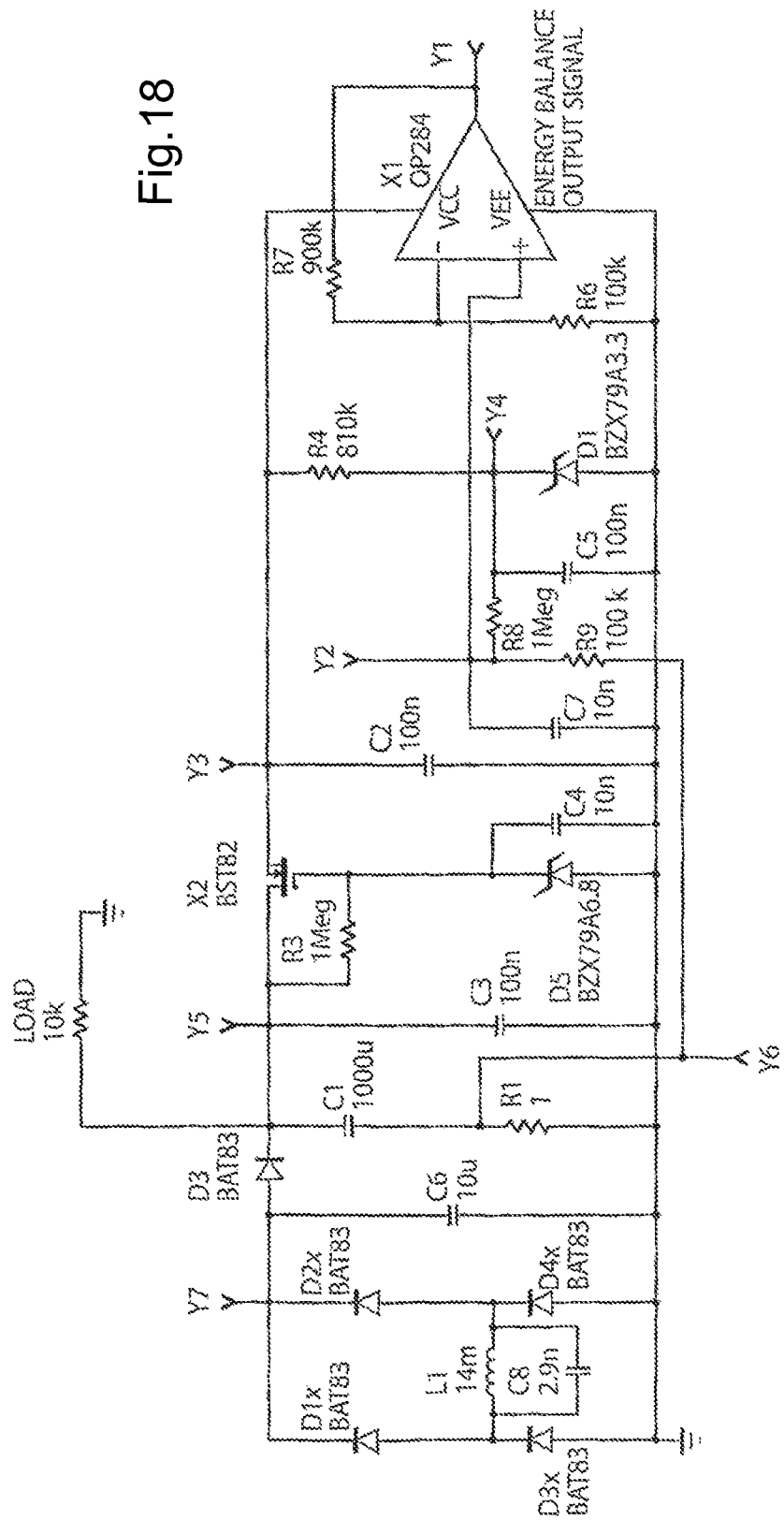
FIG. 18 is a circuit implementation diagram of for a system for controlling transmission of wireless energy and transferring energy to implanted components, according to a possible implementation example

FIG. 18 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the device, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 18 shows a circuit implementation for a system that transfers energy to the implanted energy components of the device of the present invention from outside of the patient's body using inductive energy transfer. An inductive energy transfer system typically uses an external transmitting coil and an internal receiving coil. The receiving coil, L1, is included and the transmitting parts of the system are excluded.

The implementation of the general concept of energy balance and the way the information is transmitted to the external energy transmitter can of course be implemented in numerous different ways. The schematic FIG. 18 and the above described method of evaluating and transmitting the information should only be regarded as examples of how to implement the control system.

Circuit Details

In FIG. 18 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. Please observe that the switch simply could mean any electronic circuit or component.

The embodiments described above identify a method and a system for controlling transmission of wireless energy to implanted energy consuming components of an electrically powered implantable medical device.

A method is thus provided for controlling transmission of wireless energy supplied to implanted energy consuming components of a device as described above. The wireless energy E is transmitted from an external energy source located outside the patient and is received by an internal energy receiver located inside the patient, the internal energy receiver being connected to the implanted energy consuming components of the device for directly or indirectly supplying received energy thereto. An energy balance is determined between the energy received by the internal energy receiver and the energy used for the device. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising a device as described above is thus also provided for controlling transmission of wireless energy supplied to implanted energy consuming components of the device. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the device for directly or indirectly supplying received energy thereto. The system further comprises a determination device adapted to determine an energy balance between the energy received by the internal energy receiver and the energy used for the implantable energy consuming components of the device, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the device, and the control device controls the transmission of wireless energy based on the detected energy difference.

The control device controls the external energy-transmission device to decrease the amount of transmitted wireless As a supplement or an alternative to the display 157 the external charger 151 can as above be provided with a unit 156 providing an audible signal, the characteristics of which is changed according to the determined coupling between the external charger and the internal charger 107 such as the determined value of the coupling factor. Thus, the audio unit can emit a sound signal having a low strength or a low pitch when the determined value of the coupling is small and having a higher strength or a high pitch, respectively, when the determined value of the coupling obtains a higher value, the strength or pitch being set according to the determined value. Also, the sound can be emitted as pulses, the repetition frequency of which is changed depending on the value of the coupling.

In an embodiment a switch 115 is provided in the internal power supply 104 for switching on and off the connection between all the other components of the implanted medical device 101 and the first coil 109 arranged for receiving energy from the external charger 151, the first coil thereby constituting an open loop in which an electric current cannot flow, this actually stopping the transfer of energy to the internal charger 107. The internal charger 107 can further provided with a transmission control device 116 connected to the switch 115 setting it on and off according to predetermined patterns, the patterns representing information related to the charging received by the internal charger. This switching on and off can be sensed by the external charger 151 as an impedance variation or impedance modulation of the second coil 153 such as by an impedance sensing unit 162 that can detect the information conveyed in the variations of the impedance. Alternatively, a separate transmitter and a separate receiver can be arranged in the internal charger and the external charger, for transmitting the information related to the charging.

In another embodiment a receiving or sensing unit 163 is provided in the external power supply 150 such as in the external charger 151 for receiving or sensing feedback information that is passively transmitted from the first coil 109, this embodiment not requiring a special control unit in the internal charger 109. Such passively generated feedback information can be obtained as the response induced in the internal, first coil when influenced by a power pulse or burst generated by the external power supply. Such a power pulse or power burst can basically include that a single electric current pulse is applied to the external coil 153 or a train of such pulses or that an electric alternating current is applied to the external coil for a short time period, such as a time period corresponding to half the or the whole period of the alternating current or to a few periods, e.g. two or three such periods. The receiving or sensing unit 163 is then arranged to detect e.g. the magnetic or electromagnetic field generated by the internal charger 107 as a response to the power burst or pulse. By determining the strength of the detected magnetic or electromagnetic field the external charger 151 can determine whether the position becomes better or worse when a user moves the external power supply over the skin of a patient having an implanted medical device 101 including or connected to an internal charger 107. An increase in the response magnetic or electromagnetic field indicates a better energy supply position.

For example, if the power pulse or burst includes only a single pulse such as a rectangular pulse, a voltage is induced in the first coil during the first, leading edge of the pulse. This voltage drives an electric current through the first coil, producing a secondary magnetic field which can be sensed by the receiving or sensing unit 163. If the power pulse or pulse includes a sinusoidal electric current, the first coil will produce a sinusoid ally varying magnetic field that can be sensed by the receiving or sensing unit.

In an initial calibration stage the power pulses or bursts can be transmitted with such characteristics as to increase the response generated by the first coil 109 from a first low level until the resulting magnetic or electromagnetic field can be sensed by the receiving or sensing unit 163. For a rectangular pulse this can include that the leading and/or trailing edges of the pulse are made more steep or that the pulse height is increased, this producing a stronger magnetic field and a magnetic field existing for a longer time period, respectively.

The generation of the power pulse or power burst can be controlled by a control unit 165 in the external charger 151. Such a control unit can control the various functions of the external charger and be provided also in other embodiments described herein whenever necessary or suitable, also in cases where such a control unit is not shown in the respective drawing.

The external power supply 150 may also comprise an analyzing unit similar to the analyzing unit 160 described above but in this case arranged to analyze the passively generated feedback information from the internal charger 107 such as a value of the strength of the detected magnetic or electromagnetic field and to generate a signal representing this information that can be displayed or indicated such as on the display 155 and/or using an audible signal. From the displayed or received information the user can optimize the placement of the external power supply 150 and in particular of the external charger 151 in relation to the internal charger 107 to optimize the transfer of energy to the internal power supply 104.

Furthermore, in order to initiate a procedure for finding an optimal position for charging the internal charger, the external charger 151 can be arranged to perform a calibration procedure involving a sequence of calibration steps as commanded by the control unit 165, as will be described in more detail below. For example, in order to generate a feedback signal from the internal charger 107, the external charger can be arranged or commanded to slowly, e.g. in predetermined steps, increase the level of transmitted energy or power, i.e. the level of the intensity of the current provided to the second coil 153, until a feedback signal is received from the internal charger 104. After a response has been detected and received from the internal charger, the user can start moving the external charger for finding the optimal charging position based on the feedback information from the internal charger.

In the embodiment of FIG. 12b the evaluation of the coupling is made in the internal charger 107 such as in an analysis unit 117. It can receive information about the received energy or power directly from other components of the internal charger and it can also receive information about the transmitted energy such from a receiver 114 receiving such information from a transmitter 164 in the external charger 151. The analysis unit can e.g. calculate a coupling factor and may also detect whether there is currently an increase or a decrease of the coupling factor. Information about the coupling, coupling factor and/or whether the coupling is increasing or decreasing can be sent to the external charger 151 using the transmitter 113 and receiver 159. The information received by the external charger can as above be used for generating a signal, such as an appropriate light signal or a sound signal.

An internal receiver and an external transmitter for receiving and sending control signals or information signals, such as the units 114 and 164 illustrated in FIG. 12b, can be arranged in the internal charger 107 and the external charger 164 also in other embodiments described herein, whenever necessary or suitable, also when symbols of such devices are not shown in the respective drawing.

FIG. 13a is a schematic, partly sectional view of an implanted medical device 101 and an external power supply 150 in which more details can be seen. The implanted medical device comprises or is connected to an internal power supply 104 also implanted in the patient. The internal power supply comprises or is connected to an internal charger 107 arranged to wirelessly receive, through the skin 170 of the patient as described above, energy from the external power supply 150 comprising or connected to an external charger 151. The internal charger is connected to an internal energy source such as an electrochemical cell or a battery 105. The internal energy source supplies energy used for driving active parts, such as mechanical parts, of the implanted medical device 101. The implanted medical device can comprise a control device working in a mechanical or hydraulic way. For example, the implanted medical device can comprise a control device for mechanically or hydraulically adjusting a member 108 located in conjunction with or at a blood vessel 112 or at some other internal organ for controlling the flow of a fluid in the vessel 112 or organ. In FIG. 13a the member 108 is shown as being mechanically or hydraulically adjusted to a generally closed position, thereby shutting off the flow of fluid in the vessel 112.

As can be seen in FIG. 13a, the internal power supply 104 can comprise two portions, a first portion holding the internal charger 107 and a second portion holding the internal energy source 105 and other components. The portions can be interconnected through a relatively narrow tubular part 118 in which the necessary electric lines, not shown, pass. The portions can be implanted at opposite sides of a diaphragm or membrane 119 in the patient's body, this giving the internal power supply a relatively well fixed position not allowing significant movements in the body tissues.

FIG. 13b is a fragmentary sectional view of the control device of the medical device 101. FIG. 13b corresponds to respective portion of FIG. 13a but shows the member 108 mechanically or hydraulically adjusted to a generally open position to allow free flow of the fluid in the vessel 112.

FIG. 14 is another fragmentary, partly sectional view of the internal power supply 104 and the external power supply 150 further illustrating the operation of the charging system as described herein. Hence, in order to find an optimal position of the external charger 151 comprised in or connected to the external power supply that is arranged to transmit energy to the internal charger 107, the external power supply and in particular the external charger is being moved over the skin 170 of the patient. In response to feedback information from the implanted medical device such as from the internal power supply or the internal charger the optimal position for charging the implanted medical device is searched for and selected. The operation of the charging system is further described below with reference to FIG. 15.

FIG. 15 is a flow chart illustrating steps performed when the charging system as described herein is used to find an optimal position for transmitting energy to the internal charger 104 which in turn is arranged to supply power to other parts of the implanted medical device 101. The steps can be commanded by a control unit in the external power supply such as the control unit 165 shown in FIGS. 12a and 12b. In a first step 601 the external charger 151 is turned on, the external charger is placed at some suitable place on the patient's body and procedure for finding the optimal position is started by e.g. pressing a button, not shown, on the external charger. Next in a step 603 the charger performs a calibration procedure in order to produce a response signal from the internal charger 104 that can be detected by the external charger. In the calibration procedure the level of the power supplied to the external coil 153 is increased, e.g. continuously or stepwise, i.e. the strength of the electromagnetic field generated by the external coil is increased by supplying an electric current having a gradually increasing intensity to the external coil. In the next step 605 the user or operator starts to move the external charger over the skin 170 of the patient. Thereupon, in a step 607, the user receives feedback information from the system allowing the user to move the external charger to a position that is more favorable for transmitting energy to the internal charger 107. Upon finding an optimal position the external charger 151 indicates this fact in a step 609 and the procedure ends in a final step 611.

It may happen that the initial position of the external charger 151 is far away from the internal charger 107. Then, the power supplied to the external coil 153 may be rather high in order to produce a response from the internal charger which of course is not desired since it could cause damages. In that case, it can be tested in the calibration step 603, when the external charger is moved whether now a lower power supplied to the external coil can be used. For example, the power can decreased until no response is obtained or received and then increased by a suitable step to produce a response. Such a procedure can be used at regular repeated times during the movement of the external charger 151 until a sufficiently low power is supplied to the external coil.

After the procedure for searching for an optimal position has been performed, the level of the power supplied to the external, second coil 153 is set to a value suitable for the energy transfer, e.g. as commanded by the control unit 165. It can e.g. be set to the lowest possible value that can achieve a desired charging of the internal energy source. Then, in such as setting operation a value of the electromagnetic coupling, if available, between the second coil 153 and the first coil 109, e.g. as representing by the coupling factor, can be considered, this generally resulting in that a low value of the coupling factor requires a high level of the power supplied to the external coil and that a higher value of the coupling factor requires a lower level.

FIG. 16 is a schematic view of an embodiment of an implanted medical device 101 and the charging and power supply system 100 thereof. The internal charger 107 acting as of an energy receiver comprises an energy-transforming device such as a first coil 109. The energy receiver can preferably be located just beneath or just inside the patient's skin 170. Generally, the implanted energy-transforming device or coil 109 may, as in all embodiments described herein, be placed in the abdomen, thorax, muscle fascia, e.g. in the abdominal wall, subcutaneously, or at any other suitable location in the patient's body. The implanted energy-transforming device or first coil 109 is arranged to wirelessly receive energy E transmitted from an external power supply 150 such as from an external charger 151 comprising a second coil 153 provided in the external power supply 150 when it is placed in the vicinity of the implanted energy-transforming device 109.

As is well known in the art, the energy E that is transferred to the internal charger 107 may generally be transferred by means of any suitable Transcutaneous Energy Transfer (TET) device or system, such as a device or system including a primary coil 153, herein also called second coil, arranged in the external charger 151, and an adjacent secondary coil 109, herein also called first coil, arranged in the implanted internal charger 107 as described above. When an alternating electric current flows in the primary coil, an alternating voltage is induced in the secondary coil which can be used to drive an electric current through the second coil that can be used to power energy consuming components 101' of the implanted medical device 101. The electric current flowing in the secondary coil represents received energy that e.g. can be stored in an implanted energy source, such as a rechargeable electrochemical cell or battery 105 or a capacitor. However, at least some aspects of the methods, systems and devices described herein are generally not limited to any particular method of transferring energy or power and to TET devices or energy sources of any particular kind, and in such cases wireless energy transfer of any suitable kind may be used.

The amount of energy received by the implanted, internal charger 107, that can be called an internal energy receiver, may be compared to the energy used by the other implanted components of the system or apparatus. The term "energy used" is then understood to include also energy stored by implanted components of the apparatus but of course not the energy stored in the energy source such as the battery 105 included in or connected to the internal charger 107. A control device, i.e. basically the control system of the energy transfer system, includes an external control unit 165 that controls the external energy source 153 based on the determined energy balance to regulate the amount of transferred energy. In order to transfer the correct amount of energy, the energy balance and the required amount of energy is determined by a determination device including an implanted internal control unit 120 connected between a switch 115 and a main portion of the implanted medical device 101. The internal control unit 120 may thus be arranged to receive various measurements obtained by suitable sensors or the like, not shown, measuring certain characteristics of the implanted medical device 101, somehow reflecting the required amount of energy needed for proper operation of the components of the implanted medical device 101. Moreover, the current condition of the patient may also be detected by suitable measuring devices or sensors, not shown, to provide parameters reflecting the patient's condition. Hence, such characteristics and/or parameters may be related to the current state of the implanted medical device 101, such as power consumption, operational mode and temperature, as well as the patient's condition reflected by parameters such as body temperature, blood pressure, heart beat rate and breathing. Physical parameters of the patient of other kinds and functional parameters of the device are described elsewhere.

Furthermore, an energy source such as an accumulator 1016 may optionally be connected to the implanted energy-transforming device 1002 via the control unit 1015 for accumulating received energy for later use by the implanted medical device. Alternatively or additionally, characteristics of such an accumulator, also reflecting the required amount of energy, may be measured as well. The accumulator may be a rechargeable electrochemical cell or battery, and the measured characteristics may be related to the current state of the battery, any electrical parameter such as energy consumption voltage, temperature, etc. In order to provide sufficient voltage and electric current to drive the other components of the implanted medical device 101, and also to avoid excessive heating, it is clearly understood that the battery should be charged optimally by receiving a correct amount of energy from the implanted energy-transforming device 109, i.e. not too little and not too much. The accumulator may also be a capacitor having corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 120 of the determination device is arranged to determine the energy balance and/or the currently required amount of energy, either energy per time unit or accumulated energy, based on measurements made by the above-mentioned sensors or measuring devices of the implantable medical device 101 or of the patient or of an implanted energy source if used, or any combination thereof. The internal control unit 1015 can further be connected to an internal signal transmitter 113, arranged to transmit a control signal S reflecting the determined required amount of energy, to an external signal receiver 159 included or connected to the external charger 151. The amount of energy transmitted from the external energy source 153 may then be regulated in response to the received control signal.

Alternatively, the determination device may include the external charger 151. In this alternative, sensor measurements can be transferred to the external control unit 165 in which the received values resulting from the sensor measurements are evaluated to determine the energy balance and/or the currently required amount of energy, thus integrating the above-described function of the internal control unit 120 in the external charger 151. In this case, the internal control unit 120 can be omitted and the sensor measurements are supplied directly to the internal signal transmitter 113 which sends the measurements to the external signal receiver 159 from which they are forwarded to the external control unit. The external control unit determines the energy balance and the currently required amount of energy based on the sensor measurements and produces a control signal controlling the external energy transmitter 153, setting a required or suitable level of the energy transfer.

Hence, the system of FIG. 16 employs the feedback of information indicating the required energy, which is more efficient than other methods solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for being directly consumed or for storing the energy in an implanted energy source 105 or the like. The different parameters discussed above would thus be used if relevant and needed and then as a tool for determining the actual energy balance. However, such parameters may also be needed per se for any actions taken internally to specifically operate the apparatus.

The internal signal transmitter 113 and the external signal receiver 159 may as above be implemented as separate units using suitable signal transfer means, such as radio, IR (Infrared) or ultrasonic signals. Alternatively, the internal signal transmitter 113 and the external signal receiver 159 may be integrated in the implanted energy-transforming device 109 and the external energy source 153, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy transfer system. Such an integrated information feedback and energy system can comprise an implantable internal energy receiver for wirelessly receiving energy, the energy receiver having an internal first coil 109 and a first electronic circuit connected to the first coil, and an external energy transmitter for wirelessly transmitting energy, the energy transmitter having an external second coil 153 and a second electronic circuit connected to the second coil. The external second coil of the energy transmitter wirelessly transmits energy which is received by the first coil of the energy receiver. The system further comprises a power switch 115 for switching the connection of the internal first coil 109 to the first electronic circuit on and off, such that feedback information related to the charging of the first coil is received by the external energy transmitter as an impedance variation of the external second coil 153, when the power switch switches the connection of the internal first coil to the first electronic circuit on and off. The impedance variation can e.g. be detected by determining the intensity or amplitude of the electric current through the second coil. The second coil is generally the load in an electric circuit, not shown, that includes a main power supply e.g. connected to "mains" or the public electric distribution network, and the electric current flowing therethrough can be sensed by the main power supply.

The power switch 115 can be controlled to be closed or open according to any suitable pattern, such as for example periodically, e.g. the times when the power switch is closed can occur in a regularly repeated pattern and the times when the power switch is closed can occur in a regularly repeated pattern, the patterns having the same repetition frequency. In an alternative the closing and opening of the power switch occur at random times in order not to interfere with other electronic components.

The impedance variation is generally detected or received as a variation between two levels, a maximum level and a minimum level. The variation, i.e. the distance between the two extreme levels, then represents or indicates the electromagnetic coupling between the second coil 153 and the first coil 109. When the external power supply/external charger is being moved in relation to the internal power supply/internal charger, the moving of the external power supply results in a variation of the distance between the two levels depending on the position of said external power supply in relation to the internal power supply. The feedback information such as the impedance variation or some quantity derived therefrom can as described above be used to generate a signal and/or indications to a user. Such indications can then include that it is indicated whether the value of the variation, during the moving of the external power supply, is increasing or decreasing, an increasing value indicating a higher or better electromagnetic coupling or a lower or worse electromagnetic coupling.

In the same way as described above, the external power supply can in an initial stage calibrate the system by increasing the amount of transferred energy to the internal power supply until a response of said switching on and off variation is detected by the external supply, i.e. basically until an impedance variation different from zero, or generally above a suitable positive threshold value, is detected.

The switch 153 can either be separate and controlled by the internal control unit 120 or be integrated in the internal control unit. It should be understood that the switch 153 can be implemented by any type of suitable device such as a transistor, MCU, MCPU, ASIC FPGA or a DA converter or any other electronic component or circuit that may switch the power on and off.

The energy supply arrangement illustrated in FIG. 16 may in one embodiment be operated in the following manner. The energy balance is first determined by the internal control unit 120 of the determination device. A control signal reflecting the required amount of energy is also created by the internal control unit, and the control signal is transmitted from the internal signal transmitter 113 to the external signal receiver 159. Alternatively, the energy balance can instead be determined by the external control unit 165 depending on the implementation, as mentioned above. In the latter case, the control signal may carry measurement results from various sensors. The amount of energy emitted from the external energy source 153 can then be regulated by the external control unit 165, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 153, such as voltage, current, amplitude, wave frequency and pulse characteristics.

The system as described herein above may also be used to obtain information about the coupling factors between the coils 109, 153 in a TET system even to calibrate the system both to find an optimal place for the external coil in relation to the internal coil and to optimize energy transfer. In this case the amount of energy transferred is compared to the amount of energy received. For example, if the external coil is being moved the coupling factor may vary and correctly performed movements could result in the fact that the optimal place of the external coil for energy transfer is found. Preferably, the control unit 165 for external coil 153 is arranged to calibrate the amount of transferred energy to achieve the feedback information in the determination device, before the coupling factor is maximized.

This coupling factor information may also be used as a feedback during energy transfer. In such a case, the energy transfer system as described herein comprises an implantable internal energy receiver for wirelessly receiving energy, the energy receiver having an internal first coil 109 and a first electronic circuit connected to the first coil, and an external energy transmitter for wirelessly transmitting energy, the energy transmitter having an external second coil 153 and a second electronic circuit connected to the second coil. The external second coil of the energy transmitter wirelessly transmits energy which is received by the first coil of the energy receiver. The system further comprises a feedback device for communicating a value of the amount of energy received in the first coil 109 as feedback information, wherein the second electronic circuit includes a determination device for receiving the feedback information and for comparing the amount of transferred energy by the second coil 153 to the feedback information related to the amount of energy received in the first coil in order to obtain the coupling factor between the second coil and the first coil. The energy transmitter may regulate the transmitted energy in response to the obtained value of the coupling factor.

FIG. 16 is a schematic view of an embodiment of an implanted medical device 101 and the charging and power supply system 100 thereof. The internal charger 107 acting as of an energy receiver comprises an energy-transforming device such as a first coil 109. The energy receiver can preferably be located just beneath or just inside the patient's skin 170. Generally, the implanted energy-transforming device or coil 109 may, as in all embodiments described herein, be placed in the abdomen, thorax, muscle fascia, e.g. in the abdominal wall, subcutaneously, or at any other suitable location in the patient's body. The implanted energy-transforming device or first coil 109 is arranged to wirelessly receive energy E transmitted from an external power supply 150 such as from an external charger 151 comprising a second coil 153 provided in the external power supply 150 when it is placed in the vicinity of the implanted energy-transforming device 109.

As is well known in the art, the energy E that is transferred to the internal charger 107 may generally be transferred by means of any suitable Transcutaneous Energy Transfer (TET) device or system, such as a device or system including a primary coil 153, herein also called second coil, arranged in the external charger 151, and an adjacent secondary coil 109, herein also called first coil, arranged in the implanted internal charger 107 as described above. When an alternating electric current flows in the primary coil, an alternating voltage is induced in the secondary coil which can be used to drive an electric current through the second coil that can be used to power energy consuming components 101' of the implanted medical device 101. The electric current flowing in the secondary coil represents received energy that e.g. can be stored in an implanted energy source, such as a rechargeable electrochemical cell or battery 105 or a capacitor. However, at least some aspects of the methods, systems and devices described herein are generally not limited to any particular method of transferring energy or power and to TET devices or energy sources of any particular kind, and in such cases wireless energy transfer of any suitable kind may be used.

The amount of energy received by the implanted, internal charger 107, that can be called an internal energy receiver, may be compared to the energy used by the other implanted components of the system or apparatus. The term "energy used" is then understood to include also energy stored by implanted components of the apparatus but of course not the energy stored in the energy source such as the battery 105 included in or connected to the internal charger 107. A control device, i.e. basically the control system of the energy transfer system, includes an external control unit 165 that controls the external energy source 153 based on the determined energy balance to regulate the amount of transferred energy. In order to transfer the correct amount of energy, the energy balance and the required amount of energy is determined by a determination device including an implanted internal control unit 120 connected between a switch 115 and a main portion of the implanted medical device 101. The internal control unit 120 may thus be arranged to receive various measurements obtained by suitable sensors or the like, not shown, measuring certain characteristics of the implanted medical device 101, somehow reflecting the required amount of energy needed for proper operation of the components of the implanted medical device 101. Moreover, the current condition of the patient may also be detected by suitable measuring devices or sensors, not shown, to provide parameters reflecting the patient's condition. Hence, such characteristics and/or parameters may be related to the current state of the implanted medical device 101, such as power consumption, operational mode and temperature, as well as the patient's condition reflected by parameters such as body temperature, blood pressure, heart beat rate and breathing. Physical parameters of the patient of other kinds and functional parameters of the device are described elsewhere.

Furthermore, an energy source such as an accumulator 1016 may optionally be connected to the implanted energy-transforming device 1002 via the control unit 1015 for accumulating received energy for later use by the implanted medical device. Alternatively or additionally, characteristics of such an accumulator, also reflecting the required amount of energy, may be measured as well. The accumulator may be a rechargeable electrochemical cell or battery, and the measured characteristics may be related to the current state of the battery, any electrical parameter such as energy consumption voltage, temperature, etc. In order to provide sufficient voltage and electric current to drive the other components of the implanted medical device 101, and also to avoid excessive heating, it is clearly understood that the battery should be charged optimally by receiving a correct amount of energy from the implanted energy-transforming device 109, i.e. not too little and not too much. The accumulator may also be a capacitor having corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 120 of the determination device is arranged to determine the energy balance and/or the currently required amount of energy, either energy per time unit or accumulated energy, based on measurements made by the above-mentioned sensors or measuring devices of the implantable medical device 101 or of the patient or of an implanted energy source if used, or any combination thereof. The internal control unit 1015 can further be connected to an internal signal transmitter 113, arranged to transmit a control signal S reflecting the determined required amount of energy, to an external signal receiver 159 included or connected to the external charger 151. The amount of energy transmitted from the external energy source 153 may then be regulated in response to the received control signal.

Alternatively, the determination device may include the external charger 151. In this alternative, sensor measurements can be transferred to the external control unit 165 in which the received values resulting from the sensor measurements are evaluated to determine the energy balance and/or the currently required amount of energy, thus integrating the above-described function of the internal control unit 120 in the external charger 151. In this case, the internal control unit 120 can be omitted and the sensor measurements are supplied directly to the internal signal transmitter 113 which sends the measurements to the external signal receiver 159 from which they are forwarded to the external control unit. The external control unit determines the energy balance and the currently required amount of energy based on the sensor measurements and produces a control signal controlling the external energy transmitter 153, setting a required or suitable level of the energy transfer.

Hence, the system of FIG. 16 employs the feedback of information indicating the required energy, which is more efficient than other methods solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for being directly consumed or for storing the energy in an implanted energy source 105 or the like. The different parameters discussed above would thus be used if relevant and needed and then as a tool for determining the actual energy balance. However, such parameters may also be needed per se for any actions taken internally to specifically operate the apparatus.

The internal signal transmitter 113 and the external signal receiver 159 may as above be implemented as separate units using suitable signal transfer means, such as radio, IR (Infrared) or ultrasonic signals. Alternatively, the internal signal transmitter 113 and the external signal receiver 159 may be integrated in the implanted energy-transforming device 109 and the external energy source 153, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy transfer system. Such an integrated information feedback and energy system can comprise an implantable internal energy receiver for wirelessly receiving energy, the energy receiver having an internal first coil 109 and a first electronic circuit connected to the first coil, and an external energy transmitter for wirelessly transmitting energy, the energy transmitter having an external second coil 153 and a second electronic circuit connected to the second coil. The external second coil of the energy transmitter wirelessly transmits energy which is received by the first coil of the energy receiver. The system further comprises a power switch 115 for switching the connection of the internal first coil 109 to the first electronic circuit on and off, such that feedback information related to the charging of the first coil is received by the external energy transmitter as an impedance variation of the external second coil 153, when the power switch switches the connection of the internal first coil to the first electronic circuit on and off. The impedance variation can e.g. be detected by determining the intensity or amplitude of the electric current through the second coil. The second coil is generally the load in an electric circuit, not shown, that includes a main power supply e.g. connected to "mains" or the public electric distribution network, and the electric current flowing therethrough can be sensed by the main power supply.

The power switch 115 can be controlled to be closed or open according to any suitable pattern, such as for example periodically, e.g. the times when the power switch is closed can occur in a regularly repeated pattern and the times when the power switch is closed can occur in a regularly repeated pattern, the patterns having the same repetition frequency. In an alternative the closing and opening of the power switch occur at random times in order not to interfere with other electronic components.

The impedance variation is generally detected or received as a variation between two levels, a maximum level and a minimum level. The variation, i.e. the distance between the two extreme levels, then represents or indicates the electromagnetic coupling between the second coil 153 and the first coil 109. When the external power supply/external charger is being moved in relation to the internal power supply/internal charger, the moving of the external power supply results in a variation of the distance between the two levels depending on the position of said external power supply in relation to the internal power supply. The feedback information such as the impedance variation or some quantity derived therefrom can as described above be used to generate a signal and/or indications to a user. Such indications can then include that it is indicated whether the value of the variation, during the moving of the external power supply, is increasing or decreasing, an increasing value indicating a higher or better electromagnetic coupling or a lower or worse electromagnetic coupling.

In the same way as described above, the external power supply can in an initial stage calibrate the system by increasing the amount of transferred energy to the internal power supply until a response of said switching on and off variation is detected by the external supply, i.e. basically until an impedance variation different from zero, or generally above a suitable positive threshold value, is detected.

The switch 153 can either be separate and controlled by the internal control unit 120 or be integrated in the internal control unit. It should be understood that the switch 153 can be implemented by any type of suitable device such as a transistor, MCU, MCPU, ASIC FPGA or a DA converter or any other electronic component or circuit that may switch the power on and off.

The energy supply arrangement illustrated in FIG. 16 may in one embodiment be operated in the following manner. The energy balance is first determined by the internal control unit 120 of the determination device. A control signal reflecting the required amount of energy is also created by the internal control unit, and the control signal is transmitted from the internal signal transmitter 113 to the external signal receiver 159. Alternatively, the energy balance can instead be determined by the external control unit 165 depending on the implementation, as mentioned above. In the latter case, the control signal may carry measurement results from various sensors. The amount of energy emitted from the external energy source 153 can then be regulated by the external control unit 165, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 153, such as voltage, current, amplitude, wave frequency and pulse characteristics.

The system as described herein above may also be used to obtain information about the coupling factors between the coils 109, 153 in a TET system even to calibrate the system both to find an optimal place for the external coil in relation to the internal coil and to optimize energy transfer. In this case the amount of energy transferred is compared to the amount of energy received. For example, if the external coil is being moved the coupling factor may vary and correctly performed movements could result in the fact that the optimal place of the external coil for energy transfer is found. Preferably, the control unit 165 for external coil 153 is arranged to calibrate the amount of transferred energy to achieve the feedback information in the determination device, before the coupling factor is maximized.

This coupling factor information may also be used as a feedback during energy transfer. In such a case, the energy transfer system as described herein comprises an implantable internal energy receiver for wirelessly receiving energy, the energy receiver having an internal first coil 109 and a first electronic circuit connected to the first coil, and an external energy transmitter for wirelessly transmitting energy, the energy transmitter having an external second coil 153 and a second electronic circuit connected to the second coil. The external second coil of the energy transmitter wirelessly transmits energy which is received by the first coil of the energy receiver. The system further comprises a feedback device for communicating a value of the amount of energy received in the first coil 109 as feedback information, wherein the second electronic circuit includes a determination device for receiving the feedback information and for comparing the amount of transferred energy by the second coil 153 to the feedback information related to the amount of energy received in the first coil in order to obtain the coupling factor between the second coil and the first coil. The energy transmitter may regulate the transmitted energy in response to the obtained value of the coupling factor.

FIG. 17 is a block diagram illustrating various embodiments related to the ways in which received energy can be supplied to and used by the implantable medical device 101. Similar to the example of FIG. 16, an internal energy receiver 109 wirelessly receives energy E from an external energy source 153 which is controlled by a transmission control unit 165. The internal energy receiver 109 may comprise or be connected to a constant voltage circuit, indicated as a dashed box "Constant V" in the figure, for supplying energy at constant voltage to the energy consuming parts 101' of the implantable medical device 101. The internal energy receiver 109 may further comprise a constant current circuit, indicated as a dashed box "Constant I" in the figure, for supplying energy at a constant current intensity to the implantable medical device 101.

The implantable medical device 101 can comprise an energy consuming part or component 101', for example a motor, a pump, a restriction device, or any other medical appliance that requires electric energy for its operation. The implantable medical device 101 may further comprise an energy storage device 105 for storing energy supplied from the internal energy receiver 109. Thus, the supplied energy may be directly consumed by the energy consuming part 101', or stored in the energy storage device 105, or the supplied energy may be partly directly consumed and partly stored. The implantable medical device 101 may further comprise an energy stabilizing unit 121 for stabilizing the energy supplied from the internal energy receiver 109. Thus, the energy may be supplied in a fluctuating manner such that it may be necessary to stabilize the energy before consumed or stored.

The energy supplied from the internal energy receiver 109 may further be accumulated and/or stabilized by a separate energy stabilizing unit 122 located outside the internal charger 107, before being consumed and/or stored by the energy consuming part 101' of the implantable medical device 101. Alternatively, the energy stabilizing unit may be integrated in the internal energy receiver 109. In either case, the energy stabilizing unit may comprise a constant voltage circuit and/or a constant current circuit.

FIG. 18 is a circuit diagram of an energy balance measuring circuit of one design of the system for controlling the wireless transmission of energy or of an energy balance control system. The circuit has an output signal that is centered at 2.5 V and is proportionally related to the energy imbalance. The derivative of this signal indicates whether the value is increasing or decreasing and the velocity with which such a change is taking place. If the amount of received energy or power is lower than the energy or power used by implanted components of the device, more energy is transferred and thus charged into the internal energy source. The output signal of the circuit is typically feed to an A/D converter and converted to a digital shape. The digital information can then be sent to the external energy-transmission device allowing it to adjust the level of the transmitted energy. Another possibility is to have a completely analog system that uses comparators comparing the energy balance level to certain maximum and minimum thresholds sending information to the external energy-transmission device if the balance drifts out of the maximum/minimum window.

In particular, FIG. 18 is a circuit diagram of a system for transferring energy to the implanted energy components of the device from outside the patient's body using inductive energy transfer. An inductive energy transfer system typically uses an external transmitting coil and an internal receiving coil. The receiving coil, L1, is included and the transmitting parts of the system are excluded.

The implementation of the general concept of energy balance and the way in which the information is transmitted to the external energy transmitter can of course be made in a multitude of different ways. The circuit diagram of FIG. 18 and the above described method of evaluating and transmitting the information should only be regarded as examples of possible ways in which the control system can be implemented.

Circuit Details

In FIG. 18 the symbols Y1, Y2, Y3 and so on symbolize test points within the circuit. The components in the circuit diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. It can e.g. be observed that the switch simply could mean any electronic circuit or component.

The embodiments described above are related to a method and a system for controlling wireless transmission of energy to implanted energy consuming components of an electrically powered implantable medical device.

A method is thus provided for controlling wireless transmission of energy supplied to implanted energy consuming components of a device as described above. The energy E is wirelessly transmitted from an external energy source located outside the patient and is received by an internal energy receiver located inside the patient, the internal energy receiver being connected to the implanted energy consuming components of the device for directly or indirectly supplying received energy thereto. An energy balance is determined between the energy received by the internal energy receiver and the energy used for the device. The wireless transmission of energy E from the external energy source is then controlled based on the determined energy balance.

The energy that is wirelessly transmitted may e.g. be transmitted inductively from a primary coil in the external energy source to a secondary coil in the internal energy receiver. A change in the energy balance may be detected to control the wireless transmission of energy based on the detected energy balance change. A difference may also be detected between energy received by the internal energy receiver and energy used for the medical device, to control the wireless transmission of energy based on the detected energy difference.

When controlling the energy transmission, the amount of wirelessly transmitted energy may be decreased if the detected energy balance change implies that the energy balance is increasing, or vice versa. The decrease/increase of energy transmission may further correspond to a detected change rate.

The amount of wirelessly transmitted energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or electric current related to the energy balance.

The wireless transmission of energy from the external energy source may be controlled by applying, to the external energy source, electrical pulses from a first electric circuit to wirelessly transmit the energy, the electrical pulses having leading and trailing edges, varying the lengths of first time intervals between successive leading and trailing edges of the electrical pulses and/or the lengths of second time intervals between successive trailing and leading edges of the electrical pulses, and wirelessly transmitting energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied as a group of pulses, wherein when applying the train of pulses, the train having a first electrical pulse at the start of the pulse train and having a second electrical pulse at the end of the pulse train, two or more pulse trains may be supplied sequentially or successively, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising a device as described above is thus also provided for controlling wireless transmission of energy supplied to implanted energy consuming components of the device. In its broadest sense, the system comprises a control device for controlling the wireless transmission of energy from an energy-transmission device, and an implantable internal energy receiver for receiving the wirelessly transmitted energy, the internal energy receiver being connected to implantable energy consuming components of the device for directly or indirectly supplying received energy thereto. The system further comprises a determination device arranged to determine an energy balance between the energy received by the internal energy receiver and the energy used for the implantable energy consuming components of the device, wherein the control device controls the wireless transmission of energy from the external energy-transmission device, based on the energy balance determined by the determination device.

Further, the system may comprise any of the following:

A primary coil in the external energy source is arranged to wirelessly transmit the energy inductively to a secondary coil in the internal energy receiver.

The determination device is arranged to detect a change in the energy balance, and the control device controls the wireless transmission of energy based on the detected energy balance change The determination device is arranged to detect a difference between energy received by the internal energy receiver and energy used for the implantable energy consuming components of the device, and the control device controls the wireless transmission of energy based on the detected energy difference.

The control device controls the external energy-transmission device to decrease the amount of wirelessly transmitted energy if the detected energy balance change implies that the energy balance is increasing, or vice versa, wherein the decrease/increase of energy transmission corresponds to a detected change rate.

The control device controls the external energy-transmission device to decrease the amount of wirelessly transmitted energy if the detected energy difference implies that the received energy is greater than the used energy, or vice versa, wherein the decrease/increase of energy transmission corresponds to the magnitude of said detected energy difference.

The energy used for the device is consumed to operate the device, and/or stored in at least one energy storage device of the device.

In the case where electrical and/or physical parameters of the device and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

In the case where the derivative of a measured electrical parameter over time is determined that is related to the amount of consumed and/or stored energy, the determination device determines the derivative for a monitored voltage and/or a monitored electric current related to the energy balance.

The energy-transmission device comprises a coil placed externally to the human body, and an electric circuit is provided to power the external coil with electrical pulses to wirelessly transmit the energy. The electrical pulses have leading and trailing edges, and the electric circuit is arranged to vary first time intervals between successive leading and trailing edges and/or second time intervals between successive trailing and leading edges of the electrical pulses to vary the power of the wirelessly transmitted energy. As a result, the energy receiver receiving the wirelessly transmitted energy has a varied power.

The electric circuit is arranged to deliver the electrical pulses to remain unchanged except varying the first and/or second time intervals.

The electric circuit has a time constant and is arranged to vary the first and second time intervals only in the range of the first time constant, so that when the lengths of the first and/or second time intervals are varied, the transmitted power over the coil is varied.

The electric circuit is arranged to deliver the electrical pulses to be varied by only varying the lengths of first time intervals between successive leading and trailing edges of the electrical pulses.

The electric circuit is arranged to supply a train of two or more sequential or successive electrical pulses, said train having a first electrical pulse at the start of the pulse train and having a second electrical pulse at the end of the pulse train, where the lengths of the second time intervals between successive trailing edge of the second electrical pulse in a first pulse train and leading edge of the first electrical pulse of a second pulse train are varied by the first electronic circuit.

The electric circuit is arranged to provide the electrical pulses as pulses having a substantially constant height and/or amplitude and/or intensity and/or voltage and/or electric current intensity and/or frequency.

The electric circuit has a time constant, and is arranged to vary the first and second time intervals only in the range of the first time constant, so that when the lengths of the first and/or second time intervals are varied, the transmitted power over the first coil are varied.

The electric circuit is arranged to provide the electrical pulses varying the lengths of the first and/or the second time intervals only within a range that includes the first time constant or that is located relatively close to the first time constant, compared to the magnitude of the first time constant.

The internal or implantable devices described herein can be implanted in the body of a patient using a suitable surgical procedure such as that illustrated by the flow chart of FIG. 19. For example, an implantable device can be implanted by inserting a needle or a tubular instrument into the patient's abdominal cavity, step 1201. Next in a step 1203 a part of the patient's body is supplied with gas using the needle or tubular instrument thereby expanding the abdominal cavity. Next in a step 1205 at least two laparoscopic trocars are placed in the cavity. Thereupon in a step 1207 a camera is inserted through one of the laparoscopic trocars into the cavity. Next in a step 1209 at least one dissecting tool is inserted through one of said at least two laparoscopic trocars. An area where the device is to be placed is then dissected in a step 1211. The device is then placed in the area in a step 1213, and the device is adjusted and enabled in a final step 1215.

In another embodiment an implantable device can be implanted using a procedure illustrated by the flow chart of FIG. 20. First in a step 1301*a* needle or a tubular instrument is inserted into the patient's thoraxial cavity. Next, in a step 1303 a part of the patient's body is supplied with gas using the needle or tubular instrument to fill and thereby expand the thoraxial cavity. Thereupon at least two laparoscopic trocars are placed in the cavity in a step 1305 Thereupon in a step 1307 a camera is inserted through one of the laparoscopic trocars into the cavity. Next in a step 1309 at least one dissecting tool is inserted through one of said at least two laparoscopic trocars. An area is then dissected in a step 1311. The device is then placed in the area in a step 1313, and the device is adjusted and enabled in a final step 1315.

Figure 21:
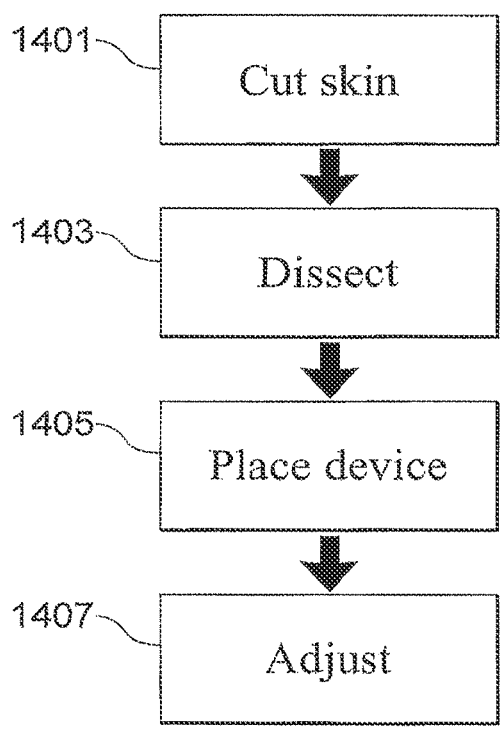

In another embodiment the implantable device can be implanted using a procedure illustrated by the flow chart of FIG. 21. First in a step 1401, the skin in the abdominal or thoraxial wall of the mammal patient is cut. Next, in a step 1403 an area is dissected. Next, the device is placed in the area in a step 1405, and the device is adjusted and enabled in a final step 1407.

Figure 22:
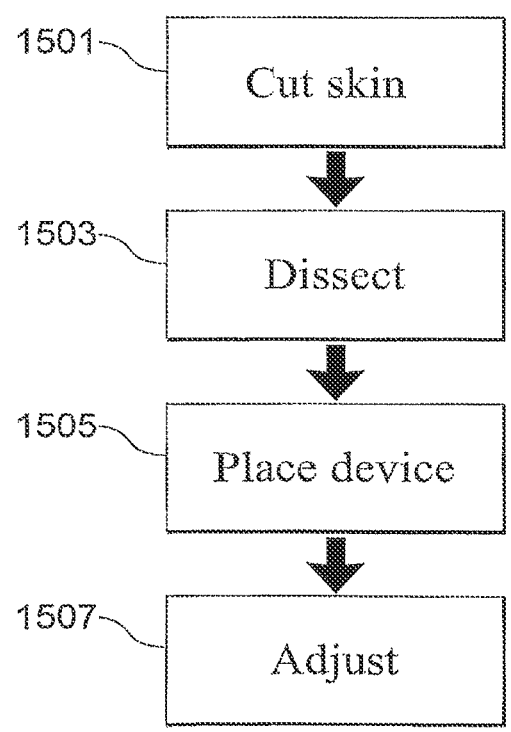

In another embodiment the implantable device can be implanted using a procedure illustrated by the flow chart of FIG. 22. First in a step 1501, the skin of the mammal patient is cut. Next, in a step 1503 an area is dissected. Next, the device is placed in the area in a step 1505, the gas pressure is released and the device is adjusted and enabled in a final step 1507.

It should be observed that the description above illustrate some possible but non-limiting implementation options regarding the ways in which the various shown functional components and elements can be arranged and connected to each other. However, a person skilled in the art will readily appreciate that many variations and modifications can be made within the scope of the present invention.

A use of the method, systems and devices described herein will in many cases provide an efficient transfer, in at least some cases even a more efficient transfer compared to prior art systems and devices, of energy from an external charger to an internal charger providing electric power to an implanted medical device.

Description of possible implementation examples to be viewed also as a general description of different embodiments.

The information contained in the description of FIG. 17 should also be read as general text to be added to the summary of the invention and includes additional features and embodiments of the invention.

FIG. 17 illustrates different embodiments for how received energy can be supplied to and used by a medical device 10. Similar to the example of FIG. 1, an internal energy receiver 1002 receives wireless energy E from an external energy source 1004a which is controlled by a transmission control unit 1004b. The internal energy receiver 1002 may comprise a constant voltage circuit, indicated as a dashed box "constant V" in the figure, for supplying energy at constant voltage to the medical device 10. The internal energy receiver 1002 may further comprise a constant current circuit, indicated as a dashed box "constant C" in the figure, for supplying energy at constant current to the medical device 10.

The medical device 10 comprises an energy consuming part 10a which may be a motor, pump, restriction device, or any other medical appliance that requires energy for its electrical operation. The medical device 10 may further comprise an energy storage device 10b for storing energy supplied from the internal energy receiver 1002. Thus, the supplied energy may be directly consumed by the energy consuming part 10a or stored by the energy storage device 10b, or the supplied energy may be partly consumed and partly stored. The medical device 10 may further comprise an energy stabilizing unit 10c for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the medical device 10, before being consumed and/or stored by the medical device 10. Alternatively, the energy stabilizing unit 1028 may be integrated in the internal energy receiver 1002. In either case, the energy stabilizing unit 208 may comprise a constant voltage circuit and/or a constant current circuit.

It should be noted that FIG. 1 and FIG. 17 illustrate some possible but non-limiting implementation options regarding how the various shown functional components and elements can be arranged and connected to each other. However, the skilled person will readily appreciate that many variations and modifications can be made within the scope of the present invention.

A method is thus provided for controlling transmission of wireless energy supplied to an electrically operable medical device implanted in a patient. The wireless energy is transmitted from an external energy source located outside the patient and is received by an internal energy receiver located inside the patient, the internal energy receiver being connected to the medical device for directly or indirectly supplying received energy thereto. An energy balance is determined between the energy received by the internal energy receiver and the energy used for the medical device. the transmission of wireless energy from the external energy source is then controlled based on the determined energy balance.

An apparatus is also provided for controlling transmission of wireless energy supplied to an electrically operable medical device implanted in a patient. The apparatus is adapted to transmit the wireless energy from an external energy source located outside the patient which is received by an internal energy receiver located inside the patient, the internal energy receiver being connected to the medical device for directly or indirectly supplying received energy thereto. The apparatus is further adapted to determine an energy balance between the energy received by the internal energy receiver and the energy used for the medical device, and control the transmission of wireless energy from the external energy source, based on the determined energy balance.

The method and apparatus may be implemented according to different embodiments and features as follows.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

In one alternative, substantially all energy used for the medical device is consumed (e.g. by the energy consuming part 10a of FIG. 17) to operate the medical device. In that case, the energy may be consumed after being stabilized in at least one energy stabilizing unit of the medical device.

In another alternative, substantially all energy used for the medical device is stored in the at least one energy storage device. In yet another alternative, the energy used for the medical device is partly consumed to operate the medical device and partly stored in the at least one energy storage device.

The energy received by the internal energy receiver may be stabilized by a capacitor, before the energy is supplied directly or indirectly to the medical device.

The difference between the total amount of energy received by the internal energy receiver and the total amount of consumed and/or stored energy may be directly or indirectly measured over time, and the energy balance can then be determined based on a detected change in the total amount difference.

The energy received by the internal energy receiver may further be accumulated and stabilized in an energy stabilizing unit, before the energy is supplied to the medical device. In that case, the energy balance may be determined based on a detected change followed over time in the amount of consumed and/or stored energy. Further, the change in the amount of consumed and/or stored energy may be detected by determining over time the derivative of a measured electrical parameter related to the amount of consumed and/or stored energy, where the derivative at a first given moment is corresponding to the rate of the change at the first given moment, wherein the rate of change includes the direction and speed of the change. The derivative may further be determined based on a detected rate of change of the electrical parameter.

The energy received by the internal energy receiver may be supplied to the medical device with at least one constant voltage, wherein the constant voltage is created by a constant voltage circuitry. In that case, the energy may be supplied with at least two different voltages, including the at least one constant voltage.

The energy received by the internal energy receiver may also be supplied to the medical device with at least one constant current, wherein the constant current is created by a constant current circuitry. In that case, the energy may be supplied with at least two different currents including the at least one constant current.

The energy balance may also be determined based on a detected difference between the total amount of energy received by the internal energy receiver and the total amount of consumed and/or stored energy, the detected difference being related to the integral over time of at least one measured electrical parameter related to the energy balance. In that case, values of the electrical parameter may be plotted over time as a graph in a parameter-time diagram, and the integral can be determined from the size of the area beneath the plotted graph. The integral of the electrical parameter may relate to the energy balance as an accumulated difference between the total amount of energy received by the internal energy receiver and the total amount of consumed and/or stored energy.

The energy storage device in the medical device may include at least one of: a rechargeable battery, an accumulator or a capacitor. The energy stabilizing unit may include at least one of: an accumulator, a capacitor or a semiconductor adapted to stabilize the received energy.

When the energy received by the internal energy receiver is accumulated and stabilized in an energy stabilizing unit before energy is supplied to the medical device and/or energy storage device, the energy may be supplied to the medical device and/or energy storage device with at least one constant voltage, as maintained by a constant voltage circuitry. In that case, the medical device and energy storage device may be supplied with at least two different voltages, wherein at least one voltage is constant, maintained by the constant voltage circuitry.

Alternatively, when the energy received by the internal energy receiver is accumulated and stabilized in an energy stabilizing unit before energy is supplied to the medical device and/or energy storage device, the energy may be supplied to the medical device and/or energy storage device with at least one constant current, as maintained by a constant current circuitry. In that case, the medical device and energy storage device may be supplied with at least two different currents wherein at least one current is constant, maintained by the constant current circuitry.

The wireless energy may be initially transmitted according to a predetermined energy consumption plus storage rate. In that case, the transmission of wireless energy may be turned off when a predetermined total amount of energy has been transmitted. The energy received by the internal energy receiver may then also be accumulated and stabilized in an energy stabilizing unit before being consumed to operate the medical device and/or stored in the energy storage device until a predetermined total amount of energy has been consumed and/or stored.

Further, the wireless energy may be first transmitted with the predetermined energy rate, and then transmitted based on the energy balance which can be determined by detecting the total amount of accumulated energy in the energy stabilizing unit. Alternatively, the energy balance can be determined by detecting a change in the current amount of accumulated energy in the energy stabilizing unit. In yet another alternative, the energy balance, can be determined by detecting the direction and rate of change in the current amount of accumulated energy in the energy stabilizing unit.

The transmission of wireless energy may be controlled such that an energy reception rate in the internal energy receiver corresponds to the energy consumption and/or storage rate. In that case, the transmission of wireless energy may be turned off when a predetermined total amount of energy has been consumed.

The energy received by the internal energy receiver may be first accumulated and stabilized in an energy stabilizing unit, and then consumed or stored by the medical device until a predetermined total amount of energy has been consumed. In that case, the energy balance may be determined based on a detected total amount of accumulated energy in the energy stabilizing unit. Alternatively, the energy balance may be determined by detecting a change in the current amount of accumulated energy in the energy stabilizing unit. In yet another alternative, the energy balance may be determined by detecting the direction and rate of change in the current amount of accumulated energy in the energy stabilizing unit.

As mentioned in connection with FIG. 1, suitable sensors may be used for measuring certain characteristics of the medical device and/or detecting the current condition of the patient, somehow reflecting the required amount of energy needed for proper operation of the medical device. Thus, electrical and/or physical parameters of the medical device and/or physical parameters of the patient may be determined, and the energy can then be transmitted with a transmission rate which is determined based on the parameters. Further, the transmission of wireless energy may be controlled such that the total amount of transmitted energy is based on said parameters.

The energy received by the internal energy receiver may be first accumulated and stabilized in an energy stabilizing unit, and then consumed until a predetermined total amount of energy has been consumed. The transmission of wireless energy may further be controlled such that an energy reception rate at the internal energy receiver corresponds to a predetermined energy consumption rate.

Further, electrical and/or physical parameters of the medical device and/or physical parameters of the patient may be determined, in order to determine the total amount of transmitted energy based on the parameters. In that case, the energy received by the internal energy receiver may be first accumulated and stabilized in an energy stabilizing unit, and then consumed until a predetermined total amount of energy has been consumed.

The energy is stored in the energy storage device according to a predetermined storing rate. The transmission of wireless energy may then be turned off when a predetermined total amount of energy has been stored. The transmission of wireless energy can be further controlled such that an energy reception rate at the internal energy receiver corresponds to the predetermined storing rate.

The energy storage device of the medical device may comprise a first storage device and a second storage device, wherein the energy received by the internal energy receiver is first stored in the first storage device, and the energy is then supplied from the first storage device to the second storage device at a later stage.

When using the first and second storage devices in the energy storage device, the energy balance may be determined in different ways. Firstly, the energy balance may be determined by detecting the current amount of energy stored in the first storage device, and the transmission of wireless energy may then be controlled such that a storing rate in the second storage device corresponds to an energy reception rate in the internal energy receiver. Secondly, the energy balance may be determined based on a detected total amount of stored energy in the first storage device. Thirdly, the energy balance may be determined by detecting a change in the current amount of stored energy in the first storage device. Fourthly, the energy balance may be determined by detecting the direction and rate of change in the current amount of stored energy in the first storage device.

Stabilized energy may be first supplied from the first storage device to the second storage device with a constant current, as maintained by a constant current circuitry, until a measured voltage over the second storage device reaches a predetermined maximum voltage, and thereafter supplied from the first storage device to the second storage energy storage device with a constant voltage, as maintained by a constant voltage circuitry. In that case, the transmission of wireless energy may be turned off when a predetermined minimum rate of transmitted energy has been reached.

The transmission of energy may further be controlled such that the amount of energy received by the internal energy receiver corresponds to the amount of energy stored in the second storage device. In that case, the transmission of energy may be controlled such that an energy reception rate at the internal energy receiver corresponds to an energy storing rate in the second storage device. The transmission of energy may also be controlled such that a total amount of received energy at the internal energy receiver corresponds to a total amount of stored energy in the second storage device.

In the case when the transmission of wireless energy is turned off when a predetermined total amount of energy has been stored, electrical and/or physical parameters of the medical device and/or physical parameters of the patient may be determined during a first energy storing procedure, and the predetermined total amount of energy may be stored in a subsequent energy storing procedure based on the parameters.

When electrical and/or physical parameters of the medical device and/or physical parameters of the patient are determined, the energy may be stored in the energy storage device with a storing rate which is determined based on the parameters. In that case, a total amount of energy may be stored in the energy storage device, the total amount of energy being determined based on the parameters. The transmission of wireless energy may then be automatically turned off when the total amount of energy has been stored. The transmission of wireless energy may further be controlled such that an energy reception rate at the internal energy receiver corresponds to the storing rate.

When electrical and/or physical parameters of the medical device and/or physical parameters of the patient are determined, a total amount of energy may be stored in the energy storage device, the total amount of energy being determined based on said parameters. The transmission of energy may then be controlled such that the total amount of received energy at the internal energy receiver corresponds to the total amount of stored energy. Further, the transmission of wireless energy may be automatically turned off when the total amount of energy has been stored.

When the energy used for the medical device is partly consumed and partly stored, the transmission of wireless energy may be controlled based on a predetermined energy consumption rate and a predetermined energy storing rate. In that case, the transmission of energy may be turned off when a predetermined total amount of energy has been received for consumption and storage. The transmission of energy may also be turned off when a predetermined total amount of energy has been received for consumption and storage.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When electrical and/or physical parameters of the medical device and/or physical parameters of the patient are determined, the energy may be supplied from the energy storage device to the medical device for consumption with a supply rate which is determined based on said parameters. In that case, the total amount of energy supplied from the energy storage device to the medical device for consumption, may be based on said parameters.

When electrical and/or physical parameters of the medical device and/or physical parameters of the patient are determined, a total amount of energy may be supplied to the medical device for consumption from the energy storage device, where the total amount of supplied energy is determined based on the parameters.

When the energy received by the internal energy receiver is accumulated and stabilized in an energy stabilizing unit, the energy balance may be determined based on an accumulation rate in the energy stabilizing unit, such that a storing rate in the energy storage device corresponds to an energy reception rate in the internal energy receiver.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

When using the first and second storage devices in the energy storage device, the second storage device may directly or indirectly supply energy to the medical device, wherein the change of the difference corresponds to a change of the amount of energy accumulated in the first storage unit. The energy balance may then be determined by detecting a change over time in the energy storing rate in the first storage device, the energy balance corresponding to the change. The change in the amount of stored energy may also be detected by determining over time the derivative of a measured electrical parameter indicating the amount of stored energy, the derivative corresponding to the change in the amount of stored energy. A rate of change of the electrical parameter may also be detected, the derivative being related to the change rate. The electrical parameter may be a measured voltage and/or current related to the energy balance.

The first storage device may include at least one of: a capacitor and a semiconductor, and the second storage device includes at least one of: a rechargeable battery, an accumulator and a capacitor.

As mentioned above, the wireless energy may be transmitted inductively from a primary coil in the external energy source to a secondary coil in the internal energy receiver. However, the wireless energy may also be transmitted non-inductively. For example, the wireless energy may be transmitted by means of sound or pressure variations, radio or light. The wireless energy may also be transmitted in pulses or waves and/or by means of an electric field.

When the wireless energy is transmitted from the external energy source to the internal energy receiver in pulses, the transmission of wireless energy may be controlled by adjusting the width of the pulses.

When the difference between the total amount of energy received by the internal energy receiver and the total amount of consumed energy is measured over time, directly or indirectly, the energy balance may be determined by detecting a change in the difference. In that case, the change in the amount of consumed energy may be detected by determining over time the derivative of a measured electrical parameter related to the amount of consumed energy, the derivative corresponding to the rate of the change in the amount of consumed energy, wherein the rate of change includes the direction and speed of the change. A rate of change of the electrical parameter may then be detected, the derivative being related to the detected change rate.

When using the first and second storage devices in the energy storage device, the first storage device may be adapted to be charged at a relatively higher energy charging rate as compared to the second storage device, thereby enabling a relatively faster charging. The first storage device may also be adapted to be charged at multiple individual charging occasions more frequently as compared to the second storage device, thereby providing relatively greater life-time in terms of charging occasions. The first storage device may comprise at least one capacitor. Normally, only the first storage may be charged and more often than needed for the second storage device.

When the second storage device needs to be charged, to reduce the time needed for charging, the first storage device is charged at multiple individual charging occasions, thereby leaving time in between the charging occasions for the first storage device to charge the second storage device at a relatively lower energy charging rate. When electrical parameters of the medical device are determined, the charging of the second storage device may be controlled based on the parameters. A constant current or stabilizing voltage circuitry may be used for storing energy in the second storage device.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

When applying electrical pulses to the external energy source, the electrical pulses may generate an electromagnetic field over the external energy source, the electromagnetic field being varied by varying the first and second time intervals, and the electromagnetic field may induce electrical pulses in the internal energy receiver, the induced pulses carrying energy transmitted to the internal energy receiver. The wireless energy is then transmitted in a substantially purely inductive way from the external energy source to the internal energy receiver.

The electrical pulses may be released from the first electrical circuit with such a frequency and/or time period between leading edges of the consecutive pulses, so that when the lengths of the first and/or second time intervals are varied, the resulting transmitted energy are varied. When applying the electrical pulses, the electrical pulses may have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

While the invention has been described with reference to specific exemplary embodiments, the description is in general only intended to illustrate the inventive concept and should not be taken as limiting the scope of the invention. In particular, the skilled person will readily understand that the above-described embodiments and examples can be implemented both as a method and an apparatus. The present invention and various possible embodiments are generally defined by the following claims.

The invention claimed is:

1. A method for controlling wireless transmission of energy supplied to an electrically powered medical device when implanted in a patient, the method comprising powering the medical device by an internal energy receiver of the medical device, wirelessly supplying energy to the internal energy receiver by an external energy source located externally to the patient, wherein the external energy source is equipped with a primary coil from which the external energy source inductively transmits said energy to a first secondary coil in the energy receiver, the method further comprising: determining, by measurements, one or more parameters related to a first coupling factor between the primary coil and the first secondary coil,
    transmitting, by the external energy source, a first amount of energy to the energy receiver for enabling the medical device, to detect, information related to the first coupling factor,
    sending wirelessly feedback information related to said first coupling factor to the external energy source, receiving, at the external energy source, said feedback information from the medical device,
    performing, by the external energy source, a predetermined action based on said feedback information, and at least one of;
    letting the first secondary coil be substantially without electrical load when measuring the parameters related to the first coupling factor, and
    providing an electronic component connected to said first secondary coil, for preventing or substantially reducing the flow of electrical current between the first secondary coil and the medical implant during the measurements of parameters related to the first coupling factor.

2. The method of claim 1, in which said predetermined action comprises optimizing the placement of the primary coil in relation to the first secondary coil in order to optimize said first coupling factor.

3. The method of claim 2, wherein said first coupling factor is used to determine a second amount of energy to be transmitted by said external energy source to the internal energy receiver, said second amount of energy being optimized to power or charge the medical device.

4. The method of claim 1, wherein said first amount of energy is increased until said first coupling factor is detected by the system.

5. The method of claim 2, further comprising indicating, by an indicator in the external energy source, at least one of; an optimal placement of the primary coil in relation to said first secondary coil, and a level of the first coupling factor, in order to optimize the first coupling factor.

6. The method of claim 1, further comprising directly or indirectly measuring over a predetermined period of time the difference between an electrical parameter related to the energy transmitted by the external energy source and an electrical parameter related to the amount of energy received by the internal energy receiver, and determining the balance between said electrical parameters in order to determine said first coupling factor.

7. The method of claim 1, further comprising rectifying, by a half wave rectifying component in the energy receiver, half of the pulse cycle of a received alternating current energy signal in the energy receiver, and measuring parameters related to the first coupling factor during at least part of the non-rectified half of one or more pulse cycles.

8. The method of claim 1, further comprising switching a connection between the first secondary coil and the medical implant on and off by a first switch in the energy receiver, in order to enable measuring of the first coupling factor when the connection is off.

9. The method of claim 1, further comprising receiving, by a determination device of a second external control unit of the external energy source, feedback information from a first internal control unit, comparing, by the determination device, the amount of transferred energy by the primary coil with the feedback information related to the amount of energy received in the first secondary coil to obtain the coupling factor between the primary and secondary coils, and regulating and calibrating, by the external control unit, the transmitted energy in response to the obtained coupling factor.

10. The method of claim 1, further comprising receiving, by an internal control unit of the medical device, information related to said first coupling factor from said external energy source and measuring internal information within the medical device related to said first coupling factor, calculating, by the internal control unit, the feedback information based on said received and measured internal information, and transmitting said feedback information from said internal control unit, the feedback information comprising complete information relating to said first coupling factor.

11. The method of claim 1, further comprising at least one of; stabilizing, by at least one energy stabilizing unit in the medical device, wirelessly received energy prior to use by the medical device, wherein the energy stabilizing unit comprises a capacitor, and storing, by an internal energy storage device, energy during said energy transfer, for use by the medical device.

12. The method of claim 1, wherein at least one of the parameters are measured by at least one of; an integration and a derivative.

13. The method of claim 1, further comprising handling, by an external control unit in said external energy source, the detected information related to said first coupling factor, using the coupling factor information as a feedback during energy transfer, the energy receiver having a first electronic circuit connected to the first secondary coil, transmitting wireless energy by an external energy transmitter in the external energy source, the energy transmitter having a second electronic circuit connected to the primary coil, wherein the method further comprises communicating out, by a feedback device, information related to the amount of energy received in the first coil as a feedback information, receiving, by a determination device in the second electronic circuit, the feedback information and comparing the amount of transferred energy by the primary coil with the feedback information related to the amount of energy received in the first secondary coil to obtain the coupling factor between the first secondary and primary coils, and regulating and calibrating, by the external control unit, the transmitted energy in response to the obtained coupling factor.

14. The method of claim 1, further comprising
determining, by an internal control unit, a second energy balance between the energy received by the energy receiver and the energy used by the medical device, with the feedback information/control information also relating to said determined second energy balance, and
at least one of; calibrating and controlling, by an external control unit, the transmission of wireless energy from the energy source based on at least one of; the first coupling factor, and the determined second energy balance, by using said feedback information/control information.

15. The method of claim 1, further comprising storing, in a memory unit, information related to the first coupling factor.

16. The method of claim 1, wherein an implantable internal control unit and within the external energy source an external control unit is provided, the method further comprising at least one of;
a) increasing said first amount of energy transferred from the external energy source until said first coupling factor is detected,
b) optimizing in said predetermined action the placement of the primary coil in relation to the first secondary coil in order to optimize said first coupling factor,
c) using said first coupling factor to determine and calibrate a second amount of energy to be transmitted by said external energy source,
d) measuring during energy transfer the coupling factor, to intermittently calibrate the energy transfer,
e) determining a second energy balance between the energy received by the energy receiver and the energy used by the medical device,
f) transferring feedback information/control information relating to said determined second energy balance and information related to the coupling factor, out from the body by said internal control unit, and
g) calibrating and controlling the transmission of wireless energy from the energy source by said external control unit based on at least one of; the first coupling factor, and the determined second energy balance, by using said feedback information/control information.

17. The method of claim 1, comprising wirelessly transmitting energy by an external energy transmitter, the energy transmitter having a second electronic circuit connected to the primary coil, wherein the method further comprises communicating, by a feedback device, a value related to the amount of energy received in the first secondary coil as feedback information, receiving, by a determination device in the second electronic circuit, the feedback information and comparing the amount of transferred energy by the second coil to the feedback information related to the amount of energy received in the first secondary coil in order to obtain the coupling factor between the primary coil and the first secondary coil, regulating, by the energy transmitter, the transmitted energy in response to the obtained value of the coupling factor, and using, by the external energy source, said feedback information to regulate and calibrate the level of transmitted energy.

18. The method of claim 1, wherein the transmission of wireless energy from the external energy source is controlled by applying to the external energy source electrical pulses from a electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals, the method further comprising remaining the electrical pulses unchanged except for varying the first and/or second time intervals between successive leading and trailing edges of the electrical pulses, and thus the frequency and amplitude of the electrical pulses are substantially constant when varying the first and/or second time intervals.

19. A method for controlling wireless transmission of energy supplied to an electrically powered medical device when implanted in a patient, the method comprising powering the medical device by an internal energy receiver of the medical device, wirelessly supplying energy to said internal energy receiver by an external energy source located externally to the patient, wherein the external energy source is equipped with a primary coil from which the external energy source inductively transmits said energy to a first secondary coil in the energy receiver, the method further comprising determining, by measurements, one or more parameters related to a first coupling factor between the primary and the first secondary coil, transmitting, by the external energy source, a first amount of energy to the energy receiver for enabling detecting, by the medical device, information related to the first coupling factor, wirelessly sending feedback information related to said first coupling factor to the external energy source, receiving, by the external energy source, said feedback information from the medical device, performing, by the external energy source, a predetermined action based on said feedback information, and switching, by a first switch in the energy receiver, a connection between the first secondary coil and the medical implant on and off, in order to enable measuring of the first coupling factor when the connection is off.

20. A method for controlling wireless transmission of energy supplied to an electrically powered medical device when implanted in a patient, the method comprising powering the medical device by an internal energy receiver of the medical device, wirelessly supplying energy to the internal energy receiver by an external energy source be located externally to the patient, wherein the external energy source is equipped with a primary coil from which the external energy source inductively transmits said energy to a first secondary coil in the energy receiver, the method further comprising determining, by measurements, one or more parameters related to a first coupling factor between the primary and the first secondary coil, transmitting, by the external energy source, a first amount of energy to the energy receiver for enabling detecting, by the medical device, information related to the first coupling factor, wirelessly sending feedback information related to said first coupling factor to the external energy source, receiving, by the external energy source, said feedback information from the medical device, performing, by the external energy source, a predetermined action based on said feedback information, and preventing, by an electronic component connected to the first secondary coil, flow of electrical current between the first secondary coil and the medical implant during measurement of parameters related to the first coupling factor.

21. A method for controlling wireless transmission of energy supplied to an electrically powered medical device when implanted in a patient, the method comprising powering the medical device by an internal energy receiver of the medical device, wirelessly supplying energy to the internal energy receiver by an external energy source located externally to the patient, wherein the external energy source is equipped with a primary coil from which the external energy source inductively transmits said energy to a first secondary coil in the energy receiver, wherein the energy receiver further comprises a second secondary coil, so that the primary coil has a first coupling factor in relation to the first secondary coil and a second coupling factor in relation to the second secondary coil, with the first secondary coil being arranged to receive energy for powering the medical device and the second secondary coil being adapted to supply information related to the second coupling factor, wherein the second coupling factor has a predetermined relation to the first coupling factor, the method further comprising:

- determining, by measurements, one or more parameters related to a second coupling factor between the primary coil and the second secondary coil,
- transmitting, by the external energy source, a first amount of energy to the energy receiver for enabling the medical device, to detect, information related to the second coupling factor,
- sending wirelessly feedback information related to said second coupling factor to the external energy source,
- receiving, at the external energy source, said feedback information from the medical device,
- performing, by the external energy source, a predetermined action based on said feedback information, and at least one of the following;
- letting the second secondary coil be substantially without electrical load when measuring parameters related to the second coupling factor, and
- providing an electronic component connected to said second secondary coil, for preventing or substantially reducing the flow of electrical current between the second secondary coil and the medical implant during the measurements of parameters related to the second coupling factor, the method further comprising the step of;
- determining said second coupling factor, using the parameters related to the second coupling factor.

* * * * *